(12) United States Patent
Nishide et al.

(10) Patent No.: US 10,326,138 B2
(45) Date of Patent: Jun. 18, 2019

(54) CHARGE STORAGE MATERIAL, ELECTRODE ACTIVE MATERIAL AND SECONDARY BATTERY

(71) Applicants: WASEDA UNIVERSITY, Tokyo (JP); NISSAN CHEMICAL INDUSTRIES, LTD., Tokyo (JP)

(72) Inventors: Hiroyuki Nishide, Tokyo (JP); Kenichi Oyaizu, Tokyo (JP); Yuya Kambe, Tokyo (JP); Takuji Yoshimoto, Funabashi (JP)

(73) Assignees: Waseda University, Tokyo (JP); Nissan Chemical Industries, Ltd., Tokyo (JP)

( * ) Notice: Subject to any disclaimer, the term of this patent is extended or adjusted under 35 U.S.C. 154(b) by 167 days.

(21) Appl. No.: 15/065,564

(22) Filed: Mar. 9, 2016

(65) Prior Publication Data

US 2017/0077518 A1 Mar. 16, 2017

(30) Foreign Application Priority Data

Sep. 11, 2015 (JP) .................................. 2015-179565
Mar. 3, 2016 (JP) .................................. 2016-040936

(51) Int. Cl.
*H01B 1/00* (2006.01)
*H01M 4/00* (2006.01)
(Continued)

(52) U.S. Cl.
CPC ............. *H01M 4/608* (2013.01); *C07C 50/04* (2013.01); *C07D 471/04* (2013.01); *C08G 65/00* (2013.01);
(Continued)

(58) Field of Classification Search
CPC .......... H01B 1/00; H01B 1/121; C07C 50/04; C07C 50/18; C07C 249/00; C07C 251/00; C08G 65/00
See application file for complete search history.

(56) References Cited

U.S. PATENT DOCUMENTS

2014/0377666 A1* 12/2014 Kodama ........... H01M 10/0567
429/324

FOREIGN PATENT DOCUMENTS

CN      103022496 A  *  4/2013
JP      2002-117852 A    4/2002
(Continued)

OTHER PUBLICATIONS

Nakahara et al., "Rechargeable batteries with organic radical cathodes," Chemical Physics Letters (Jun. 27, 2002), vol. 359, pp. 351-354.
(Continued)

*Primary Examiner* — Mark Kopec
(74) *Attorney, Agent, or Firm* — Birch, Stewart, Kolasch & Birch, LLP

(57) ABSTRACT

Materials having charge-storing properties and made variously of dipyridine-fused benzoquinones of formula (1)
(Continued)

below or derivatives thereof, dipyridine-fused benzoquinones of formula (4) below or derivatives thereof, or dipyridine-fused benzoquinone skeleton-containing polymers are provided.

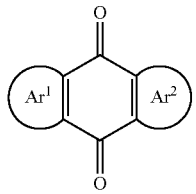

(1)

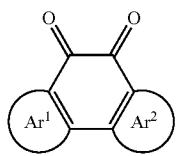

(4)

In the formulas, $Ar^1$ and $Ar^2$ are each independently a pyridine ring that forms together with two carbon atoms on a benzoquinone skeleton, or a derivative thereof. When used as electrode active materials, these charge storage materials are capable of providing high-performance batteries possessing a high capacity, high rate characteristics and high cycle characteristics.

15 Claims, 13 Drawing Sheets

(51) Int. Cl.
| | | |
|---|---|---|
| *H01M 12/00* | (2006.01) | |
| *C08G 65/00* | (2006.01) | |
| *H01M 4/60* | (2006.01) | |
| *C07D 471/04* | (2006.01) | |
| *C08G 73/06* | (2006.01) | |
| *H01M 12/06* | (2006.01) | |
| *H01M 10/0525* | (2010.01) | |
| *H01B 1/12* | (2006.01) | |
| *C07C 50/04* | (2006.01) | |
| *H01M 4/02* | (2006.01) | |

(52) U.S. Cl.
CPC ......... *C08G 73/0688* (2013.01); *H01B 1/121* (2013.01); *H01M 10/0525* (2013.01); *H01M 12/06* (2013.01); *H01M 2004/028* (2013.01)

(56) References Cited

FOREIGN PATENT DOCUMENTS

| JP | 2008-147015 A | 6/2008 |
| JP | 2009-217992 A | 9/2009 |
| JP | 2010-44882 A | 2/2010 |
| JP | 2010-55923 A | 3/2010 |
| JP | 2010-80343 A | 4/2010 |
| JP | 2010-212152 A | 9/2010 |

OTHER PUBLICATIONS

Nishide, H. and T. Suga, "Organic Radical Battery," the Electrochemical Society Interface (Winter 2005), vol. 14, pp. 32-36.
Uemachi et al., "Poly(1,4-phenylene-1,2,4-dithiazole-3',5'-yl): the new redox system for lithium secondary batteries," Electrochimica Acta (2001), vol. 46, pp. 2305-2312.
Visco et al., "A Novel Class of Organosulfur Electrodes for Energy Storage," J. Electrochem. Soc., (Mar. 1989), vol. 136, No. 3, pp. 661-664.
Vlad et al., "Hybrid supercapacitor-battery materials for fast electrochemical charge storage," Scientific Reports (Mar. 7, 2014), vol. 4, pp. 4315-4321.

\* cited by examiner

CHARGE STORAGE MATERIAL, ELECTRODE ACTIVE MATERIAL AND SECONDARY BATTERY

CROSS-REFERENCE TO RELATED APPLICATION

This non-provisional application claims priority under 35 U.S.C. § 119(a) on Patent Application Nos. 2015-179565 and 2016-040936 filed in Japan on Sep. 11, 2015 and Mar. 3, 2016, respectively, the entire contents of which are hereby incorporated by reference.

TECHNICAL FIELD

This invention relates to charge storage materials, electrode active materials and secondary batteries.

BACKGROUND ART

Organic secondary batteries, which are rechargeable batteries that use an organic charge storage material as an electrode active material in the battery, are attracting considerable attention on account of such features as their high rate characteristics, high capacity retention with charge-discharge cycling, lightweight thin-film construction and potential physical flexibility. Nitroxy radical-containing compounds are often used as the organic charge storage material (Chem. Phys. Lett. 359, 0.351-354 (2002); Electrochem. Soc. Interface 14, 32-36 (2005); JP-A 2002-117852), although the use of organosulfur polymers (J. Electrochem. Soc. 136, 661-664 (1989); Electrochimica Acta 46, 2305-2312 (2001)), quinone polymers (JP-A 2009-217992), quinoid materials (JP-A 2010-44882, JP-A 2010-55923, JP-A 2010-80343), dione materials (JP-A 2010-212152) and rubeanic acid-based materials (JP-A 2008-147015) has also been reported.

In recent years, it has been shown that, by using an organic charge storage material in the presence of an inorganic electrode active material, the capacity and voltage retention (collectively referred to below as the "rate characteristics") during high-speed charge and discharge of a lithium ion battery and the capacity retention (referred to below as the "cycle characteristics") in charge-discharge cycling can be improved (Scientific Reports 4, 4315-4321 (2014)), thus expanding applicable uses and methods for organic charge storage materials.

CITATION LIST

Patent Document 1: JP-A 2002-117852
Patent Document 2: JP-A 2009-217992
Patent Document 3: JP-A 2010-44882
Patent Document 4: JP-A 2010-55923
Patent Document 5: JP-A 2010-80343
Patent Document 6: JP-A 2010-212152
Patent Document 7: JP-A 2008-147015
Non-Patent Document 1: Chem. Phys. Lett. 359, 351-354 (2002)
Non-Patent Document 2: Electrochem. Soc. Interface 14, 32-36 (2005)
Non-Patent Document 3: J. Electrochem. Soc. 136, 661-664 (1989)
Non-Patent Document 4: Electrochimica Acta 46, 2305-2312 (2001)
Non-Patent Document 5: Scientific Reports 4, 4315-4321 (2014)

SUMMARY OF THE INVENTION

However, batteries which use nitroxy radical-containing charge storage materials as the electrode active material have a smaller charge storage capacity than batteries which use inorganic electrode active materials. When use has been made of organic charge storage materials having a high capacity, such as organosulfur polymers, drawbacks have included a low electrochemical stability, the inability to obtain sufficient cycle characteristics, and also a low voltage. Other organic charge storage materials as well, when used alone as the electrode active material or when used together with an inorganic electrode active material, in addition to the above drawbacks, typically fall short in terms of, for example, resistance to dissolution by the electrolyte solution, swellability that enables sufficient ion ingress and egress, ionic conductivity, and bindability with the inorganic electrode active material and current collector. Hence, satisfactory performance as a secondary battery, particularly a lithium ion battery, has sometimes been unattainable.

It is therefore an object of this invention to provide materials having charge storing properties which, when used as electrode active materials, are capable of giving high-performance batteries that have a high voltage, a high capacity, high rate characteristics and high cycle characteristics.

The inventors have found that dipyridine-fused benzoquinone and derivatives thereof, and also polymers containing a dipyridine-fused benzoquinone skeleton, function as charge storage materials and that when such charge storage materials are used as electrode active materials, they resolve the above problems, providing secondary batteries having a high voltage, high capacity and high rate characteristics. In addition, the inventors have discovered that it is possible to obtain derivatives in which the nitrogens on the pyridines that form the fused-ring structure have been quaternized, and that, as a result, an even higher voltage is achieved and dissolution in the electrolyte solution is suppressed, providing a high-performance secondary battery that exhibits high cycle characteristics.

Accordingly, in a first aspect, the invention provides a charge storage material comprising a dipyridine-fused benzoquinone of formula (1) below or a derivative thereof

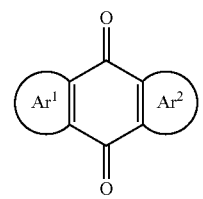

(1)

wherein $Ar^1$ and $Ar^2$ are each independently a pyridine ring that forms together with two carbon atoms on a benzoquinone skeleton, or a derivative thereof.

In a preferred embodiment of this charge storage material, the dipyridine-fused benzoquinone or derivative thereof has formula (1-1), (1-2) or (1-3) below (1-1)

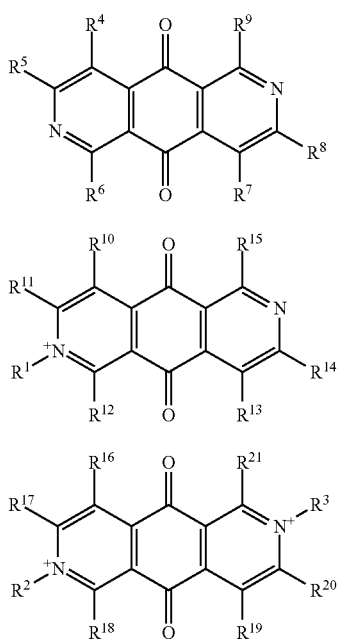

(1-2)

(1-3)

wherein R$^1$ to R$^3$ are each independently an alkyl group of 1 to 12 carbon atoms, a propargyl group, methylstyrene or norbornene; and R$^4$ to R$^{21}$ are each independently a hydrogen atom, a halogen atom, a hydroxyl group, a mercapto group, an amino group, a substituted or unsubstituted alkyl group of 1 to 12 carbon atoms, a substituted or unsubstituted alkenyl group of 2 to 12 carbon atoms, a substituted or unsubstituted alkynyl group of 2 to 12 carbon atoms, a substituted or unsubstituted aryl group of 6 to 12 carbon atoms, a substituted or unsubstituted heteroaryl group of 3 to 12 carbon atoms, a substituted or unsubstituted alkoxy group of 1 to 12 carbon atoms, a substituted or unsubstituted alkylthio group of 1 to 12 carbon atoms, a substituted or unsubstituted monoalkylamino group of 1 to 12 carbon atoms, a dialkylamino group in which each alkyl group is independently a substituted or unsubstituted alkyl group of 1 to 12 carbon atoms, an alkylcarbonyl group of 2 to 12 carbon atoms, a nitro group, a cyano group, a sulfonic acid group, a phosphonic acid group, a carboxyl group, an aminocarbonyl group, or an alkylaminocarbonyl group of 2 to 12 carbon atoms.

In a second aspect, the invention provides a charge storage material comprising a dipyridine-fused benzoquinone skeleton-containing polymer which includes recurring units of formula (2) and/or (3) below (2)

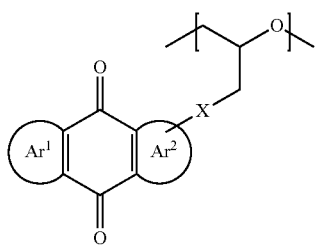

(3)

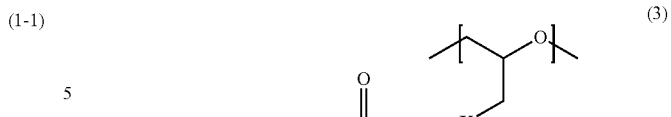

wherein Ar$^1$ and Ar$^2$ are each independently a pyridine ring that forms together with two carbon atoms on a benzoquinone skeleton, or a derivative thereof; and each X is independently a single bond or a divalent group.

In a preferred embodiment of the charge storage material according to the second aspect of the invention, the dipyridine-fused benzoquinone skeleton-containing polymer includes recurring units of formula (2-1), (2-2) or (3-1) below (2-1)

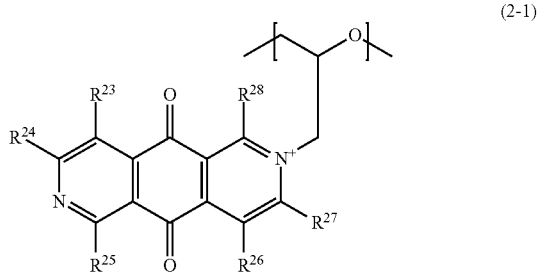

(2-2)

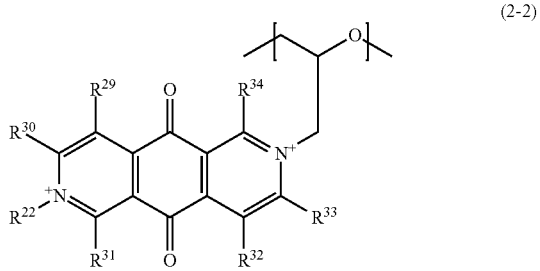

(3-1)

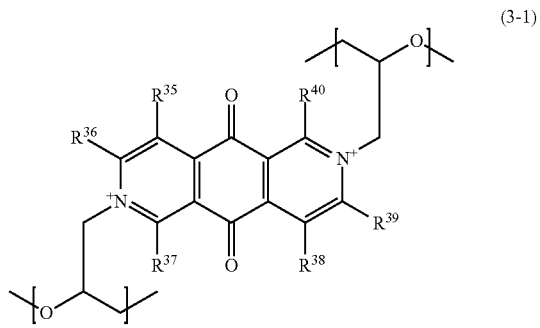

wherein R$^{22}$ is an alkyl group of 1 to 12 carbon atoms, a propargyl group, norbornene or methylstyrene; and R$^{23}$ to R$^{40}$ are each independently a hydrogen atom, a halogen atom, a hydroxyl group, a mercapto group, an amino group, a substituted or unsubstituted alkyl group of 1 to 12 carbon atoms, a substituted or unsubstituted alkenyl group of 2 to 12 carbon atoms, a substituted or unsubstituted alkynyl group of 2 to 12 carbon atoms, a substituted or unsubstituted aryl group of 6 to 12 carbon atoms, a substituted or unsubstituted heteroaryl group of 3 to 12 carbon atoms, a substituted or unsubstituted alkoxy group of 1 to 12 carbon atoms, a substituted or unsubstituted alkylthio group of 1 to 12 carbon atoms, a substituted or unsubstituted monoalkylamino group of 1 to 12 carbon atoms, a dialkylamino group in which each alkyl group is independently a substituted or unsubstituted alkyl group of 1 to 12 carbon atoms, an alkylcarbonyl group of 2 to 12 carbon atoms, a nitro group, a cyano group, a sulfonic acid group, a phosphonic acid group, a carboxyl group, an aminocarbonyl group, or an alkylaminocarbonyl group of 2 to 12 carbon atoms.

In a third aspect, the invention provides a charge storage material comprising a dipyridine-fused benzoquinone of formula (4) below or a derivative thereof

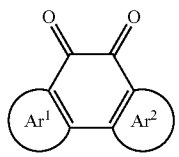

(4)

wherein $Ar^1$ and $Ar^2$ are each independently a pyridine ring that forms together with two carbon atoms on the benzoquinone skeleton, or a derivative thereof.

In a preferred embodiment of the charge storage material according to the third aspect of the invention, the dipyridine-fused benzoquinone or derivative thereof has formula (4-1), (4-2) or (4-3) below

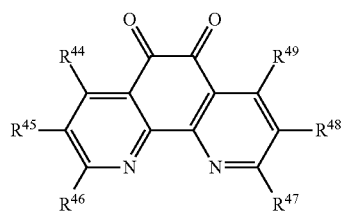

(4-1)

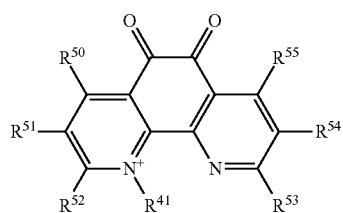

(4-2)

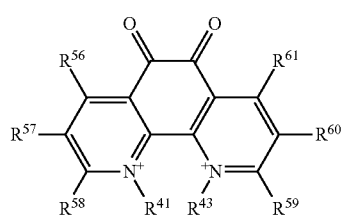

(4-3)

wherein $R^{41}$ to $R^{43}$ are each independently an alkyl group of 1 to 12 carbon atoms, a propargyl group, methylstyrene or norbornene; and $R^{44}$ to $R^{61}$ are each independently a hydrogen atom, a halogen atom, a hydroxyl group, a mercapto group, an amino group, a substituted or unsubstituted alkyl group of 1 to 12 carbon atoms, a substituted or unsubstituted alkenyl group of 2 to 12 carbon atoms, a substituted or unsubstituted alkynyl group of 2 to 12 carbon atoms, a substituted or unsubstituted aryl group of 6 to 12 carbon atoms, a substituted or unsubstituted heteroaryl group of 3 to 12 carbon atoms, a substituted or unsubstituted alkoxy group of 1 to 12 carbon atoms, a substituted or unsubstituted alkylthio group of 1 to 12 carbon atoms, a substituted or unsubstituted monoalkylamino group of 1 to 12 carbon atoms, a dialkylamino group in which each alkyl group is independently a substituted or unsubstituted alkyl group of 1 to 12 carbon atoms, an alkylcarbonyl group of 2 to 12 carbon atoms, a nitro group, a cyano group, a sulfonic acid group, a phosphonic acid group, a carboxyl group, an aminocarbonyl group, or an alkylaminocarbonyl group of 2 to 12 carbon atoms.

In a fourth aspect, the invention provides a charge storage material comprising a dipyridine-fused benzoquinone skeleton-containing polymer which includes recurring units of formula (5) and/or (6) below

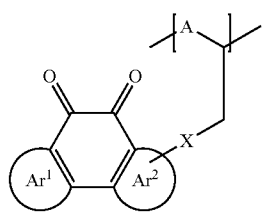

(5)

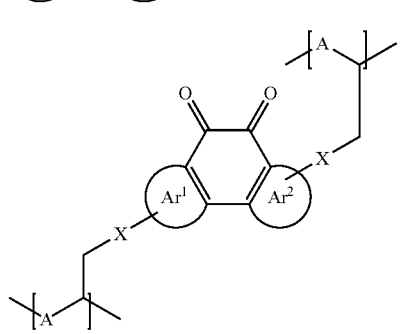

(6)

wherein $Ar^1$ and $Ar^2$ are each independently a pyridine ring that forms together with two carbon atoms on the benzoquinone skeleton, or a derivative thereof; each X is independently a single bond or a divalent group; and each A is independently —OCH$_2$— or —CH$_2$—.

In a preferred embodiment of the charge storage material according to the fourth aspect of the invention, the dipyridine-fused benzoquinone skeleton-containing polymer includes recurring units of formula (5-1) and/or (6-1) below

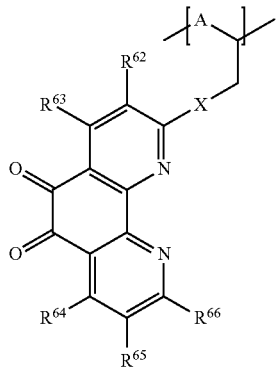

(5-1)

(6-1)

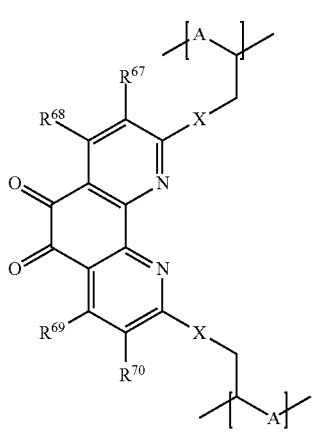

wherein X and A are as defined above; and $R^{62}$ to $R^{70}$ are each independently a hydrogen atom, a halogen atom, a hydroxyl group, a mercapto group, an amino group, a substituted or unsubstituted alkyl group of 1 to 12 carbon atoms, a substituted or unsubstituted alkenyl group of 2 to 12 carbon atoms, a substituted or unsubstituted alkynyl group of 2 to 12 carbon atoms, a substituted or unsubstituted aryl group of 6 to 12 carbon atoms, a substituted or unsubstituted heteroaryl group of 3 to 12 carbon atoms, a substituted or unsubstituted alkoxy group of 1 to 12 carbon atoms, a substituted or unsubstituted alkylthio group of 1 to 12 carbon atoms, a substituted or unsubstituted monoalkylamino group of 1 to 12 carbon atoms, a dialkylamino group in which each alkyl group is independently a substituted or unsubstituted alkyl group of 1 to 12 carbon atoms, an alkylcarbonyl group of 2 to 12 carbon atoms, a nitro group, a cyano group, a sulfonic acid group, a phosphonic acid group, a carboxyl group, an aminocarbonyl group, or an alkylaminocarbonyl group of 2 to 12 carbon atoms.

In a fifth aspect, the invention provides a charge storage material comprising a dipyridine-fused benzoquinone skeleton-containing polymer which includes recurring units of formula (7) below (7)

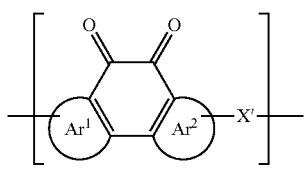

wherein $Ar^1$ and $Ar^2$ are each independently a pyridine ring that forms together with two carbon atoms on the benzoquinone skeleton, or a derivative thereof; and each X' is independently a single bond or a divalent group.

In a preferred embodiment of the charge storage material according to the fifth aspect of the invention, the dipyridine-fused benzoquinone skeleton-containing polymer includes recurring units of formula (7-1) below (7-1)

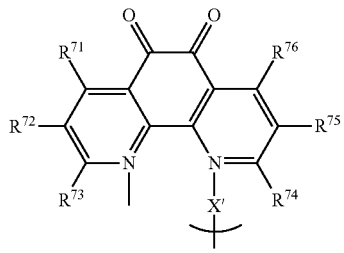

wherein X' is as defined above; and $R^{71}$ to $R^{76}$ are each independently a hydrogen atom, a halogen atom, a hydroxyl group, a mercapto group, an amino group, a substituted or unsubstituted alkyl group of 1 to 12 carbon atoms, a substituted or unsubstituted alkenyl group of 2 to 12 carbon atoms, a substituted or unsubstituted alkynyl group of 2 to 12 carbon atoms, a substituted or unsubstituted aryl group of 6 to 12 carbon atoms, a substituted or unsubstituted heteroaryl group of 3 to 12 carbon atoms, a substituted or unsubstituted alkoxy group of 1 to 12 carbon atoms, a substituted or unsubstituted alkylthio group of 1 to 12 carbon atoms, a substituted or unsubstituted monoalkylamino group of 1 to 12 carbon atoms, a dialkylamino group in which each alkyl group is independently a substituted or unsubstituted alkyl group of 1 to 12 carbon atoms, an alkylcarbonyl group of 2 to 12 carbon atoms, a nitro group, a cyano group, a sulfonic acid group, a phosphonic acid group, a carboxyl group, an aminocarbonyl group, or an alkylaminocarbonyl group of 2 to 12 carbon atoms.

In another aspect, the invention provides an electrode active material which includes the charge storage material according to the first, second, third, fourth or fifth aspect of the invention.

In yet another aspect, the invention provides an electrode slurry which includes this electrode active material and a solvent.

In still another aspect, the invention provides a thin-film which includes this electrode active material.

In a further aspect, the invention provides a thin-film produced from the foregoing electrode slurry.

In a still further aspect, the invention provides an electrode which includes the foregoing electrode active material.

In an additional aspect, the invention provides an electrode which includes either of the foregoing thin-films.

In another aspect, the invention provides a secondary battery which includes either of the foregoing electrodes.

In yet another aspect, the invention provides a lithium ion battery which includes either of the foregoing electrodes.

In a further aspect, the invention provides an air battery which includes either of the foregoing electrodes.

In a still further aspect, the invention provides a dipyridine-fused benzoquinone of formula (1) below or a derivative thereof (1)

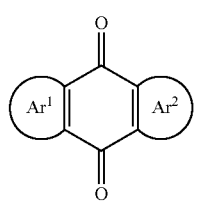

wherein Ar¹ and Ar² are each independently a pyridine ring that forms together with two carbon atoms on a benzoquinone skeleton, or a derivative thereof.

In a yet further aspect, the invention provides a dipyridine-fused benzoquinone skeleton-containing polymer which includes recurring units of formula (2) and/or (3) below

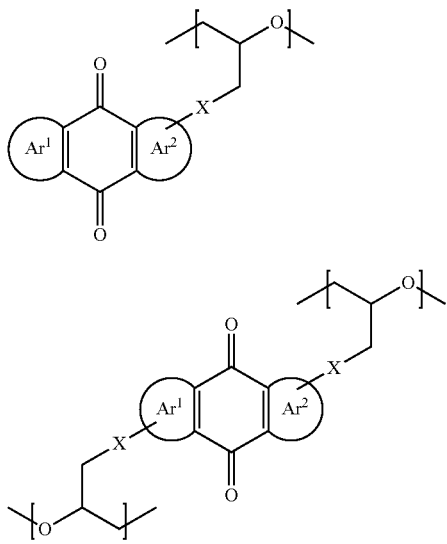

wherein Ar¹ and Ar² are each independently a pyridine ring that forms together with two carbon atoms on the benzoquinone skeleton, or a derivative thereof; and each X is independently a single bond or a divalent group.

In another aspect, the invention provides a dipyridine-fused benzoquinone of formula (4) below or a derivative thereof

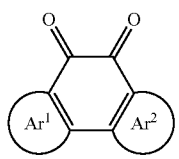

wherein Ar¹ and Ar² are each independently a pyridine ring that forms together with two carbon atoms on a benzoquinone skeleton, or a derivative thereof.

In a further aspect, the invention provides a dipyridine-fused benzoquinone skeleton-containing polymer which includes recurring units of formula (5) and/or (6) below

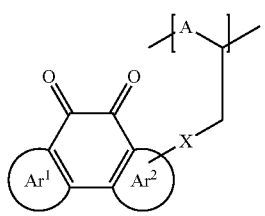

wherein Ar¹ and Ar² are each independently a pyridine ring that forms together with two carbon atoms on the benzoquinone skeleton, or a derivative thereof; each X is independently a single bond or a divalent group; and each A is independently —OCH₂— or —CH₂—.

In a still further aspect, the invention provides a dipyridine-fused benzoquinone skeleton-containing polymer which includes recurring units of formula (7) below

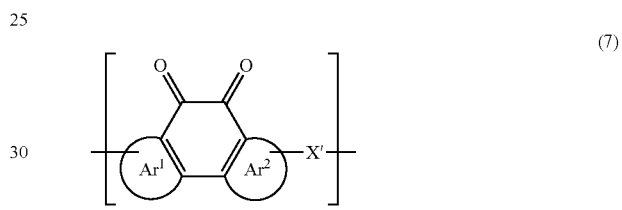

wherein Ar¹ and Ar² are each independently a pyridine ring that forms together with two carbon atoms on the benzoquinone skeleton, or a derivative thereof; and each X' is independently a single bond or a divalent group.

Advantageous Effects of the Invention

Because the foregoing dipyridine-fused benzoquinones and derivatives thereof and the foregoing dipyridine-fused benzoquinone skeleton-containing polymers have a dipyridine-fused benzoquinone skeleton that stores charge and are stabilized by a pyridine fused-ring structure where two anion radicals form, they have a high electrochemical stability and are thus useful as charge storage materials. Moreover, given that two-electron reduction proceeds, forming a stable dianion, when such charge storage materials are used as electrode active materials in batteries, high stability and high capacity are both achieved.

In addition, the pyridine rings can be derivatized by bond formation with carbon, and are capable of being rendered into quaternary pyridinium salts. This causes the potential to shift to the noble side, enabling a higher voltage to be achieved when such charge storage materials are used as positive electrode active materials in secondary batteries. Also, dipyridine-fused benzoquinones and derivatives thereof can be reacted with other polymers to form polymers having dipyridine-fused benzoquinones or derivatives thereof grafted thereon. It is possible in this way to manifest suitable levels of resistance to dissolution in the electrolyte solution, swellability, ionic conductivity, and bondability with inorganic electrode active materials and current collectors.

Owing to these effects, by using the foregoing dipyridine-fused benzoquinones or derivatives thereof, or the foregoing dipyridine-fused benzoquinone skeleton-containing polymers, as electrode active materials, it is possible to manufacture secondary batteries having high rate characteristics, a high capacity and high cycle characteristics. The dipyridine-fused benzoquinones and derivatives thereof and the dipyridine-fused benzoquinone skeleton-containing polymers are particularly suitable as electrode active materials for lithium ion batteries. In ordinary secondary batteries, an inorganic material or a carbon material is used as the electrode active material. It is possible to replace either the positive electrode or the negative electrode in such batteries with an electrode containing one of the charge storage materials of the invention, or to use one of the charge storage materials of the invention in combination with an electrode active material that is made of an inorganic material or a carbon material.

BRIEF DESCRIPTION OF THE DIAGRAMS

Figure 5:
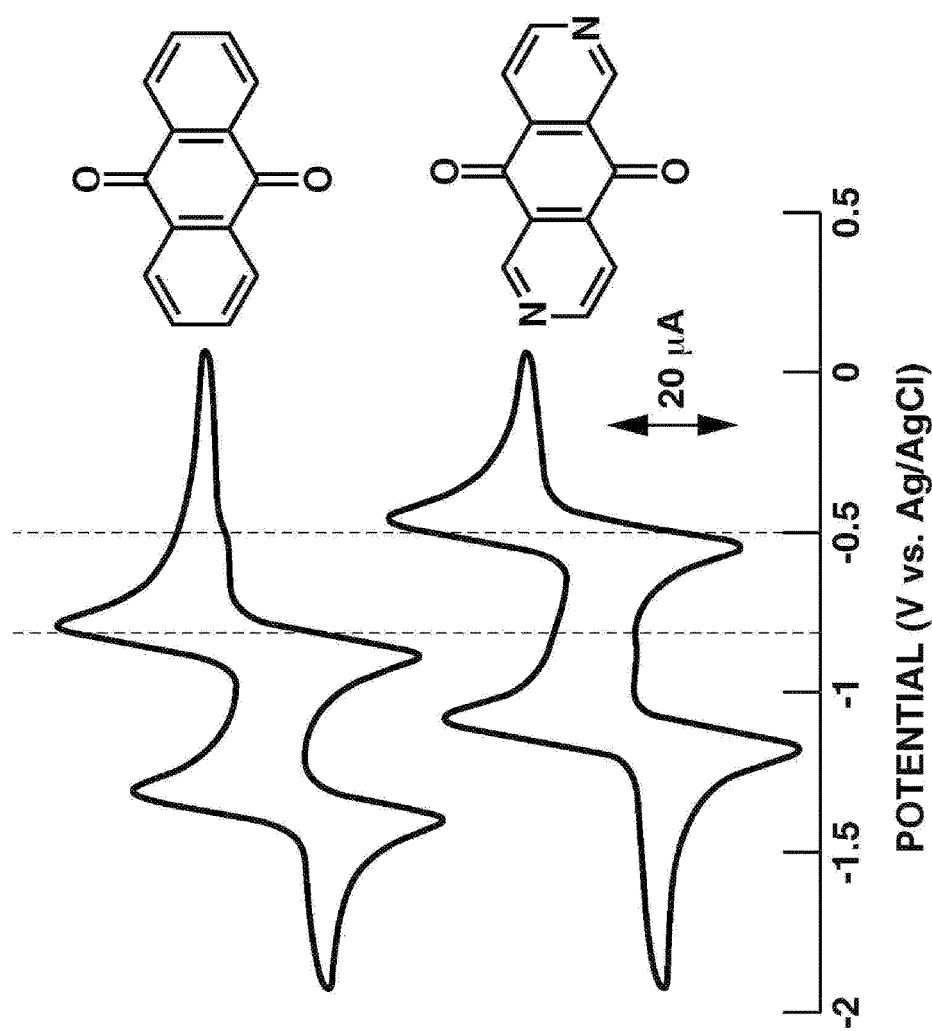

FIG. 5 presents cyclic voltammograms of an anthraquinone solution and a dipyridine-fused benzoquinone solution.

Figure 6:
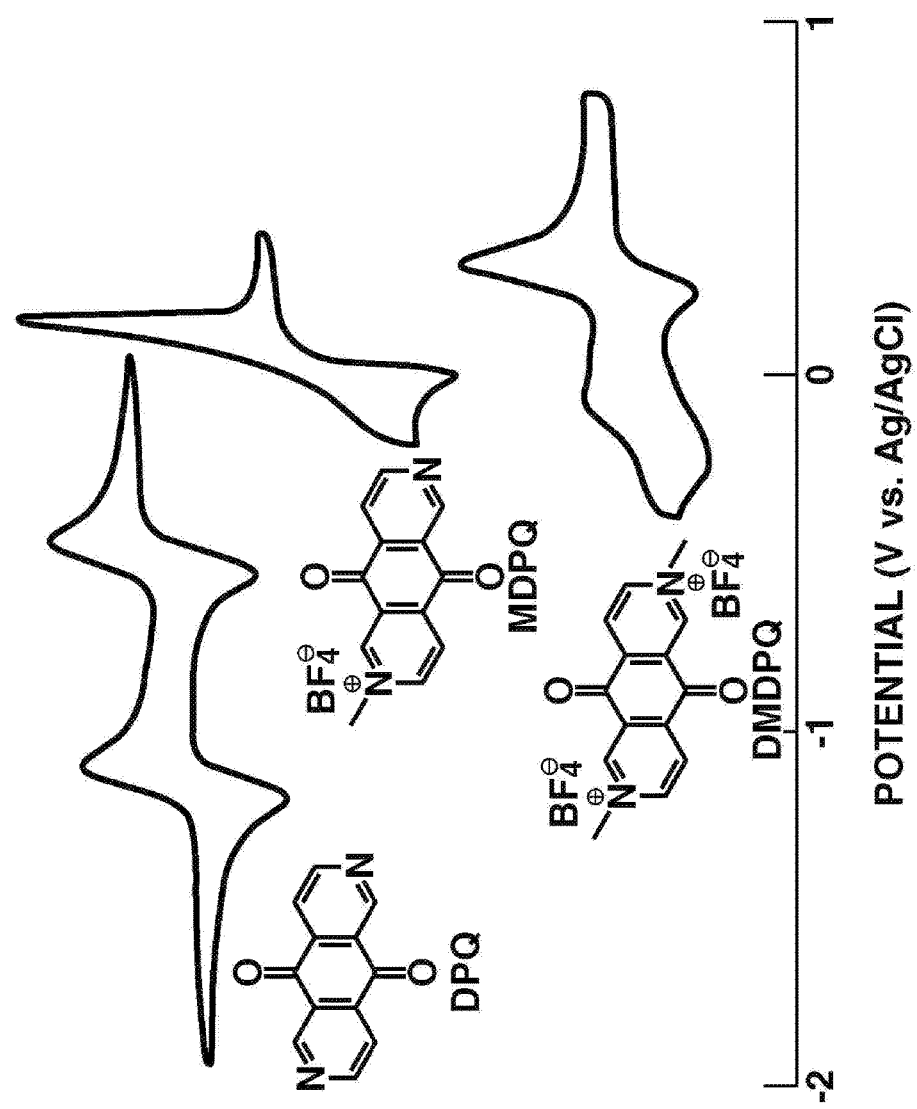

FIG. 6 presents cyclic voltammograms of a dipyridine-fused benzoquinone solution, a solution of Dipyridine-Fused Benzoquinone Derivative C, and a solution of Dipyridine-Fused Benzoquinone Derivative D.

Figure 7:
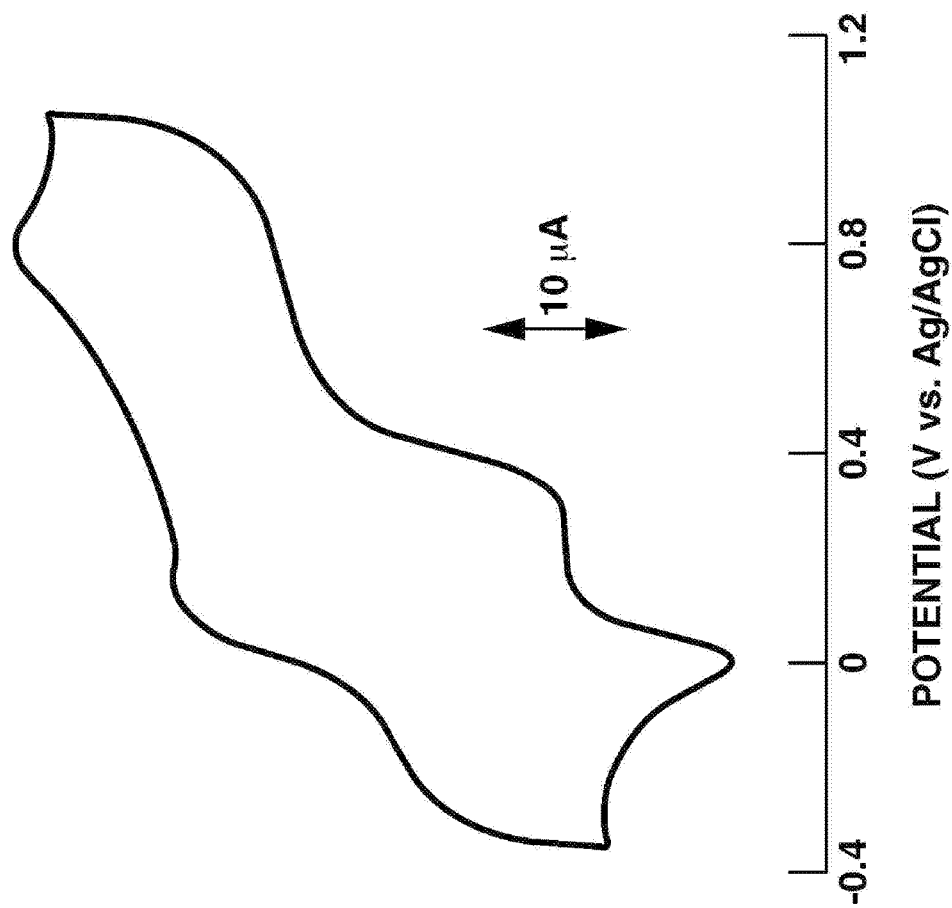

FIG. 7 is a cyclic voltammogram of a solution of Dipyridine-Fused Benzoquinone Derivative E.

Figure 8:
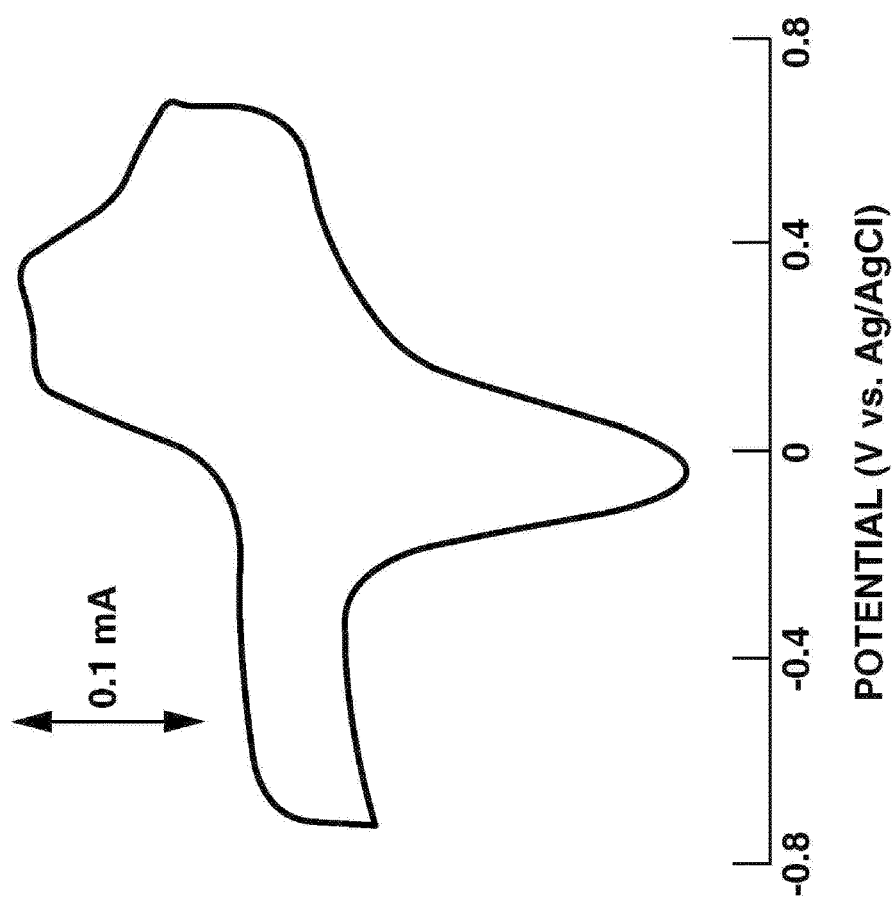

FIG. 8 is a cyclic voltammogram of the carbon composite electrode produced in Example 16.

Figure 9:
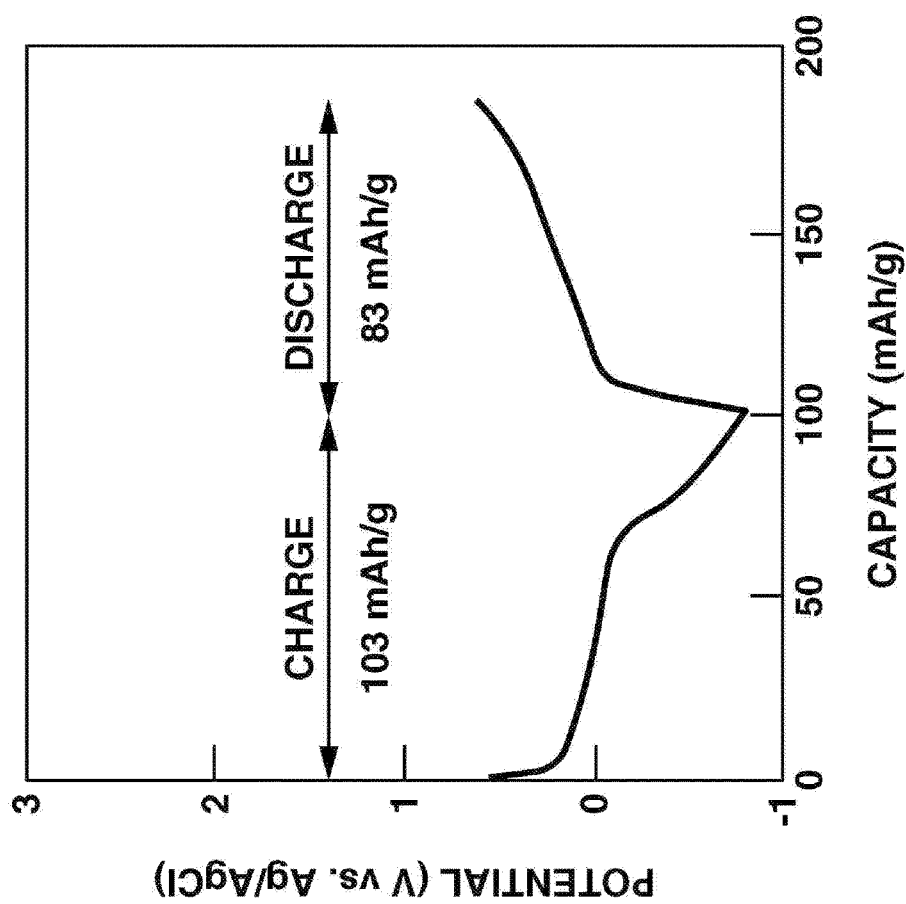

FIG. 9 is a graph showing the results of measurements of the potential difference with a reference electrode when the charge-discharge capacity was varied in the half-cell produced in Example 16.

Figure 10:
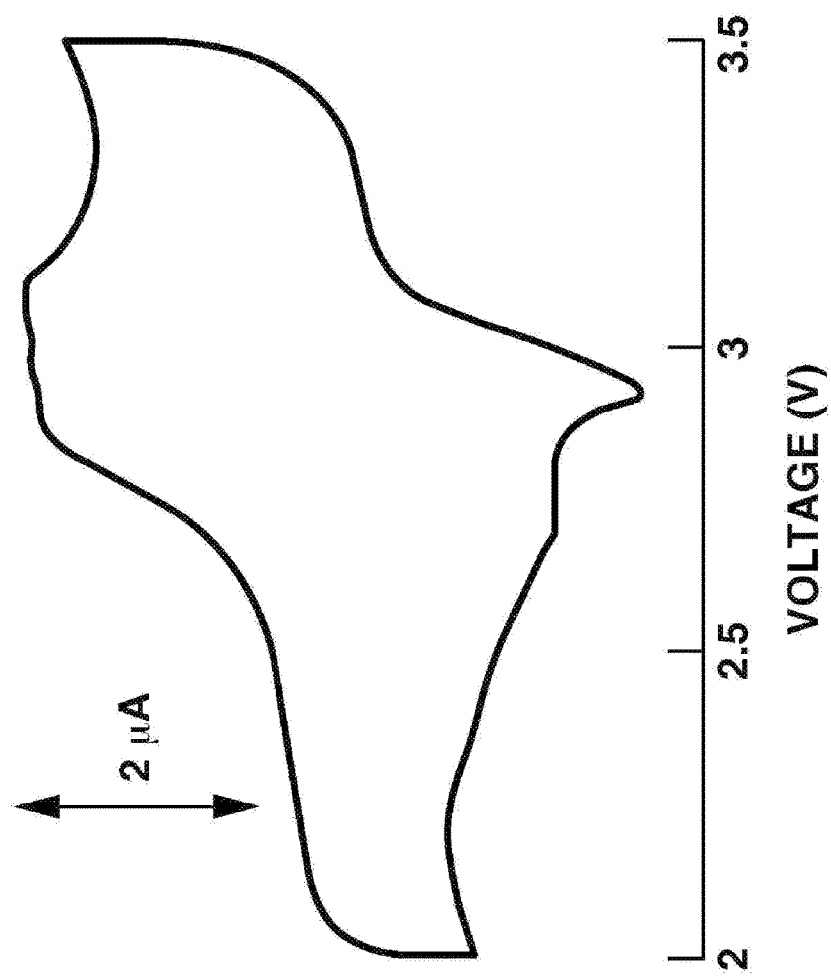

FIG. 10 is a cyclic voltammogram of the carbon composite electrode produced in Example 17.

Figure 11:
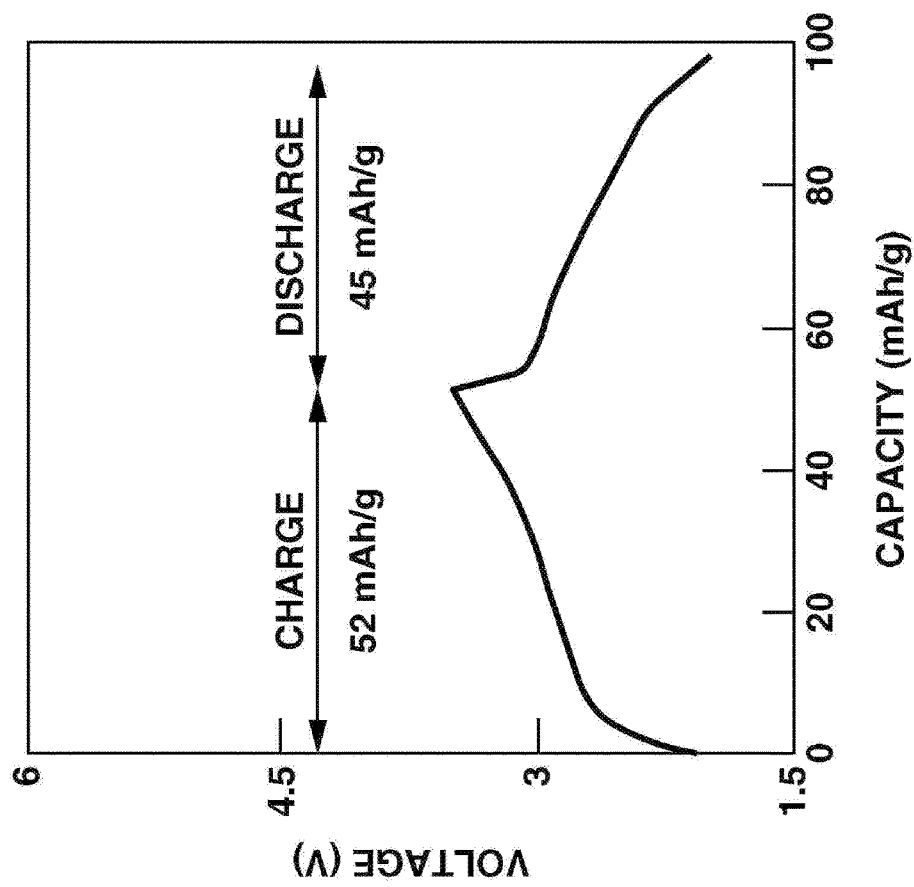

FIG. 11 is a graph showing the results of measurements of the potential difference with a reference electrode when the charge-discharge capacity was varied in the lithium ion battery produced in Example 17.

Figure 12:
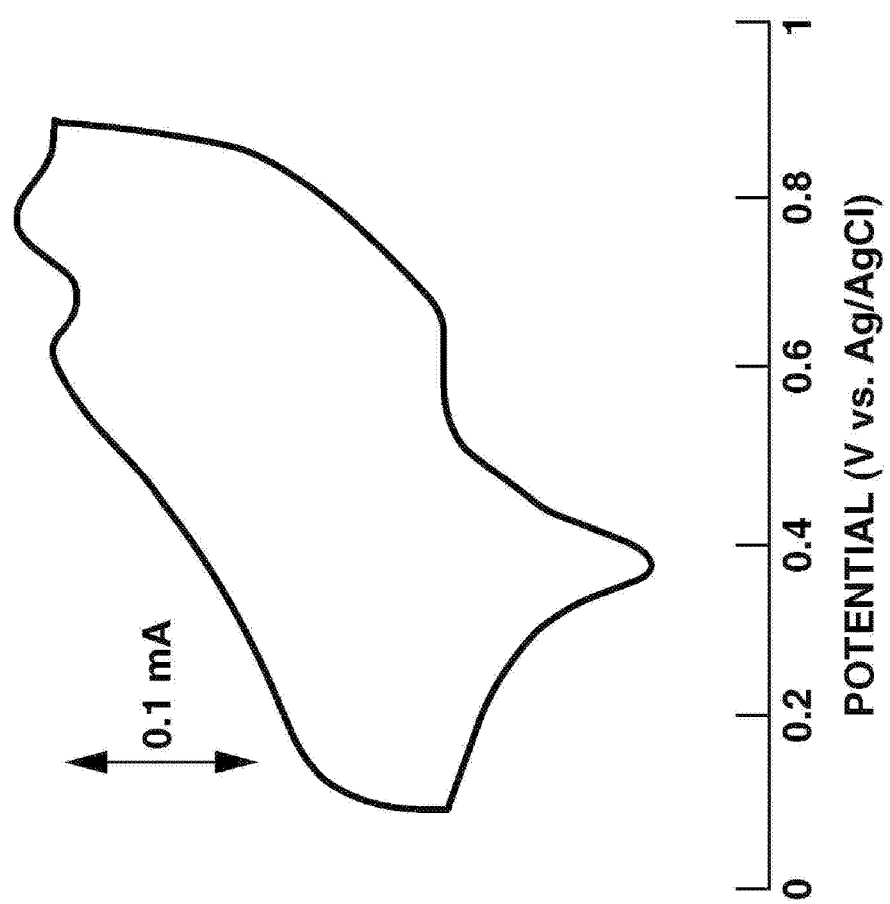

FIG. 12 is a cyclic voltammogram of the carbon composite electrode produced in Example 18.

Figure 13:
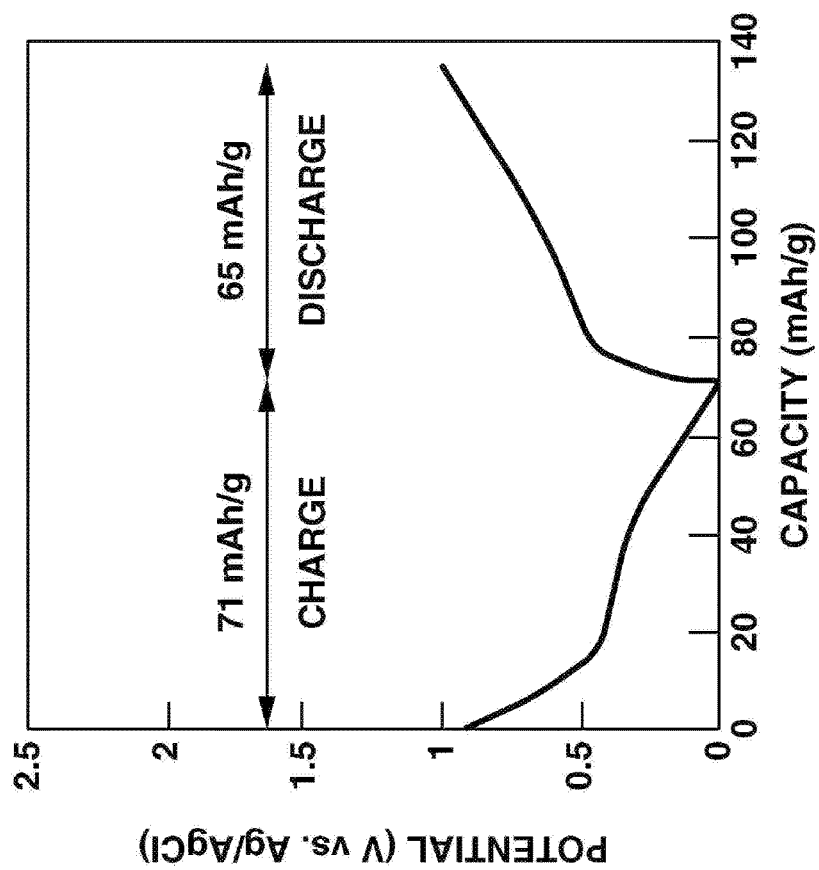

FIG. 13 is a graph showing the results of measurements of the potential difference with a reference electrode when the charge-discharge capacity was varied in the half-cell produced in Example 18.

DETAILED DESCRIPTION OF THE INVENTION

The objects, features and advantages of the invention will become more apparent from the following detailed description, taken in conjunction with the foregoing diagrams.

Charge Storage Material

The charge storage material according to the first aspect of the invention is made of a dipyridine-fused benzoquinone of formula (1) below or a derivative thereof. As used herein, "charge storage material" refers to a material that is capable of storing an electrical charge. Such a material is useful as, for example an electrode active material in secondary batteries.

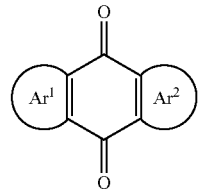
(1)

In formula (1), $Ar^1$ and $Ar^2$ are each independently a pyridine ring that forms together with two carbon atoms on a benzoquinone skeleton, or a derivative thereof.

This dipyridine-fused benzoquinone or derivative thereof is preferably one of formula (1-1), (1-2) or (1-3) below.

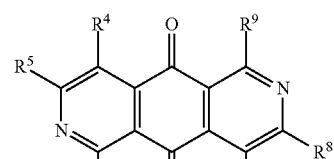
(1-1)

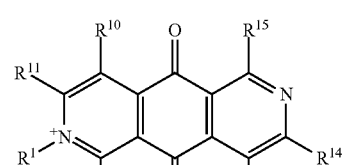
(1-2)

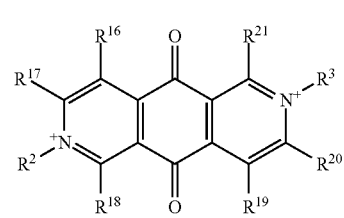
(1-3)

Here, $R^1$ to $R^3$ are each independently an alkyl group of 1 to 12 carbon atoms, a propargyl group, methylstyrene, or norbornene. $R^4$ to $R^{21}$ are each independently a hydrogen atom, a halogen atom, a hydroxyl group, a mercapto group, an amino group, a substituted or unsubstituted alkyl group of 1 to 12 carbon atoms, a substituted or unsubstituted alkenyl group of 2 to 12 carbon atoms, a substituted or unsubstituted alkynyl group of 2 to 12 carbon atoms, a substituted or unsubstituted aryl group of 6 to 12 carbon atoms, a substituted or unsubstituted heteroaryl group of 3 to 12 carbon atoms, a substituted or unsubstituted alkoxy group of 1 to 12 carbon atoms, a substituted or unsubstituted alkylthio group of 1 to 12 carbon atoms, a substituted or unsubstituted monoalkylamino group of 1 to 12 carbon atoms, a dialkylamino group in which each alkyl group is independently a substituted or unsubstituted alkyl group of 1 to 12 carbon atoms, an alkylcarbonyl group of 2 to 12 carbon atoms, a nitro group, a cyano group, a sulfonic acid group, a phosphonic acid group, a carboxyl group, an aminocarbonyl group, or an alkylaminocarbonyl group of 2 to 12 carbon atoms.

The charge storage material according to the second aspect of the invention is made of a dipyridine-fused benzoquinone skeleton-containing polymer which includes recurring units of formula (2) and/or (3) below.

or all of the hydrogen atoms bonded to the carbon atoms on these groups may be substituted with any monovalent groups.

This dipyridine-fused benzoquinone skeleton-containing polymer preferably includes recurring units of formula (2-1), (2-2) or (3-1) below.

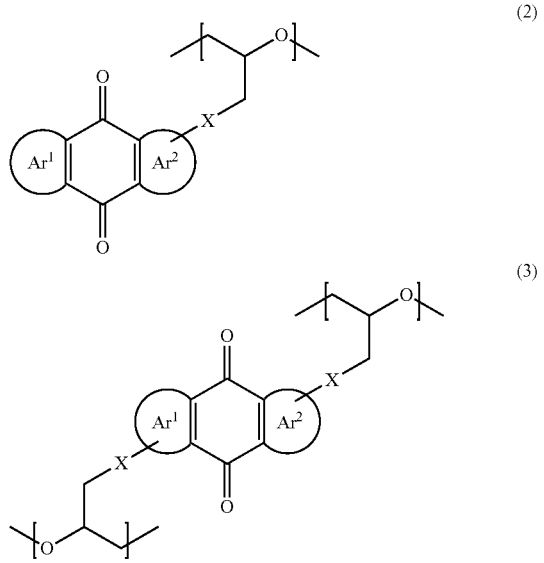

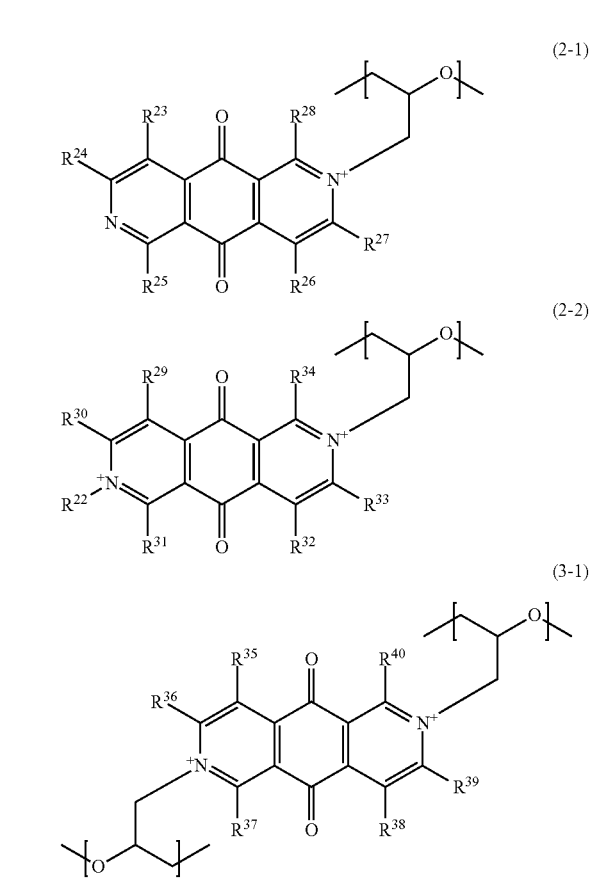

Here, $Ar^1$ and $Ar^2$ are as defined above, and each X is independently a single bond or a divalent group. Of these, X is preferably a single bond to the nitrogen atom on a pyridine ring.

Examples of the divalent group include alkylene groups of 1 to 12 carbon atoms, alkyleneoxy groups of 1 to 12 carbon atoms, alkylenethio groups of 1 to 12 carbon atoms, alkyleneamino groups of 1 to 12 carbon atoms, dialkylene ether groups of 2 to 12 carbon atoms, dialkylene thioether groups of 2 to 12 carbon atoms, dialkyleneamino groups of 2 to 12 carbon atoms, alkylenedioxy groups of 1 to 12 carbon atoms, alkylenedithio groups of 1 to 12 carbon atoms, alkylenediamino groups of 1 to 12 carbon atoms, —C(=O)—O—, —O—C(=O)—, —NH—C(=O)—, —C(=O)—NH—, alkyleneaminocarbonyl groups of 2 to 12 carbon atoms, alkyleneoxycarbonyl groups of 2 to 12 carbon atoms, alkylenethiocarbonyl groups of 2 to 12 carbon atoms, alkyleneaminocarbonyl groups of 2 to 12 carbon atoms, alkylenecarbonyl groups of 2 to 12 carbon atoms, oxyalkylenecarbonyl groups of 2 to 12 carbon atoms, thioalkylenecarbonyl groups of 2 to 12 carbon atoms, aminoalkylenecarbonyl groups of 2 to 12 carbon atoms, arylene groups of 6 to 20 carbon atoms, aryleneoxy groups of 6 to 20 carbon atoms, arylenethio groups of 6 to 20 carbon atoms, aryleneamino groups of 6 to 20 carbon atoms, diarylene ether groups of 6 to 20 carbon atoms, diarylene thioether groups of 6 to 20 carbon atoms, diaryleneamino groups of 6 to 20 carbon atoms, arylenedioxy groups of 6 to 20 carbon atoms, arylenedithio groups of 6 to 20 carbon atoms, arylenediamino groups of 6 to 20 carbon atoms, aryleneaminocarbonyl groups of 6 to 20 carbon atoms, aryleneoxycarbonyl groups of 6 to 20 carbon atoms, arylenethiocarbonyl groups of 6 to 20 carbon atoms, aryleneaminocarbonyl groups of 6 to 20 carbon atoms, arylenecarbonyl groups of 6 to 20 carbon atoms, oxyarylenecarbonyl groups of 6 to 20 carbon atoms, thioarylenecarbonyl groups of 6 to 20 carbon atoms, aminoarylenecarbonyl groups of 6 to 20 carbon atoms, and combinations of these groups. Some Here, $R^{22}$ is an alkyl group of 1 to 12 carbon atoms, a propargyl group, norbornene or methylstyrene. $R^{23}$ to $R^{40}$ are each independently a hydrogen atom, a halogen atom, a hydroxyl group, a mercapto group, an amino group, a substituted or unsubstituted alkyl group of 1 to 12 carbon atoms, a substituted or unsubstituted alkenyl group of 2 to 12 carbon atoms, a substituted or unsubstituted alkynyl group of 2 to 12 carbon atoms, a substituted or unsubstituted aryl group of 6 to 12 carbon atoms, a substituted or unsubstituted heteroaryl group of 3 to 12 carbon atoms, a substituted or unsubstituted alkoxy group of 1 to 12 carbon atoms, a substituted or unsubstituted alkylthio group of 1 to 12 carbon atoms, a substituted or unsubstituted monoalkylamino group of 1 to 12 carbon atoms, a dialkylamino group in which each alkyl group is independently a substituted or unsubstituted alkyl group of 1 to 12 carbon atoms, an alkylcarbonyl group of 2 to 12 carbon atoms, or an alkylaminocarbonyl group of 2 to 12 carbon atoms.

In this dipyridine-fused benzoquinone skeleton-containing polymer, the content of recurring units of formula (2) and/or (3) is preferably from 10 to 100 mol %, more preferably from 50 to 100 mol %, and even more preferably from 80 to 100 mol %, of all the recurring units.

The charge storage material according to the third aspect of the invention is made of a dipyridine-fused benzoquinone of formula (4) below or a derivative thereof

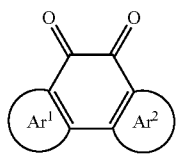
(4)

wherein Ar¹ and Ar² are as defined above.

This dipyridine-fused benzoquinone or derivative thereof is preferably one of formula (4-1), (4-2) or (4-3) below.

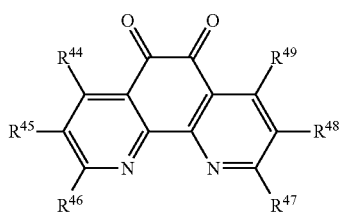
(4-1)

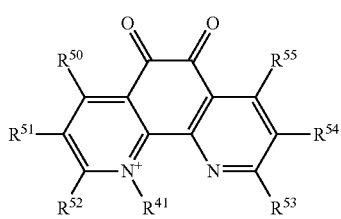
(4-2)

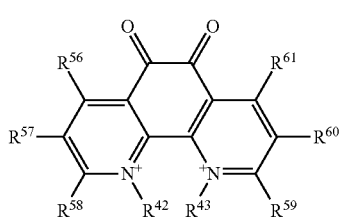
(4-3)

Here, $R^{41}$ to $R^{43}$ are each independently an alkyl group of 1 to 12 carbon atoms, a propargyl group, methylstyrene or norbornene. $R^{44}$ to $R^{61}$ are each independently a hydrogen atom, a halogen atom, a hydroxyl group, a mercapto group, an amino group, a substituted or unsubstituted alkyl group of 1 to 12 carbon atoms, a substituted or unsubstituted alkenyl group of 2 to 12 carbon atoms, a substituted or unsubstituted alkynyl group of 2 to 12 carbon atoms, a substituted or unsubstituted aryl group of 6 to 12 carbon atoms, a substituted or unsubstituted heteroaryl group of 3 to 12 carbon atoms, a substituted or unsubstituted alkoxy group of 1 to 12 carbon atoms, a substituted or unsubstituted alkylthio group of 1 to 12 carbon atoms, a substituted or unsubstituted monoalkylamino group of 1 to 12 carbon atoms, a dialkylamino group in which each alkyl group is independently a substituted or unsubstituted alkyl group of 1 to 12 carbon atoms, an alkylcarbonyl group of 2 to 12 carbon atoms, a nitro group, a cyano group, a sulfonic acid group, a phosphonic acid group, a carboxyl group, an aminocarbonyl group, or an alkylaminocarbonyl group of 2 to 12 carbon atoms.

The charge storage material according to the fourth aspect of the invention is made of a dipyridine-fused benzoquinone skeleton-containing polymer which includes recurring units of formula (5) and/or (6) below.

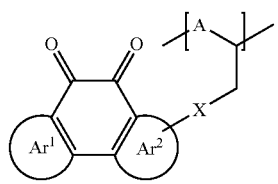
(5)

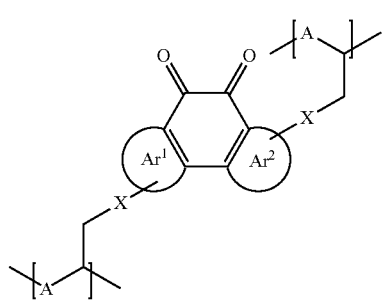
(6)

Here, Ar¹, Ar² and X are as defined above, with X being preferably a divalent group that is bonded to a carbon atom on a pyridine ring. A is each independently —OCH₂— or —CH₂—.

This dipyridine-fused benzoquinone skeleton-containing polymer preferably includes recurring units of formula (5-1) and/or (6-1) below.

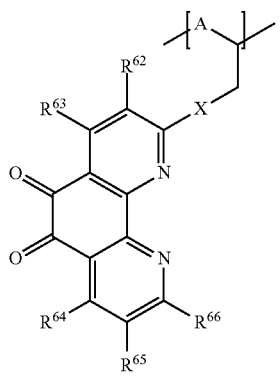
(5-1)

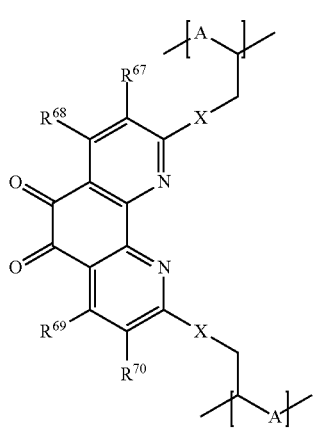
(6-1)

Here, X and A are as defined above. $R^{62}$ to $R^{70}$ are each independently a hydrogen atom, a halogen atom, a hydroxyl group, a mercapto group, an amino group, a substituted or unsubstituted alkyl group of 1 to 12 carbon atoms, a substituted or unsubstituted alkenyl group of 2 to 12 carbon atoms, a substituted or unsubstituted alkynyl group of 2 to 12 carbon atoms, a substituted or unsubstituted aryl group of 6 to 12 carbon atoms, a substituted or unsubstituted heteroaryl group of 3 to 12 carbon atoms, a substituted or unsubstituted alkoxy group of 1 to 12 carbon atoms, a substituted or unsubstituted alkylthio group of 1 to 12 carbon atoms, a substituted or unsubstituted monoalkylamino group of 1 to 12 carbon atoms, a dialkylamino group in which each alkyl group is independently a substituted or unsubstituted alkyl group of 1 to 12 carbon atoms, an alkylcarbonyl group of 2 to 12 carbon atoms, a nitro group, a cyano group, a sulfonic acid group, a phosphonic acid group, a carboxyl group, an aminocarbonyl group or an alkylaminocarbonyl group of 2 to 12 carbon atoms.

In this dipyridine-fused benzoquinone skeleton-containing polymer, the content of recurring units of formula (5) and/or (6) is preferably from 10 to 100 mol %, more preferably from 50 to 100 mol %, and even more preferably from 80 to 100 mol %, of all the recurring units.

The charge storage material according to the fifth aspect of the invention is made of a dipyridine-fused benzoquinone skeleton-containing polymer which includes recurring units of formula (7) below.

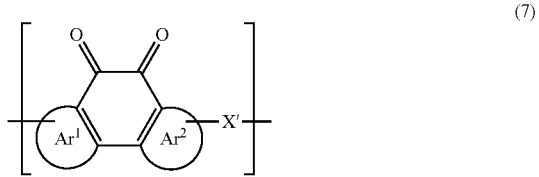

(7)

Here, $Ar^1$ and $Ar^2$ are as defined above, and X' is a single bond or a divalent group. The divalent group is exemplified in the same way as in the description above for X, and is preferably an alkylene group of 1 to 5 carbon atoms. Preferred examples of such alkylene groups include methylene, ethylene, trimethylene, propylene, tetramethylene and butylene groups. Also, X' is preferably bonded to the nitrogen atom on a pyridine ring.

This dipyridine-fused benzoquinone skeleton-containing polymer preferably includes recurring units of formula (7-1) below.

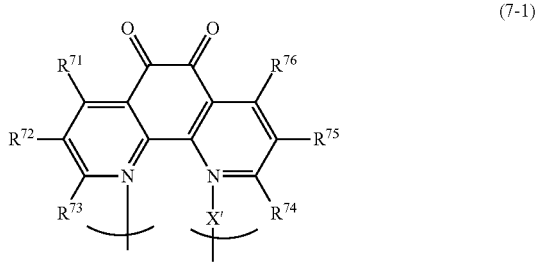

(7-1)

Here, X' is as defined above. $R^{71}$ to $R^{76}$ are each independently a hydrogen atom, a halogen atom, a hydroxyl group, a mercapto group, an amino group, a substituted or unsubstituted alkyl group of 1 to 12 carbon atoms, a substituted or unsubstituted alkenyl group of 2 to 12 carbon atoms, a substituted or unsubstituted alkynyl group of 2 to 12 carbon atoms, a substituted or unsubstituted aryl group of 6 to 12 carbon atoms, a substituted or unsubstituted heteroaryl group of 3 to 12 carbon atoms, a substituted or unsubstituted alkoxy group of 1 to 12 carbon atoms, a substituted or unsubstituted alkylthio group of 1 to 12 carbon atoms, a substituted or unsubstituted monoalkylamino group of 1 to 12 carbon atoms, a dialkylamino group in which each alkyl group is independently a substituted or unsubstituted alkyl group of 1 to 12 carbon atoms, an alkylcarbonyl group of 2 to 12 carbon atoms, a nitro group, a cyano group, a sulfonic acid group, a phosphonic acid group, a carboxyl group, an aminocarbonyl group. or an alkylaminocarbonyl group of 2 to 12 carbon atoms.

In this dipyridine-fused benzoquinone skeleton-containing polymer, the content of recurring units of formula (7) is preferably from 10 to 100 mol %, more preferably from 50 to 100 mol %, and even more preferably from 80 to 100 mol %, of all the recurring units.

The halogen atom is exemplified by a fluorine atom, a chlorine atom, a bromine atom and an iodine atom.

The alkyl group may be linear, branched or cyclic. Illustrative examples include methyl, ethyl, n-propyl, i-propyl, c-propyl, n-butyl, i-butyl, s-butyl, t-butyl, c-butyl, 1-methyl-c-propyl, 2-methyl-c-propyl, n-pentyl, 1-methyl-n-butyl, 2-methyl-n-butyl, 3-methyl-n-butyl, 1,1-dimethyl-n-propyl, 1,2-dimethyl-n-propyl, 2,2-dimethyl-n-propyl, 1-ethyl-n-propyl, c-pentyl, 1-methyl-c-butyl, 2-methyl-c-butyl, 3-methyl-c-butyl, 1,2-dimethyl-c-propyl, 2,2-dimethyl-c-propyl, 2,3-dimethyl-c-propyl, 1-ethyl-c-propyl, 2-ethyl-c-propyl, n-hexyl, 1-methyl-n-pentyl, 2-methyl-n-pentyl, 3-methyl-n-pentyl, 4-methyl-n-pentyl, 1,1-dimethyl-n-butyl, 1,2-dimethyl-n-butyl, 1,3-dimethyl-n-butyl, 2,2-dimethyl-n-butyl, 2,3-dimethyl-n-butyl, 3,3-dimethyl-n-butyl, 1-ethyl-n-butyl, 2-ethyl-n-butyl, 1,1,2-trimethyl-n-propyl, 1,2,2-trimethyl-n-propyl, 1-ethyl-1-methyl-n-propyl, 1-ethyl-2-methyl-n-propyl, c-hexyl, 1-methyl-c-pentyl, 2-methyl-c-pentyl, 3-methyl-c-pentyl, 1-ethyl-c-butyl, 2-ethyl-c-butyl, 3-ethyl-c-butyl, 1,2-dimethyl-c-butyl, 1,3-dimethyl-c-butyl, 2,2-dimethyl-c-butyl, 2,3-dimethyl-c-butyl, 2,4-dimethyl-c-butyl, 3,3-dimethyl-c-butyl, 1-n-propyl-c-propyl, 2-n-propyl-c-propyl, 1-i-propyl-c-propyl, 2-i-propyl-c-propyl, 1,2,2-trimethyl-c-propyl, 1,2,3-trimethyl-c-propyl, 2,2,3-trimethyl-c-propyl, 1-ethyl-2-methyl-c-propyl, 2-ethyl-1-methyl-c-propyl, 2-ethyl-2-methyl-c-propyl, 2-ethyl-3-methyl-c-propyl, n-heptyl, n-octyl, n-nonyl, n-decyl, n-undecyl and n-dodecyl groups.

The alkenyl group may be linear, branched or cyclic. Illustrative examples include ethenyl, 1-propenyl, 2-propenyl, 1-methyl-1-ethenyl, 1-n-butenyl, 2-n-butenyl, 3-n-butenyl, 2-methyl-1-propenyl, 2-methyl-2-propenyl, 1-ethylethenyl, 1-methyl-1-propenyl, 1-methyl-2-propenyl, 1-n-pentenyl, 2-n-pentenyl, 3-n-pentenyl, 4-n-pentenyl, 1-n-propylethenyl, 1-methyl-1-n-butenyl, 1-methyl-2-n-butenyl, 1-methyl-3-n-butenyl, 2-ethyl-2-propenyl, 2-methyl-1-n-butenyl, 2-methyl-2-n-butenyl, 2-methyl-3-n-butenyl, 3-methyl-1-n-butenyl, 3-methyl-2-n-butenyl, 3-methyl-3-n-butenyl, 1,1-dimethyl-2-propenyl, 1-i-propylethenyl, 1-2-dimethyl-1-n-propenyl, 1,2-dimethyl-2-n-propenyl, 1-c-pentenyl, 2-c-pentenyl, 3-c-pentenyl, 1-n-hexenyl, 2-n-hexenyl, 3-n-hexenyl, 4-n-hexenyl, 5-n-hexenyl, 1-methyl-1-n-pentenyl, 1-methyl-2-n-pentenyl, 1-methyl-3-n-pentenyl, 1-methyl-4-n-pentenyl, 1-n-butylethenyl, 2-methyl-1-n-pentenyl, 2-methyl-2-n-pentenyl, 2-methyl-3-n-pentenyl, 2-methyl-4-n-pentenyl, 2-n-propyl-2-n-propenyl, 3-methyl-1-n-pentenyl, 3-methyl-2-n-pentenyl, 3-methyl-3-n-pentenyl, 3-methyl-4-n-pentenyl, 3-ethyl-3-n-butenyl, 4-methyl-1-n-pentenyl, 4-methyl-2-n-pentenyl, 4-methyl-3-n-pentenyl, 4-methyl-4-n-pentenyl, 1,1-dimethyl-2-n-butenyl, 1,1-dimethyl-3-n-butenyl, 1,2-dimethyl- 1-n-butenyl, 1,2-dimethyl-2-n-butenyl, 1,2-dimethyl-3-n-butenyl, 1-methyl-2-ethyl-2-n-propenyl, 1-s-butylethenyl, 1,3-dimethyl-1-n-butenyl, 1,3-dimethyl-2-n-butenyl, 1,3-dimethyl-3-n-butenyl, 1-i-butylethenyl, 2,2-dimethyl-3-n-butenyl, 2,3-dimethyl-1-n-butenyl, 2,3-dimethyl-2-n-butenyl, 2,3-dimethyl-3-n-butenyl, 2-i-propyl-2-n-propenyl, 3,3-dimethyl-1-n-butenyl, 1-ethyl-1-n-butenyl, 1-ethyl-2-n-butenyl, 1-ethyl-3-n-butenyl, 1-n-propyl-1-n-propenyl, 1-n-propyl-2-n-propenyl, 2-ethyl-1-n-butenyl, 2-ethyl-2-n-butenyl, 2-ethyl-3-n-butenyl, 1,1,2-trimethyl-2-propenyl, 1-t-butylethenyl, 1-methyl-1-ethyl-2-propenyl, 1-ethyl-2-methyl-1-n-propenyl, 1-ethyl-2-methyl-2-propenyl, 1-i-propyl-1-propenyl, 1-i-propyl-2-n-propenyl, 1-methyl-2-c-pentenyl, 1-methyl-3-c-pentenyl, 2-methyl-1-c-pentenyl, 2-methyl-2-c-pentenyl, 2-methyl-3-c-pentenyl, 2-methyl-4-c-pentenyl, 2-methyl-5-c-pentenyl, 2-methylene-c-pentyl, 3-methyl-1-c-pentenyl, 3-methyl-2-c-pentenyl, 3-methyl-3-c-pentenyl, 3-methyl-4-c-pentenyl, 3-methyl-5-c-pentenyl, 3-methylene-c-pentyl, 1-c-hexenyl, 2-c-hexenyl and 3-c-hexenyl groups.

The alkynyl group may be linear, branched or cyclic. Illustrative examples include ethynyl, 1-propynyl, 2-propynyl, 1-n-butynyl, 2-n-butynyl, 3-n-butynyl, 1-methyl-2-propynyl, 1-n-pentynyl, 2-n-pentynyl, 3-n-pentynyl, 4-n-pentynyl, 1-methyl-2-n-butynyl, 1-methyl-3-n-butynyl, 2-methyl-3-n-butynyl, 3-methyl-1-n-butynyl, 1,1-dimethyl-2-propynyl, 2-ethyl-2-propynyl, 1-n-hexynyl, 2-n-hexynyl, 3-n-hexynyl, 4-n-hexynyl, 5-n-hexynyl, 1-methyl-2-pentynyl, 1-methyl-3-n-pentynyl, 1-methyl-4-n-pentynyl, 2-methyl-3-n-pentynyl, 2-methyl-4-n-pentynyl, 3-methyl-1-n-pentynyl, 3-methyl-4-n-pentynyl, 4-methyl-1-n-pentynyl, 4-methyl-2-n-pentynyl, 1,1-dimethyl-2-n-butynyl, 1,1-dimethyl-3-n-butynyl, 1,2-dimethyl-3-n-butynyl, 2,2-dimethyl-3-n-butynyl, 3,3-dimethyl-1-butynyl, 1-ethyl-2-butynyl, 1-ethyl-3-butynyl, 1-n-propyl-2-propynyl, 2-ethyl-3-n-butynyl, 1-methyl-1-ethyl-2-propynyl and 1-i-propyl-2-propynyl groups.

Illustrative examples of the aryl group include phenyl, α-naphthyl, β-naphthyl, o-biphenyl, m-biphenyl, p-biphenyl, 1-anthryl, 2-anthryl, 9-anthryl, 1-phenanthryl, 2-phenanthryl, 3-phenanthryl-4-phenanthryl and 9-phenanthryl groups.

Illustrative examples of the heteroaryl group include 2-furyl, 3-furyl, 2-thienyl, 3-thienyl, 1-pyrrolyl, 2-pyrrolyl, 3-pyrrolyl, 1-imidazolyl, 2-imidazolyl and 4-imidazolyl groups.

The alkoxy group may be linear, branched or cyclic. Illustrative examples include methoxy, ethoxy, n-propoxy, i-propoxy, c-propoxy, n-butoxy, i-butoxy, s-butoxy, t-butoxy, c-butoxy, n-pentyloxy, 1-methyl-n-butoxy, 2-methyl-n-butoxy, 3-methyl-n-butoxy, 1,1-dimethyl-n-propoxy, c-pentyloxy, 2-methyl-c-butoxy, n-hexyloxy, 1-methyl-n-pentyloxy, 2-methyl-n-pentyloxy, 1,1-dimethyl-n-butoxy, 1-ethyl-n-butoxy, 1,1,2-trimethyl-n-propoxy, c-hexyloxy, 1-methyl-c-pentyloxy, 1-ethyl-c-butoxy, 1,2-dimethyl-c-butoxy, n-heptyloxy, n-octyloxy, n-nonyloxy, n-decyloxy, n-undecyloxy and n-dodecyloxy groups.

The alkylthio group may be linear, branched or cyclic. Illustrative examples include methylthio, ethylthio, n-propylthio, i-propylthio, n-butylthio, s-butylthio, t-butylthio, n-pentylthio, 1-methylbutylthio, 2-methyl-n-butylthio, 3-methyl-n-butylthio, 1,1-dimethylpropylthio, 2,2-dimethylpropylthio, n-hexylthio, 1-methyl-n-pentylthio, 2-methyl-n-pentylthio, 1,1-dimethyl-n-butylthio, 1-ethyl-n-butylthio, 1,1,2-trimethylpropylthio, n-heptylthio, n-octylthio, 2-ethyl-n-hexylthio, n-nonylthio, n-decylthio, n-undecylthio and n-dodecylthio groups.

The monoalkylamino group may be linear, branched or cyclic. Illustrative examples include methylamino, ethylamino, n-propylamino, i-propylamino, c-propylamino, n-butylamino, i-butylamino, s-butylamino, t-butylamino, c-butylamino, 1-methyl-c-propylamino, 2-methyl-c-propylamino, n-pentylamino, 1-methyl-n-butylamino, 2-methyl-n-butylamino, 3-methyl-n-butylamino, 1,1-dimethyl-n-propylamino, 1,2-dimethyl-n-propylamino, 2,2-dimethyl-n-propylamino, 1-ethyl-n-propylamino, c-pentylamino, 1-methyl-c-butylamino, 2-methyl-c-butylamino, 3-methyl-c-butylamino, 1,2-dimethyl-c-propylamino, 2,3-dimethyl-c-propylamino, 1-ethyl-c-propylamino, 2-ethyl-c-propylamino, n-hexylamino, 1-methyl-n-pentylamino, 2-methyl-n-pentylamino, 3-methyl-n-pentylamino, 4-methyl-n-pentylamino, 1,1-dimethyl-n-butylamino, 1,2-dimethyl-n-butylamino, 1,3-dimethyl-n-butylamino, 2,2-dimethyl-n-butylamino, 2,3-dimethyl-n-butylamino, 3,3-dimethyl-n-butylamino, 1-ethyl-n-butylamino, 2-ethyl-n-butylamino, 1,1,2-trimethyl-n-propylamino, 1,2,2-trimethyl-n-propylamino, 1-ethyl-1-methyl-n-propylamino, 1-ethyl-2-methyl-n-propylamino, c-hexylamino, 1-methyl-c-pentylamino, 2-methyl-c-pentylamino, 3-methyl-c-pentylamino, 1-ethyl-c-butylamino, 2-ethyl-c-butylamino, 3-ethyl-c-butylamino, 1,2-dimethyl-c-butylamino, 1,3-dimethyl-c-butylamino, 2,2-dimethyl-c-butylamino, 2,3-dimethyl-c-butylamino, 2,4-dimethyl-c-butylamino, 3,3-dimethyl-c-butylamino, 1-n-propyl-c-propylamino, 2-n-propyl-c-propylamino, 1-i-propyl-c-propylamino, 2-i-propyl-c-propylamino, 1,2,2-trimethyl-c-propylamino, 1,2,3-trimethyl-c-propylamino, 2,2,3-trimethyl-c-propylamino, 1-ethyl-2-methyl-c-propylamino, 2-ethyl-1-methyl-c-propylamino, 2-ethyl-2-methyl-c-propylamino and 2-ethyl-3-methyl-c-propylamino groups.

The dialkylamino group may be linear, branched or cyclic. Illustrative examples include dimethylamino, diethylamino, di-n-propylamino, di-i-propylamino, di-c-propylamino, di-n-butylamino, di-i-butylamino, di-s-butylamino, di-t-butylamino, di-c-butylamino, di(1-methyl-c-propyl)amino, di(2-methyl-c-propyl)amino, di-n-pentylamino, di(1-methyl-n-butyl)amino, di(2-methyl-n-butyl)amino, di(3-methyl-n-butyl)amino, di(1,1-dimethyl-n-propyl)amino, di(1,2-dimethyl-n-propyl)amino, di(2,2-dimethyl-n-propyl)amino, di(1-ethyl-n-propyl)amino, di-c-pentylamino, di(1-methyl-c-butyl)amino, di(2-methyl-c-butyl)amino, di(3-methyl-c-butyl)amino, di(1,2-dimethyl-c-propyl)amino, di(2,3-dimethyl-c-propyl)amino, di(1-ethyl-c-propyl)amino, di(2-ethyl-c-propyl)amino, di-n-hexylamino, di(l-methyl-n-pentyl)amino, di(2-methyl-n-pentyl)amino, di(3-methyl-n-pentyl)amino, di(4-methyl-n-pentyl)amino, di(1,1-dimethyl-n-butyl)amino, di(1,2-dimethyl-n-butyl)amino, di(1,3-dimethyl-n-butyl)amino, di(2,2-dimethyl-n-butyl)amino, di(2,3-dimethyl-n-butyl)amino, di(3,3-dimethyl-n-butyl)amino, di(1-ethyl-n-butyl)amino, di(2-ethyl-n-butyl)amino, di(1,1,2-trimethyl-n-propyl)amino, di(1,2,2-trimethyl-n-propyl)amino, di(1-ethyl-1-methyl-n-propyl)amino, di(1-ethyl-2-methyl-n-propyl)amino, di-c-hexylamino, di(1-methyl-c-pentyl)amino, di(2-methyl-c-pentyl)amino, di(3-methyl-c-pentyl)amino, di(1-ethyl-c-butyl)amino, di(2-ethyl-c-butyl)amino, di(3-ethyl-c-butyl)amino, di(1,2-dimethyl-c-butyl)amino, di(1,3-dimethyl-c-butyl)amino, di(2,2-dimethyl-c-butyl)amino, di(2,3-dimethyl-c-butyl)amino, di(2,4-dimethyl-c-butyl)amino, di(3,3-dimethyl-c-butyl)amino, di(1-n-propyl-c-propyl)amino, di(2-n-propyl-c-propyl)amino, di(1-i-propyl-c-propyl)amino, di(2-i-propyl-c-propyl)amino, di(1,2,2-trimethyl-c-propyl)amino, di(1,2,3-trimethyl-c-propyl)amino, di(2,2,3-trimethyl-c-propyl)amino, di(1-ethyl-2-methyl-c-propyl)amino, di(2-ethyl-1-methyl-c-propyl)

amino, di(2-ethyl-2-methyl-c-propyl)amino and di(2-ethyl-3-methyl-c-propyl)amino groups.

Illustrative examples of the alkylcarbonyl group include methylcarbonyl, ethylcarbonyl, n-propylcarbonyl, i-propylcarbonyl, c-propylcarbonyl, n-butylcarbonyl, i-butylcarbonyl, s-butylcarbonyl, t-butylcarbonyl, c-butylcarbonyl, 1-methyl-c-propylcarbonyl, 2-methyl-c-propylcarbonyl, n-pentylcarbonyl, 1-methyl-n-butylcarbonyl, 2-methyl-n-butylcarbonyl, 3-methyl-n-butylcarbonyl, 1,1-dimethyl-n-propylcarbonyl, 1,2-dimethyl-n-propylcarbonyl, 2,2-dimethyl-n-propylcarbonyl, 1-ethyl-n-propylcarbonyl, c-pentylcarbonyl, 1-methyl-c-butylcarbonyl, 2-methyl-c-butylcarbonyl, 3-methyl-c-butylcarbonyl, 1,2-dimethyl-c-propylcarbonyl, 2,3-dimethyl-c-propylcarbonyl, 1-ethyl-c-propylcarbonyl, 2-ethyl-c-propylcarbonyl, n-hexylcarbonyl, 1-methyl-n-pentylcarbonyl, 2-methyl-n-pentylcarbonyl, 3-methyl-n-pentylcarbonyl, 4-methyl-n-pentylcarbonyl, 1,1-dimethyl-n-butylcarbonyl, 1,2-dimethyl-n-butylcarbonyl, 1,3-dimethyl-n-butylcarbonyl, 2,2-dimethyl-n-butylcarbonyl, 2,3-dimethyl-n-butylcarbonyl, 3,3-dimethyl-n-butylcarbonyl, 1-ethyl-n-butylcarbonyl, 2-ethyl-n-butylcarbonyl, 1,1,2-trimethyl-n-propylcarbonyl, 1,2,2-trimethyl-n-propylcarbonyl, 1-ethyl-1-methyl-n-propylcarbonyl, 1-ethyl-2-methyl-n-propylcarbonyl, c-hexylcarbonyl, 1-methyl-c-pentylcarbonyl, 2-methyl-c-pentylcarbonyl, 3-methyl-c-pentylcarbonyl, 1-ethyl-c-butylcarbonyl, 2-ethyl-c-butylcarbonyl, 3-ethyl-c-butylcarbonyl, 1,2-dimethyl-c-butylcarbonyl, 1,3-dimethyl-c-butylcarbonyl, 2,2-dimethyl-c-butylcarbonyl, 2,3-dimethyl-c-butylcarbonyl, 2,4-dimethyl-c-butylcarbonyl, 3,3-dimethyl-c-butylcarbonyl, 1-n-propyl-c-propylcarbonyl, 2-n-propyl-c-propylcarbonyl, 1-i-propyl-c-propylcarbonyl, 2-i-propyl-c-propylcarbonyl, 1,2,2-trimethyl-c-propylcarbonyl, 1,2,3-trimethyl-c-propylcarbonyl, 2,2,3-trimethyl-c-propylcarbonyl, 1-ethyl-2-methyl-c-propylcarbonyl, 2-ethyl-1-methyl-c-propylcarbonyl, 2-ethyl-2-methyl-c-propylcarbonyl and 2-ethyl-3-methyl-c-propylcarbonyl groups.

Illustrative examples of the alkylaminocarbonyl group include methylaminocarbonyl, ethylaminocarbonyl, n-propylaminocarbonyl, i-propylaminocarbonyl, c-propylaminocarbonyl, n-butylaminocarbonyl, i-butylaminocarbonyl, s-butylaminocarbonyl, t-butylaminocarbonyl, c-butylaminocarbonyl, 1-methyl-c-propylaminocarbonyl, 2-methyl-c-propylaminocarbonyl, n-pentylaminocarbonyl, 1-methyl-n-butylaminocarbonyl, 2-methyl-n-butylaminocarbonyl, 3-methyl-n-butylaminocarbonyl, 1,1-dimethyl-n-propylaminocarbonyl, 1,2-dimethyl-n-propylaminocarbonyl, 2,2-dimethyl-n-propylaminocarbonyl, 1-ethyl-n-propylaminocarbonyl, c-pentylaminocarbonyl, 1-methyl-c-butylaminocarbonyl, 2-methyl-c-butylaminocarbonyl, 3-methyl-c-butylaminocarbonyl, 1,2-dimethyl-c-propylaminocarbonyl, 2,3-dimethyl-c-propylaminocarbonyl, 1-ethyl-c-propylaminocarbonyl, 2-ethyl-c-propylaminocarbonyl, n-hexylaminocarbonyl, 1-methyl-n-pentylaminocarbonyl, 2-methyl-n-pentylaminocarbonyl, 3-methyl-n-pentylaminocarbonyl, 4-methyl-n-pentylaminocarbonyl, 1,1-dimethyl-n-butylaminocarbonyl, 1,2-dimethyl-n-butylaminocarbonyl, 1,3-dimethyl-n-butylaminocarbonyl, 2,2-dimethyl-n-butylaminocarbonyl, 2,3-dimethyl-n-butylaminocarbonyl, 3,3-dimethyl-n-butylaminocarbonyl, 1-ethyl-n-butylaminocarbonyl, 2-ethyl-n-butylaminocarbonyl, 1,1,2-trimethyl-n-propylaminocarbonyl, 1,2,2-trimethyl-n-propylaminocarbonyl, 1-ethyl-1-methyl-n-propylaminocarbonyl, 1-ethyl-2-methyl-n-propylaminocarbonyl, c-hexylaminocarbonyl, 1-methyl-c-pentylaminocarbonyl, 2-methyl-c-pentylaminocarbonyl, 3-methyl-c-pentylaminocarbonyl, 1-ethyl-c-butylaminocarbonyl, 2-ethyl-c-butylaminocarbonyl, 3-ethyl-c-butylaminocarbonyl, 1,2-dimethyl-c-butylaminocarbonyl, 1,3-dimethyl-c-butylaminocarbonyl, 2,2-dimethyl-c-butylaminocarbonyl, 2,3-dimethyl-c-butylaminocarbonyl, 2,4-dimethyl-c-butylaminocarbonyl, 3,3-dimethyl-c-butylaminocarbonyl, 1-n-propyl-c-propylaminocarbonyl, 2-n-propyl-c-propylaminocarbonyl, 1-i-propyl-c-propylaminocarbonyl, 2-i-propyl-c-propylaminocarbonyl, 1,2,2-trimethyl-c-propylaminocarbonyl, 1,2,3-trimethyl-c-propylaminocarbonyl, 2,2,3-trimethyl-c-propylaminocarbonyl, 1-ethyl-2-methyl-c-propylaminocarbonyl, 2-ethyl-1-methyl-c-propylaminocarbonyl, 2-ethyl-2-methyl-c-propylaminocarbonyl and 2-ethyl-3-methyl-c-propylaminocarbonyl groups.

Of these, to increase the voltage, capacity and electrical conductivity, $R^1$ to $R^3$, $R^{22}$ and $R^{41}$ to $R^{43}$ are preferably each independently a methyl, ethyl, n-propyl, i-propyl, n-butyl, s-butyl, t-butyl, n-pentyl, 1-methylbutyl, 2-methylbutyl, 3-methylbutyl, 1,1-dimethylpropyl, 2,2-dimethylpropyl, n-hexyl, 1-methylpentyl, 2-methylpentyl, 1,1-dimethylbutyl, 1-ethylbutyl or 1,1,2-trimethylpropyl group; and more preferably a methyl, ethyl, n-propyl, i-propyl, n-butyl, s-butyl or t-butyl group. $R^4$ to $R^{21}$, $R^{23}$ to $R^{40}$ and $R^{44}$ to $R^{76}$ are preferably each independently a hydrogen atom, chlorine atom, methyl group, ethyl group, n-propyl group, i-propyl group, n-butyl group, s-butyl group, t-butyl group, n-pentyl group, 1-methylbutyl group, 2-methylbutyl group, 3-methylbutyl group, 1,1-dimethylpropyl group, 2,2-dimethylpropyl group, n-hexyl group, 1-methylpentyl group, 2-methylpentyl group, 1,1-dimethylbutyl group, 1-ethylbutyl group, 1,1,2-trimethylpropyl group, methylcarbonyl group, nitro group, cyano group, sulfonic acid group, phosphonic acid group, carboxyl group, aminocarbonyl group, or methylaminocarbonyl group; and more preferably a hydrogen atom, chlorine atom, methyl group, ethyl group, n-propyl group, i-propyl group, n-butyl group, s-butyl group, t-butyl group, methylcarbonyl group, nitro group, cyano group, sulfonic acid group, phosphonic acid group, carboxyl group, aminocarbonyl group, or methylaminocarbonyl group. $R^4$ to $R^{21}$ and $R^{23}$ to $R^{40}$ are most preferably hydrogen atoms.

Some or all of the hydrogen atoms that bond to the carbon atoms in the above groups may be replaced with substituents. Such substituents are exemplified by halogen atoms such as fluorine, chlorine, bromine and iodine atoms, hydroxyl groups, mercapto groups, amino groups, alkoxy groups of 1 to 11 carbon atoms, haloalkoxy groups of 1 to 11 carbon atoms, alkylthio groups of 1 to 11 carbon atoms, monoalkylamino groups of 1 to 11 carbons, dialkylamino groups in which each alkyl group is independently an alkyl group of 1 to 11 carbons, glycidoxy groups, alkylcarbonyl groups of 2 to 11 carbon atoms, alkenylcarbonyl groups of 3 to 11 carbon atoms, alkynylcarbonyl groups of 3 to 11 carbon atoms, alkylcarbonyloxy groups of 2 to 11 carbon atoms, alkenylcarbonyloxy groups of 3 to 11 carbon atoms, alkynylcarbonyloxy groups of 3 to 11 carbon atoms, aryl groups of 6 to 11 carbon atoms, halogenated aryl groups of 6 to 11 carbon atoms, heteroaryl groups of 3 to 11 carbon atoms, and halogenated heteroaryl groups of 3 to 11 carbon atoms. When such substituents are present, the upper limit in the total number of carbon atoms in each of $R^1$ to $R^{76}$ is 12.

Illustrative examples of the alkoxy group of 1 to 11 carbon atoms include methoxy, ethoxy, n-propoxy, i-propoxy, c-propoxy, n-butoxy, i-butoxy, s-butoxy, t-butoxy, c-butoxy, 1-methyl-c-propoxy, 2-methyl-c-propoxy, n-pentyloxy, 1-methyl-n-butoxy, 2-methyl-n-butoxy, 3-methyl-n-butoxy, 1,1-dimethyl-n-propoxy, 1,2-dimethyln-propoxy, 2,2-dimethyl-n-propoxy, 1-ethyl-n-propoxy, c-pentyloxy, 1-methyl-c-butoxy, 2-methyl-c-butoxy, 3-methyl-c-butoxy, 1,2-dimethyl-c-propoxy, 2,3-dimethyl-c-propoxy, 1-ethyl-c-propoxy, 2-ethyl-c-propoxy, n-hexyloxy, 1-methyl-n-pentyloxy, 2-methyl-n-pentyloxy, 3-methyl-n-pentyloxy, 4-methyl-n-pentyloxy, 1,1-dimethyl-n-butoxy, 1,2-dimethyl-n-butoxy, 1,3-dimethyl-n-butoxy, 2,2-dimethyl-n-butoxy, 2,3-dimethyl-n-butoxy, 3,3-dimethyl-n-butoxy, 1-ethyl-n-butoxy, 2-ethyl-n-butoxy, 1,1,2-trimethyl-n-propoxy, 1,2,2-trimethyl-n-propoxy, 1-ethyl-1-methyl-n-propoxy, 1-ethyl-2-methyl-n-propoxy, c-hexyloxy, 1-methyl-c-pentyloxy, 2-methyl-c-pentyloxy, 3-methyl-c-pentyloxy, 1-ethyl-c-butoxy, 2-ethyl-c-butoxy, 3-ethyl-c-butoxy, 1,2-dimethyl-c-butoxy, 1,3-dimethyl-c-butoxy, 2,2-dimethyl-c-butoxy, 2,3-dimethyl-c-butoxy, 2,4-dimethyl-c-butoxy, 3,3-dimethyl-c-butoxy, 1-n-propyl-c-propoxy, 2-n-propyl-c-propoxy, 1-i-propyl-c-propoxy, 2-i-propyl-c-propoxy, 1,2,2-trimethyl-c-propoxy, 1,2,3-trimethyl-c-propoxy, 2,2,3-trimethyl-c-propoxy, 1-ethyl-2-methyl-c-propoxy, 2-ethyl-1-methyl-c-propoxy, 2-ethyl-2-methyl-c-propoxy, 2-ethyl-3-methyl-c-propoxy, n-heptyloxy, n-octyloxy, n-nonyloxy, n-decyloxy and n-undecyloxy groups.

Illustrative examples of the haloalkoxy group of 1 to 11 carbons include difluoromethoxy, trifluoromethoxy, bromodifluoromethoxy, 2-chloroethoxy, 2-bromoethoxy, 1,1-difluoroethoxy, 2,2,2-trifluoroethoxy, 1,1,2,2-tetrafluoroethoxy, 2-chloro-1,1,2-trifluoroethoxy, pentafluoroethoxy, 3-bromopropoxy, 2,2,3,3-tetrafluoropropoxy, 1,1,2,3,3,3-hexafluoropropoxy, 1,1,1,3,3,3-hexafluoropropan-2-yloxy, 3-bromo-2-methylpropoxy, 4-bromobutoxy and perfluoropentyloxy groups.

Illustrative examples of the alkylthio group of 1 to 11 carbon atoms include methylthio, ethylthio, n-propylthio, i-propylthio, c-propylthio, n-butylthio, i-butylthio, s-butylthio, t-butylthio, c-butylthio, 1-methyl-c-propylthio, 2-methyl-c-propylthio, n-pentylthio, 1-methyl-n-butylthio, 2-methyl-n-butylthio, 3-methyl-n-butylthio, 1,1-dimethyl-n-propylthio, 1,2-dimethyl-n-propylthio, 2,2-dimethyl-n-propylthio, 1-ethyl-n-propylthio, c-pentylthio, 1-methyl-c-butylthio, 2-methyl-c-butylthio, 3-methyl-c-butylthio, 1,2-dimethyl-c-propylthio, 2,3-dimethyl-c-propylthio, 1-ethyl-c-propylthio, 2-ethyl-c-propylthio, n-hexylthio, 1-methyl-n-pentylthio, 2-methyl-n-pentylthio, 3-methyl-n-pentylthio, 4-methyl-n-pentylthio, 1,1-dimethyl-n-butylthio, 1,2-dimethyl-n-butylthio, 1,3-dimethyl-n-butylthio, 2,2-dimethyl-n-butylthio, 2,3-dimethyl-n-butylthio, 3,3-dimethyl-n-butylthio, 1-ethyl-n-butylthio, 2-ethyl-n-butylthio, 1,1,2-trimethyl-n-propylthio, 1,2,2-trimethyl-n-propylthio, 1-ethyl-1-methyl-n-propylthio, 1-ethyl-2-methyl-n-propylthio, c-hexylthio, 1-methyl-c-pentylthio, 2-methyl-c-pentylthio, 3-methyl-c-pentylthio, 1-ethyl-c-butylthio, 2-ethyl-c-butylthio, 3-ethyl-c-butylthio, 1,2-dimethyl-c-butylthio, 1,3-dimethyl-c-butylthio, 2,2-dimethyl-c-butylthio, 2,3-dimethyl-c-butylthio, 2,4-dimethyl-c-butylthio, 3,3-dimethyl-c-butylthio, 1-n-propyl-c-propylthio, 2-n-propyl-c-propylthio, 1-i-propyl-c-propylthio, 2-i-propyl-c-propylthio, 1,2,2-trimethyl-c-propylthio, 1,2,3-trimethyl-c-propylthio, 2,2,3-trimethyl-c-propylthio, 1-ethyl-2-methyl-c-propylthio, 2-ethyl-1-methyl-c-propylthio, 2-ethyl-2-methyl-c-propylthio, 2-ethyl-3-methyl-c-propylthio, n-heptylthio, n-octylthio, n-nonylthio, n-decylthio and n-undecylthio groups.

Illustrative examples of the monoalkylamino group of 1 to 11 carbon atoms include methylamino, ethylamino, n-propylamino, i-propylamino, c-propylamino, n-butylamino, i-butylamino, s-butylamino, t-butylamino, c-butylamino, 1-methyl-c-propylamino, 2-methyl-c-propylamino, n-pentylamino, 1-methyl-n-butylamino, 2-methyl-n-butylamino, 3-methyl-n-butylamino, 1,1-dimethyl-n-propylamino, 1,2-dimethyl-n-propylamino, 2,2-dimethyl-n-propylamino, 1-ethyl-n-propylamino, c-pentylamino, 1-methyl-c-butylamino, 2-methyl-c-butylamino, 3-methyl-c-butylamino, 1,2-dimethyl-c-propylamino, 2,3-dimethyl-c-propylamino, 1-ethyl-c-propylamino, 2-ethyl-c-propylamino, n-hexylamino, 1-methyl-n-pentylamino, 2-methyl-n-pentylamino, 3-methyl-n-pentylamino, 4-methyl-n-pentylamino, 1,1-dimethyl-n-butylamino, 1,2-dimethyl-n-butylamino, 1,3-dimethyl-n-butylamino, 2,2-dimethyl-n-butylamino, 2,3-dimethyl-n-butylamino, 3,3-dimethyl-n-butylamino, 1-ethyl-n-butylamino, 2-ethyl-n-butylamino, 1,1,2-trimethyl-n-propylamino, 1,2,2-trimethyl-n-propylamino, 1-ethyl-1-methyl-n-propylamino, 1-ethyl-2-methyl-n-propylamino, c-hexylamino, 1-methyl-c-pentylamino, 2-methyl-c-pentylamino, 3-methyl-c-pentylamino, 1-ethyl-c-butylamino, 2-ethyl-c-butylamino, 3-ethyl-c-butylamino, 1,2-dimethyl-c-butylamino, 1,3-dimethyl-c-butylamino, 2,2-dimethyl-c-butylamino, 2,3-dimethyl-c-butylamino, 2,4-dimethyl-c-butylamino, 3,3-dimethyl-c-butylamino, 1-n-propyl-c-propylamino, 2-n-propyl-c-propylamino, 1-i-propyl-c-propylamino, 2-i-propyl-c-propylamino, 1,2,2-trimethyl-c-propylamino, 1,2,3-trimethyl-c-propylamino, 2,2,3-trimethyl-c-propylamino, 1-ethyl-2-methyl-c-propylamino, 2-ethyl-1-methyl-c-propylamino, 2-ethyl-2-methyl-c-propylamino and 2-ethyl-3-methyl-c-propylamino groups.

Illustrative examples of the dialkylamino group in which each alkyl group is independently an alkyl group of 1 to 11 carbons include dimethylamino, diethylamino, di-n-propylamino, di-i-propylamino, di-c-propylamino, di-n-butylamino, di-i-butylamino, di-s-butylamino, di-t-butylamino, di-c-butylamino, di(1-methyl-c-propyl)amino, di(2-methyl-c-propyl)amino, di-n-pentylamino, di(1-methyl-n-butyl)amino, di(2-methyl-n-butyl)amino, di(3-methyl-n-butyl)amino, di(1,1-dimethyl-n-propyl)amino, di(1,2-dimethyl-n-propyl)amino, di(2,2-dimethyl-n-propyl)amino, di(1-ethyl-n-propyl)amino, di-c-pentylamino, di(1-methyl-c-butyl)amino, di(2-methyl-c-butyl)amino, di(3-methyl-c-butyl)amino, di(1,2-dimethyl-c-propyl)amino, di(2,3-dimethyl-c-propyl)amino, di(1-ethyl-c-propyl)amino, di(2-ethyl-c-propyl)amino, di-n-hexylamino, di(1-methyl-n-pentyl)amino, di(2-methyl-n-pentyl)amino, di(3-methyl-n-pentyl)amino, di(4-methyl-n-pentyl)amino, di(1,1-dimethyl-n-butyl)amino, di(1,2-dimethyl-n-butyl)amino, di(1,3-dimethyl-n-butyl)amino, di(2,2-dimethyl-n-butyl)amino, di(2,3-dimethyl-n-butyl)amino, di(3,3-dimethyl-n-butyl)amino, di(1-ethyl-n-butyl)amino, di(2-ethyl-n-butyl)amino, di(1,1,2-trimethyl-n-propyl)amino, di(1,2,2-trimethyl-n-propyl)amino, di(1-ethyl-1-methyl-n-propyl)amino, di(1-ethyl-2-methyl-n-propyl)amino, di-c-hexylamino, di(1-methyl-c-pentyl)amino, di(2-methyl-c-pentyl)amino, di(3-methyl-c-pentyl)amino, di(1-ethyl-c-butyl)amino, di(2-ethyl-c-butyl)amino, di-(3-ethyl-c-butyl)amino, di(1,2-dimethyl-c-butyl)amino, di(1,3-dimethyl-c-butyl)amino, di(2,2-dimethyl-c-butyl)amino, di(2,3-dimethyl-c-butyl)amino, di(2,4-dimethyl-c-butyl)amino, di(3,3-dimethyl-c-butyl)amino, di(1-n-propyl-c-propyl)amino, di(2-n-propyl-c-propyl)amino, di(1-i-propyl-c-propyl)amino, di(2-i-propyl-c-propyl)amino, di(1,2,2-trimethyl-c-propyl)amino, di(1,2,3-trimethyl-c-propyl)amino, di(2,2,3-trimethyl-c-propyl)amino, di(1-ethyl-2-methyl-c-propyl)amino, di(2-ethyl-1-methyl-c-propyl)amino, di(2-ethyl-2-methyl-c-propyl)amino and di(2-ethyl-3-methyl-c-propyl)amino groups.

Illustrative examples of the alkylcarbonyl group of 2 to 11 carbon atoms include methylcarbonyl, ethylcarbonyl, n-propylcarbonyl, i-propylcarbonyl, c-propylcarbonyl, n-butylcarbonyl, i-butylcarbonyl, s-butylcarbonyl, t-butylcarbonyl, c-butylcarbonyl, 1-methyl-c-propylcarbonyl, 2-methyl-c-propylcarbonyl, n-pentylcarbonyl, 1-methyl-n-butylcarbonyl, 2-methyl-n-butylcarbonyl, 3-methyl-n-butylcarbonyl, 1,1-dimethyl-n-propylcarbonyl, 1,2-dimethyl-n-propylcarbonyl, 2,2-dimethyl-n-propylcarbonyl, 1-ethyl-n-propylcarbonyl, c-pentylcarbonyl, 1-methyl-c-butylcarbonyl, 2-methyl-c-butylcarbonyl, 3-methyl-c-butylcarbonyl, 1,2-dimethyl-c-propylcarbonyl, 2,3-dimethyl-c-propylcarbonyl, 1-ethyl-c-propylcarbonyl, 2-ethyl-c-propylcarbonyl, n-hexylcarbonyl, 1-methyl-n-pentylcarbonyl, 2-methyl-n-pentylcarbonyl, 3-methyl-n-pentylcarbonyl, 4-methyl-n-pentylcarbonyl, 1,1-dimethyl-n-butylcarbonyl, 1,2-dimethyl-n-butylcarbonyl, 1,3-dimethyl-n-butylcarbonyl, 2,2-dimethyl-n-butylcarbonyl, 2,3-dimethyl-n-butylcarbonyl, 3,3-dimethyl-n-butylcarbonyl, 1-ethyl-n-butylcarbonyl, 2-ethyl-n-butylcarbonyl, 1,1,2-trimethyl-n-propylcarbonyl, 1,2,2-trimethyl-n-propylcarbonyl, 1-ethyl-1-methyl-n-propylcarbonyl, 1-ethyl-2-methyl-n-propylcarbonyl, c-hexylcarbonyl, 1-methyl-c-pentylcarbonyl, 2-methyl-c-pentylcarbonyl, 3-methyl-c-pentylcarbonyl, 1-ethyl-c-butylcarbonyl, 2-ethyl-c-butylcarbonyl, 3-ethyl-c-butylcarbonyl, 1,2-dimethyl-c-butylcarbonyl, 1,3-dimethyl-c-butylcarbonyl, 2,2-dimethyl-c-butylcarbonyl, 2,3-dimethyl-c-butylcarbonyl, 2,4-dimethyl-c-butylcarbonyl, 2,3-dimethyl-c-butylcarbonyl, 2,4-dimethyl-c-butylcarbonyl, 3,3-dimethyl-c-butylcarbonyl, 1-n-propyl-c-propylcarbonyl, 2-n-propyl-c-propylcarbonyl, 1-i-propyl-c-propylcarbonyl, 2-i-propyl-c-propylcarbonyl, 1,2,2-trimethyl-c-propylcarbonyl, 1,2,3-trimethyl-c-propylcarbonyl, 2,2,3-trimethyl-c-propylcarbonyl, 1-ethyl-2-methyl-c-propylcarbonyl, 2-ethyl-1-methyl-c-propylcarbonyl, 2-ethyl-2-methyl-c-propylcarbonyl and 2-ethyl-3-methyl-c-propylcarbonyl.

Illustrative examples of the alkenylcarbonyl group of 3 to 11 carbons include ethenylcarbonyl, 1-propenylcarbonyl, 2-propenylcarbonyl, 1-methyl-1-ethenylcarbonyl, 1-butenylcarbonyl, 2-butenylcarbonyl, 3-butenylcarbonyl, 2-methyl-1-propenylcarbonyl, 2-methyl-2-propenylcarbonyl, 1-ethylethenylcarbonyl, 1-methyl-1-propenylcarbonyl, 1-methyl-2-propenylcarbonyl, 1-pentenylcarbonyl, 2-pentenylcarbonyl, 3-pentenylcarbonyl, 4-pentenylcarbonyl, 1-n-propylethenylcarbonyl, 1-methyl-1-butenylcarbonyl, 1-methyl-2-butenylcarbonyl, 1-methyl-3-butenylcarbonyl, 2-ethyl-2-propenylcarbonyl, 2-methyl-1-butenylcarbonyl, 2-methyl-2-butenylcarbonyl, 2-methyl-3-butenylcarbonyl, 3-methyl-1-butenylcarbonyl, 2-methyl-3-butenylcarbonyl, 3-methyl-1-butenylcarbonyl, 3-methyl-2-butenylcarbonyl, 3-methyl-3-butenylcarbonyl, 1,1-dimethyl-2-propenylcarbonyl, 1-i-propylethenylcarbonyl, 1,2-dimethyl-1-propenylcarbonyl, 1,2-dimethyl-2-propenylcarbonyl, 1-c-pentenylcarbonyl, 2-c-pentenylcarbonyl, 3-c-pentenylcarbonyl, 1-hexenylcarbonyl, 2-hexenylcarbonyl, 3-hexenylcarbonyl, 4-hexenylcarbonyl, 5-hexenylcarbonyl, 1-methyl-1-pentenylcarbonyl, 1-methyl-2-pentenylcarbonyl, 1-methyl-3-pentenylcarbonyl, 1-methyl-4-pentenylcarbonyl, 1-n-butylethenylcarbonyl, 2-methyl-1-pentenylcarbonyl, 2-methyl-2-pentenylcarbonyl, 2-methyl-3-pentenylcarbonyl, 2-methyl-4-pentenylcarbonyl, 2-n-propyl-2-propenylcarbonyl, 3-methyl-1-pentenylcarbonyl, 3-methyl-2-pentenylcarbonyl, 3-methyl-3-pentenylcarbonyl, 3-methyl-4-pentenylcarbonyl, 3-ethyl-3-butenylcarbonyl, 4-methyl-1-pentenylcarbonyl, 4-methyl-2-pentenylcarbonyl, 4-methyl-3-pentenylcarbonyl, 4-methyl-4-pentenylcarbonyl, 1,1-dimethyl-2-butenylcarbonyl, 1,1-dimethyl-3-butenylcarbonyl, 1,2-dimethyl-1-butenylcarbonyl, 1,2-dimethyl-2-butenylcarbonyl, 1,2-dimethyl-3-butenylcarbonyl, 1-methyl-2-ethyl-2-propenylcarbonyl, 1-s-butylethenylcarbonyl, 1,3-dimethyl-1-butenylcarbonyl, 1,3-dimethyl-2-butenylcarbonyl, 1,3-dimethyl-3-butenylcarbonyl, 1-i-butylethenylcarbonyl, 2,2-dimethyl-3-butenylcarbonyl, 2,3-dimethyl-1-butenylcarbonyl, 2,3-dimethyl-2-butenylcarbonyl, 2,3-dimethyl-3-butenylcarbonyl, 2-i-propyl-2-propenylcarbonyl, 3,3-dimethyl-1-butenylcarbonyl, 1-ethyl-1-butenylcarbonyl, 1-ethyl-2-butenylcarbonyl, 1-ethyl-3-butenylcarbonyl, 1-n-propyl-1-propenylcarbonyl, 1-n-propyl-2-propenylcarbonyl, 2-ethyl-1-butenylcarbonyl, 2-ethyl-2-butenylcarbonyl, 2-ethyl-3-butenylcarbonyl, 1,1,2-trimethyl-2-propenylcarbonyl, 1-t-butylethenylcarbonyl, 1-methyl-i-ethyl-2-propenylcarbonyl, 1-ethyl-2-methyl-1-propenylcarbonyl, 1-ethyl-2-methyl-2-propenylcarbonyl, 1-i-propyl-1-propenylcarbonyl, 1-i-propyl-2-propenylcarbonyl, 1-methyl-2-c-pentenylcarbonyl, 1-methyl-3-c-pentenylcarbonyl, 2-methyl-1-c-pentenylcarbonyl, 2-methyl-2-c-pentenylcarbonyl, 2-methyl-3-c-pentenylcarbonyl, 2-methyl-4-c-pentenylcarbonyl, 2-methyl-5-c-pentenylcarbonyl, 2-methylene-c-pentylcarbonyl, 3-methyl-1-c-pentenylcarbonyl, 3-methyl-2-c-pentenylcarbonyl, 3-methyl-3-c-pentenylcarbonyl, 3-methyl-4-c-pentenylcarbonyl, 3-methyl-5-c-pentenylcarbonyl, 3-methylene-c-pentylcarbonyl, 1-c-hexenylcarbonyl, 2-c-hexenylcarbonyl and 3-c-hexenylcarbonyl groups.

Illustrative examples of the alkynylcarbonyl group of 3 to 11 carbon atoms include ethynylcarbonyl, 1-propynylcarbonyl, 2-propynylcarbonyl, 1-butynylcarbonyl, 2-butynylcarbonyl, 3-butynylcarbonyl, 1-methyl-2-propynylcarbonyl, 1-pentynylcarbonyl, 2-pentynylcarbonyl, 3-pentynylcarbonyl, 4-pentynylcarbonyl, 1-methyl-2-butynylcarbonyl, 1-methyl-3-butynylcarbonyl, 2-methyl-3-butynylcarbonyl, 3-methyl-1-butynylcarbonyl, 1,1-dimethyl-2-propynylcarbonyl, 2-ethyl-2-propynylcarbonyl, 1-hexynylcarbonyl, 2-hexynylcarbonyl, 3-hexynylcarbonyl, 4-hexynylcarbonyl, 5-hexynylcarbonyl, 1-methyl-2-pentynylcarbonyl, 1-methyl-3-pentynylcarbonyl, 1-methyl-4-pentynylcarbonyl, 2-methyl-3-pentynylcarbonyl, 2-methyl-4-pentynylcarbonyl, 3-methyl-1-pentynylcarbonyl, 3-methyl-4-pentynylcarbonyl, 4-methyl-1-pentynylcarbonyl, 4-methyl-2-pentynylcarbonyl, 1,1-dimethyl-2-butynylcarbonyl, 1,1-dimethyl-3-butynylcarbonyl, 1,2-dimethyl-3-butynylcarbonyl, 2,2-dimethyl-3-butynylcarbonyl, 3,3-dimethyl-1-butynylcarbonyl, 1-ethyl-2-butynylcarbonyl, 1-ethyl-3-butynylcarbonyl, 1-n-propyl-2-propynylcarbonyl, 2-ethyl-3-butynylcarbonyl, 1-methyl-1-ethyl-2-propynyl and 1-i-propyl-2-propynylcarbonyl groups.

Illustrative examples of the alkylcarbonyloxy group of 2 to 11 carbon atoms include methylcarbonyloxy, ethylcarbonyloxy, n-propylcarbonyloxy, i-propylcarbonyloxy, c-propylcarbonyloxy, n-butylcarbonyloxy, i-butylcarbonyloxy, s-butylcarbonyloxy, t-butylcarbonyloxy, c-butylcarbonyloxy, 1-methyl-c-propylcarbonyloxy, 2-methyl-c-propylcarbonyloxy, n-pentylcarbonyloxy, 1-methyl-n-butylcarbonyloxy, 2-methyl-n-butylcarbonyloxy, 3-methyl-n-butylcarbonyloxy, 1,1-dimethyl-n-propylcarbonyloxy, 1,2-dimethyl-n-propylcarbonyloxy, 2,2-dimethyl-n-propylcarbonyloxy, 1-ethyl-n-propylcarbonyloxy, c-pentylcarbonyloxy, 1-methyl-c-butylcarbonyloxy, 2-methyl-c-butylcarbonyloxy, 3-methyl-c-butylcarbonyloxy, 1,2-dimethyl-c-propylcarbonyloxy, 2,3-dimethyl-c-propylcarbonyloxy, 1-ethyl-c-propylcarbonyloxy, 2-ethyl-c-propylcarbonyloxy, n-hexylcarbonyloxy, 1-methyl-n-pentylcarbonyloxy, 2-methyl-n-pentylcarbonyloxy, 3-methyl-n-pentylcarbonyloxy, 4-methyl-n-pentylcarbonyloxy, 1,1-dimethyl-n-butylcarbonyloxy, 1,2-dimethyl-n-butylcarbonyloxy, 1,3-dimethyl-n-butylcarbonyloxy, 2,2-dimethyl-n-butylcarbonyloxy, 2,3-dimethyl-n-butylcarbonyloxy, 3,3-dimethyl-n-butylcarbonyloxy, 1-ethyl-n-butylcarbonyloxy, 2-ethyl-n-butylcarbonyloxy, 1,1,2-trimethyl-n-propylcarbonyloxy, 1,2,2-trimethyl-n-propylcarbonyloxy, 1-ethyl-1-methyl-n-propylcarbonyloxy, 1-ethyl-2-methyl-n-propylcarbonyloxy, c-hexylcarbonyloxy, 1-methyl-c-pentylcarbonyloxy, 2-methyl-c-pentylcarbonyloxy, 3-methyl-c-pentylcarbonyloxy, 1-ethyl-c-butylcarbonyloxy, 2-ethyl-c-butylcarbonyloxy, 3-ethyl-c-butylcarbonyloxy, 1,2-dimethyl-c-butylcarbonyloxy, 1,3-dimethyl-c-butylcarbonyloxy, 2,2-dimethyl-c-butylcarbonyloxy, 2,3-dimethyl-c-butylcarbonyloxy, 2,4-dimethyl-c-butylcarbonyloxy, 3,3-dimethyl-c-butylcarbonyloxy, 1-n-propyl-c-propylcarbonyloxy, 2-n-propyl-c-propylcarbonyloxy, 1-i-propyl-c-propylcarbonyloxy, 2-i-propyl-c-propylcarbonyloxy, 1,2,2-trimethyl-c-propylcarbonyloxy, 1,2,3-trimethyl-c-propylcarbonyloxy, 2,2,3-trimethyl-c-propylcarbonyloxy, 1-ethyl-2-methyl-c-propylcarbonyloxy, 2-ethyl-1-methyl-c-propylcarbonyloxy, 2-ethyl-2-methyl-c-propylcarbonyloxy and 2-ethyl-3-methyl-c-propylcarbonyloxy groups.

Illustrative examples of the alkenylcarbonyloxy group of 3 to 11 carbon atoms include ethenylcarbonyoxy, 1-propenylcarbonyloxy, 2-propenylcarbonyloxy, 1-methyl-1-ethenylcarbonyloxy, 1-butenylcarbonyloxy, 2-butenylcarbonyloxy, 3-butenylcarbonyloxy, 2-methyl-1-propenylcarbonyloxy, 2-methyl-2-propenylcarbonyloxy, 1-ethylethenylcarbonyloxy, 1-methyl-1-propenylcarbonyloxy, 1-methyl-2-propenylcarbonyloxy, 1-pentenylcarbonyloxy, 2-pentenylcarbonyloxy, 3-pentenylcarbonyloxy, 4-pentenylcarbonyloxy, 1-n-propylethenylcarbonyloxy, 1-methyl-1-butenylcarbonyloxy, 1-methyl-2-butenylcarbonyloxy, 1-methyl-3-butenylcarbonyloxy, 2-ethyl-2-propenylcarbonyloxy, 2-methyl-1-butenylcarbonyloxy, 2-methyl-2-butenylcarbonyloxy, 2-methyl-3-butenylcarbonyloxy, 3-methyl-1-butenylcarbonyloxy, 3-methyl-2-butenylcarbonyloxy, 3-methyl-3-butenylcarbonyloxy, 1,1-dimethyl-2-propenylcarbonyloxy, 1-i-propylethenylcarbonyloxy, 1,2-dimethyl-1-propenylcarbonyloxy, 1,2-dimethyl-2-propenylcarbonyloxy, 1-c-pentenylcarbonyloxy, 2-c-pentenylcarbonyloxy, 3-c-pentenylcarbonyloxy, 1-hexenylcarbonyloxy, 2-hexenylcarbonyloxy, 3-hexenylcarbonyloxy, 4-hexenylcarbonyloxy, 5-hexenylcarbonyloxy, 1-methyl-1-pentenylcarbonyloxy, 1-methyl-2-pentenylcarbonyloxy, 1-methyl-3-pentenylcarbonyloxy, 1-methyl-4-pentenylcarbonyloxy, 1-n-butylethenylcarbonyloxy, 2-methyl-1-pentenylcarbonyloxy, 2-methyl-2-pentenylcarbonyloxy, 2-methyl-3-pentenylcarbonyloxy, 2-methyl-4-pentenylcarbonyloxy, 2-n-propyl-2-propenylcarbonyloxy, 3-methyl-1-pentenylcarbonyloxy, 3-methyl-2-pentenylcarbonyloxy, 3-methyl-3-pentenylcarbonyloxy, 3-methyl-4-pentenylcarbonyloxy, 3-ethyl-3-butenylcarbonyloxy, 4-methyl-1-pentenylcarbonyloxy, 4-methyl-2-pentenylcarbonyloxy, 4-methyl-3-pentenylcarbonyloxy, 4-methyl-4-pentenylcarbonyloxy, 1,1-dimethyl-2-butenylcarbonyloxy, 1,1-dimethyl-3-butenylcarbonyloxy, 1,2-dimethyl-1-butenylcarbonyloxy, 1,2-dimethyl-2-butenylcarbonyloxy, 1,2-dimethyl-3-butenylcarbonyloxy, 1-methyl-2-ethyl-2-propenylcarbonyloxy, 1-s-butylethenylcarbonyloxy, 1,3-dimethyl-1-butenylcarbonyloxy, 1,3-dimethyl-2-butenylcarbonyloxy, 1,3-dimethyl-3-butenylcarbonyloxy, 1-i-butylethenylcarbonyloxy, 2,2-dimethyl-3-butenylcarbonyloxy, 2,3-dimethyl-1-butenylcarbonyloxy, 2,3-dimethyl-2-butenylcarbonyloxy, 2,3-dimethyl-3-butenylcarbonyloxy, 2-i-propyl-2-propenylcarbonyloxy, 3,3-dimethyl-1-butenylcarbonyloxy, 1-ethyl-1-butenylcarbonyloxy, 1-ethyl-2-butenylcarbonyloxy, 1-ethyl-3-butenylcarbonyloxy, 1-n-propyl-1-propenylcarbonyloxy, 1-n-propyl-2-propenylcarbonyloxy, 2-ethyl-1-butenylcarbonyloxy, 2-ethyl-2-butenylcarbonyloxy, 2-ethyl-3-butenylcarbonyloxy, 1,1,2-trimethyl-2-propenylcarbonyloxy, 1-t-butylethenylcarbonyloxy, 1-methyl-1-ethyl-2-propenylcarbonyloxy, 1-ethyl-2-methyl-1-propenylcarbonyloxy, 1-ethyl-2-methyl-2-propenylcarbonyloxy, 1-i-propyl-1-propenylcarbonyloxy, 1-i-propyl-2-propenylcarbonyloxy, 1-methyl-2-c-pentenylcarbonyloxy, 1-methyl-3-c-pentenylcarbonyloxy, 2-methyl-1-c-pentenylcarbonyloxy, 2-methyl-2-c-pentenylcarbonyloxy, 2-methyl-3-c-pentenylcarbonyloxy, 2-methyl-4-c-pentenylcarbonyloxy, 2-methyl-5-c-pentenylcarbonyloxy, 2-methylene-c-pentylcarbonyloxy, 3-methyl-1-c-pentenylcarbonyloxy, 3-methyl-2-c-pentenylcarbonyloxy, 3-methyl-3-c-pentenylcarbonyloxy, 3-methyl-4-c-pentenylcarbonyloxy, 3-methyl-5-c-pentenylcarbonyloxy, 3-methylene-c-pentylcarbonyloxy, 1-c-hexenylcarbonyloxy, 2-c-hexenylcarbonyloxy and 3-c-hexenylcarbonyloxy groups.

Illustrative examples of the alkynylcarbonyloxy group of 3 to 11 carbons include ethynylcarbonyloxy, 1-propynylcarbonyloxy, 2-propynylcarbonyloxy, 1-butynylcarbonyloxy, 2-butynylcarbonyloxy, 3-butynylcarbonyloxy, 1-methyl-2-propynylcarbonyloxy, 1-pentynylcarbonyloxy, 2-pentynylcarbonyloxy, 3-pentynylcarbonyloxy, 4-pentynylcarbonyloxy, 1-methyl-2-butynylcarbonyloxy, 1-methyl-3-butynylcarbonyloxy, 2-methyl-3-butynylcarbonyloxy, 3-methyl-1-butynylcarbonyloxy, 1,1-dimethyl-2-propynylcarbonyloxy, 2-ethyl-2-propynylcarbonyloxy, 1-hexynylcarbonyloxy, 2-hexynylcarbonyloxy, 3-hexynylcarbonyloxy, 4-hexynylcarbonyloxy, 5-hexynylcarbonyloxy, 1-methyl-2-pentynylcarbonyloxy, 1-methyl-3-pentynylcarbonyloxy, 1-methyl-4-pentynylcarbonyloxy, 2-methyl-3-pentynylcarbonyloxy, 2-methyl-4-pentynylcarbonyloxy, 3-methyl-1-pentynylcarbonyloxy, 3-methyl-4-pentynylcarbonyloxy, 4-methyl-1-pentynylcarbonyloxy, 4-methyl-2-pentynylcarbonyloxy, 1,1-dimethyl-2-butynylcarbonyloxy, 1,1-dimethyl-3-butynylcarbonyloxy, 1,2-dimethyl-3-butynylcarbonyloxy, 2,2-dimethyl-3-butynylcarbonyloxy, 3,3-dimethyl-1-butynylcarbonyloxy, 1-ethyl-2-butynylcarbonyloxy, 1-ethyl-3-butynylcarbonyloxy, 1-n-propyl-2-propynylcarbonyloxy, 2-ethyl-3-butynylcarbonyloxy, 1-methyl-1-ethyl-2-propynylcarbonyloxy and 1-i-propyl-2-propynylcarbonyloxy groups.

Illustrative examples of the aryl group of 6 to 11 carbon atoms, the halogenated aryl group of 6 to 11 carbon atoms, the heteroaryl group of 3 to 11 carbon atoms and the halogenated heteroaryl group of 3 to 11 carbon atoms include phenyl, o-chlorophenyl, m-chlorophenyl, p-chlorophenyl, o-fluorophenyl, p-fluorophenyl, α-naphthyl, β-naphthyl, furyl, chlorofuryl, fluorofuryl, thienyl, chlorothienyl, fluorothienyl, pyrrolyl, chloropyrrolyl, fluoropyrrolyl, imidazolyl, chloroimidazolyl and fluoroimidazolyl groups.

The dipyridine-fused benzoquinone skeleton-containing polymer that includes recurring units of formula (2) and/or (3) may additionally include recurring units of formula (8) below.

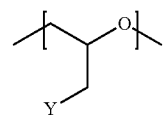

(8)

Here, Y is a halogen atom. Preferred examples of the halogen atom include chloride, bromide and iodide ions.

The content of recurring units of formula (8) is preferably from 0 to 90 mol %, more preferably from 0 to 50 mol %, and even more preferably from 0 to 20 mol %, of all the recurring units.

The dipyridine-fused benzoquinone skeleton-containing polymer that includes recurring units of formula (2) and/or (3) may additionally include recurring units of formula (9) below.

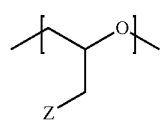

(9)

Here, Z is an alkoxy group such as a methoxy or ethoxy group, an alkyl group such as a methyl or ethyl group, an alkylthio group, an acyl group, an alkylamino group, a polyalkylene ether group such as polyethylene glycol, a polyalkyleneamine group such as polyethyleneimine, or an aryl group.

The content of recurring units of formula (9) is preferably from 0 to 10 mol %, more preferably from 0 to 5 mol %, and even more preferably from 0 to 1 mol %, of all the recurring units.

The dipyridine-fused benzoquinone skeleton-containing polymer that includes recurring units of formula (2) and/or (3) may additionally include recurring units of formula (9') below.

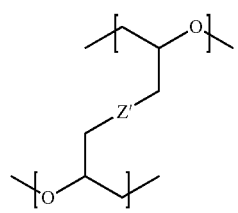

(9')

Here, Z' is —O—(CH$_2$)$_a$—O—, —(CH$_2$)$_a$—, —S—(CH$_2$)$_a$—S—, —C(=O)—(CH$_2$)$_b$—C(=O)—, —NH—(CH$_2$)$_a$—NH—, —O—(R—O)$_c$—, —NH—(R—NH)$_c$— or a phenylene group, and R is an alkylene group of 1 to 12 carbon atoms. Also, the letter a is an integer from 1 to 12, the letter b is an integer from 1 to 10, and the letter c is an integer from 2 to 4.

The content of recurring units of formula (9') is preferably from 0 to 10 mol %, more preferably from 0 to 5 mol %, and even more preferably from 0 to 1 mol %, of all the recurring units.

The dipyridine-fused benzoquinone skeleton-containing polymer that includes recurring units of formula (5) and/or (6) may additionally include recurring units of formula (8') below.

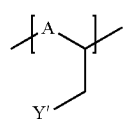

(8')

Here, A is as defined above. Y' is an amino, amido or alkylaminocarboxyl group. An amino group is preferred.

The content of recurring units of formula (8') is preferably from 0 to 90 mol %, more preferably from 0 to 50 mol %, and even more preferably from 0 to 20 mol %, of all the recurring units.

Next, methods for synthesizing dipyridine-fused benzoquinones of formula (1), derivatives thereof, and dipyridine-fused benzoquinone skeleton-containing polymers which include recurring units of formula (2) and/or (3) are described.

Dipyridine-fused benzoquinones of formula (1) can be synthesized by a known method (Synthesis, p. 388 (1988)). Derivatives of the dipyridine-fused benzoquinone can be synthesized by subjecting the dipyridine-fused benzoquinone to, for example, a known alkylating reaction or coupling reaction. Compounds that may be used as the reagent in known alkylating reactions or as the substrate in known coupling reactions include methyl iodide, propargyl halides, chloromethylstyrene and trimethyloxonium tetrafluoroborate.

Examples of methods for synthesizing dipyridine-fused benzoquinone skeleton-containing polymers which include recurring units of formula (2) and/or (3) are described.

First, as shown in Scheme A below, an epihalohydrin is subjected to ring-opening polymerization in a solvent, thereby synthesizing a polymer having a backbone made up of recurring units of formula (8). Alternatively, a commercially available polyepihalohydrin may be used.

Scheme A

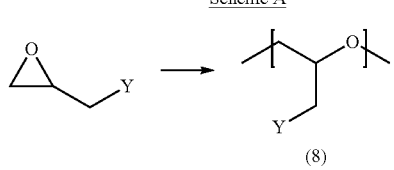

(8)

Here, Y is as defined above.

This ring-opening polymerization may be carried out by a method known to the art. Regioisomers that form as by-products during synthesis may be present within the reaction product. Alternatively, a commercial product may be used as the polymer containing recurring units of formula (8). Purification by precipitation may be carried out on the commercial product in order to increase the purity.

Dipyridine-fused benzoquinone skeleton-containing polymers containing recurring units of formula (2) and/or (3) and recurring units of formula (8) can be synthesized by reacting a polymer containing recurring units of formula (8) with a dipyridine-fused benzoquinone of formula (1) or a derivative thereof in a solvent. The dipyridine-fused benzoquinone of formula (1) or derivative thereof may be of one type used alone or may be of two or more types used in combination.

For example, a dipyridine-fused benzoquinone skeleton-containing polymer containing recurring units of formula (2-2) and recurring units of formula (8) can be synthesized by, as shown in Scheme B below, reacting a polymer made up of recurring units of formula (8) with a dipyridine-fused benzoquinone derivative of formula (1-2) in a solvent. Scheme B shows, by way of illustration only, a case where, in formulas (1-2) and (2-2), $R^1$ and $R^{22}$ are methyl groups and $R^{10}$ to $R^{15}$ and $R^{29}$ to $R^{34}$ are hydrogen atoms.

Scheme B

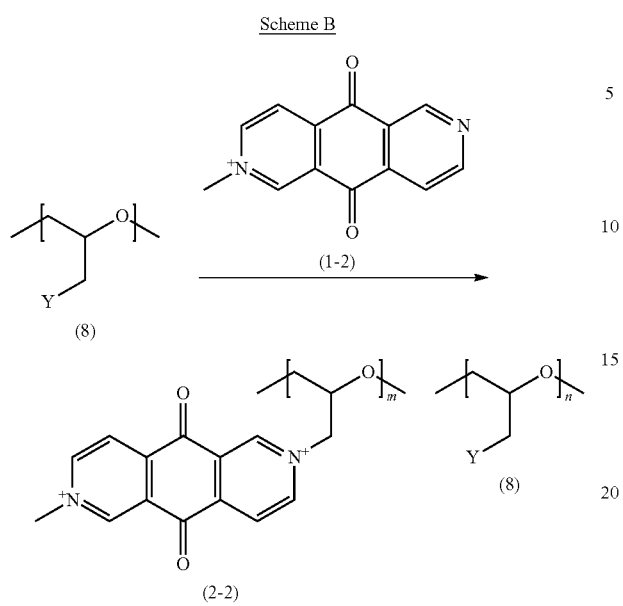

(2-2)

Here, Y is as defined above. The letters m and n are positive numbers which represent the contents (molar ratios) of the recurring units and satisfy the conditions $0.01 \leq m \leq 1.0$, $0 \leq n \leq 0.99$ and $0.01 \leq m+n \leq 1.0$.

A dipyridine-fused benzoquinone skeleton-containing polymer which includes recurring units of formula (2-1), recurring units of formula (3-1) and recurring units of formula (8) can be synthesized by, as shown in Scheme C below, reacting a polymer made up of recurring units of formula (8) with a dipyridine-fused benzoquinone of formula (1-1) in a solvent. Scheme C shows, by way of illustration only, a case in which $R^4$ to $R^9$ in formula (1-1), $R^{23}$ to $R^{28}$ in formula (2-1) and $R^{35}$ to $R^{40}$ in formula (3-1) are hydrogen atoms.

Scheme C

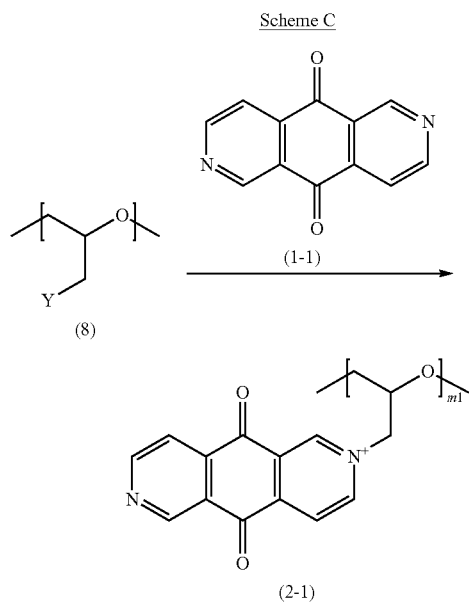

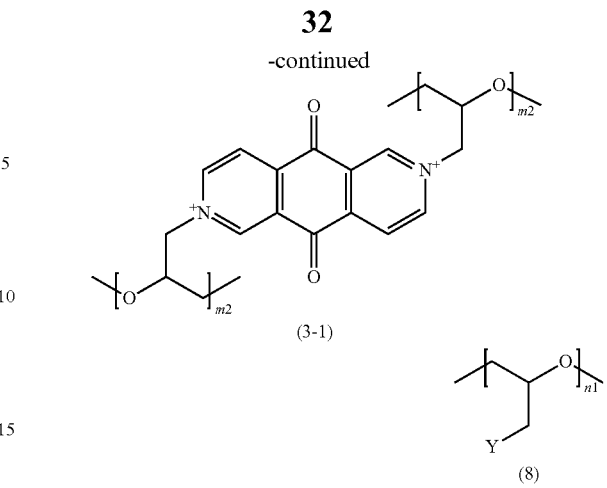

Here, Y is as defined above. The letters m1, m2 and n1 are positive numbers which represent the contents (molar ratios) of the recurring units and satisfy the conditions $0<m1<1.0$, $0<m2<1.0$, $0 \leq n1 \leq 0.99$, $0.01 \leq m1+m2 \leq 1.0$ and $0.01 \leq m1+m2+n1 \leq 1.0$.

A polymer containing only recurring units of formula (2) or (3) can be synthesized by reacting the dipyridine-fused benzoquinone or a derivative thereof in a molar amount that is the same as or greater than the molar amount of the recurring units of formula (8). Alternatively, unsubstituted alkyl halide-substituted ethylene oxide moieties can be left on the polymer by reacting the dipyridine-fused benzoquinone or a derivative thereof in a molar amount that is smaller than the molar amount of the recurring units of formula (8).

When synthesizing a polymer which includes only recurring units of formula (2) or (3), the dipyridine-fused benzoquinone of formula (1) or a derivative thereof is used in an amount of preferably from 1 to 10 moles, more preferably from 1 to 5 moles, and even more preferably from 1 to 2 moles, per mole of recurring units of formula (8). When synthesizing a polymer containing recurring units of formula (8) in addition to recurring units of formula (2) or (3), the dipyridine-fused benzoquinone of formula (1) or a derivative thereof is used in an amount of preferably from 0.01 to 1 moles, more preferably from 0.1 to 0.9 moles, and even more preferably from 0.5 to 0.8 moles, per mole of recurring units of formula (8).

The solvents used in the reactions shown in Schemes B and C are not particularly limited, provided they do not impart an adverse effect on the reaction and they have sufficient solvency with respect to both the reagents used in synthesis and the product of synthesis. Examples of solvents that can be used include dichloromethane, 1,2-dichloroethane, toluene, xylene, chlorobenzene, o-dichlorobenzene, ethyl acetate, methanol, ethanol, tetrahydrofuran (THF), dioxane, dimethylformamide (DMF), dimethylacetamide (DMAc), N-methyl-2-pyrrolidone (NMP), water and acetonitrile.

In the reaction shown in Scheme B or C, the reaction temperature is generally from about 20° C. to about 100° C., and preferably from 75° C. to 100° C. The reaction time is generally from about 1 hour to about 1,000 hours, and preferably from 20 to 72 hours.

When recurring units of formula (9) are to be included in addition to recurring units of formula (2) or (3), compounds such as hexamethylenediamine or polystyreneimine may be reacted with the polymer obtained by the reaction shown in Scheme B or C. At this time, such compounds to be reacted are used in an amount of preferably from 0 to 0.1 mole, more preferably from 0 to 0.05 mole, and even more preferably from 0 to 0.01 mole, per mole of recurring units of formula (8").

The reaction conditions used at this time, such as the solvent, reaction temperature and reaction time, may be the same as those mentioned for the reaction shown in Scheme B or C.

Next, methods for synthesizing dipyridine-fused benzoquinones of formula (4), derivatives thereof, and dipyridine-fused benzoquinone skeleton-containing polymers which include recurring units of formula (5) and/or (6) are described.

The dipyridine-fused benzoquinone of formula (4) may be a commercial product or may be synthesized while referring to *Organic Letter*, 6, p. 1091 (2004). Derivatives of the dipyridine-fused benzoquinone can be synthesized by subjecting the dipyridine-fused benzoquinone to, for example, a known alkylating reaction or coupling reaction. Compounds that may be used as the reagent in known alkylating reaction reagents or as the substrate in known coupling reactions include methyl iodide, propargyl halides, chloromethylstyrene and trimethyloxonium tetrafluoroborate.

Examples of methods for synthesizing dipyridine-fused benzoquinone skeleton-containing polymers which include recurring units of formula (5) and/or (6) (wherein A is —$CH_2$—) are described.

First, as shown in Scheme D below, an allyl compound is polymerized, thereby synthesizing a polymer having a backbone made up of recurring units of formula (8").

Scheme D

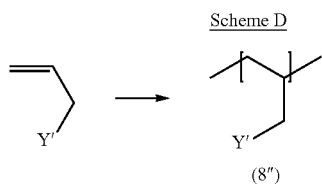

(8")

Here, Y' is as defined above.

The polymerization process used here, although not particularly limited, may be, for example, radical polymerization, anionic polymerization or cationic polymerization. The polymerization conditions may be the same as those customarily used in known methods. Alternatively, a commercial product may be used as the polymer made up of recurring units of formula (8"). The commercial product may be purified by precipitation so as to increase the level of purity.

Dipyridine-fused benzoquinone skeleton-containing polymers which include recurring units of formula (5) and/or (6) and recurring units of formula (8") can be synthesized by reacting a polymer which includes recurring units of formula (8") with a dipyridine-fused benzoquinone of formula (4) or a derivative thereof in a solvent. The dipyridine-fused benzoquinone of formula (1) or a derivative thereof used at this time may be of a single type or may be a combination of two or more types.

For example, as shown in Scheme E below, a dipyridine-fused benzoquinone skeleton-containing polymer which includes recurring units of formula (5-1) and recurring units of formula (8") can be synthesized by reacting a polymer made up of recurring units of formula (8") with a dipyridine-fused benzoquinone derivative of formula (4-1') in a solvent.

Scheme E

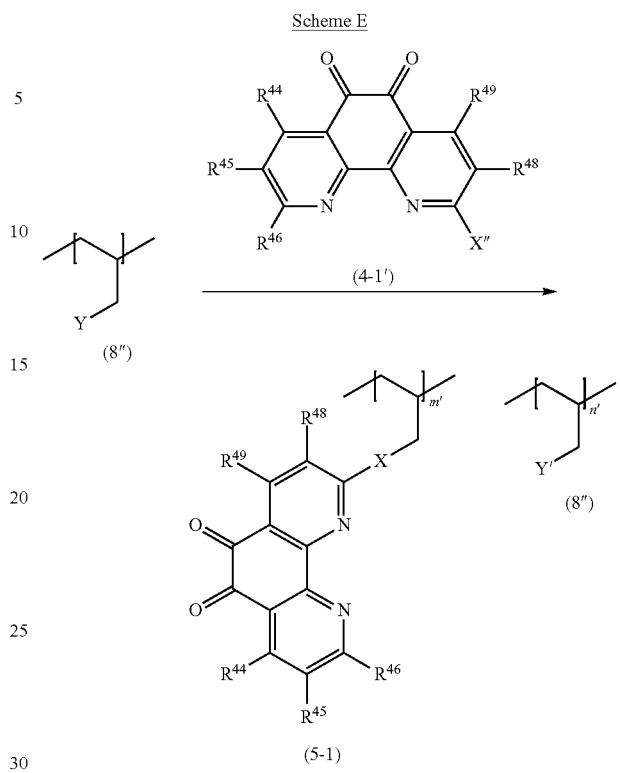

Here, $R^{44}$ to $R^{49}$ are as defined above, and X" is a group capable of reacting with Y' to form X.

In these formulas, m' and n' are positive numbers which represent the contents (molar ratios) of the recurring units and satisfy the conditions $0.01 \leq m' \leq 1.0$, $0 \leq n' \leq 0.99$ and $0.01 \leq m'+n' \leq 1.0$.

A polymer containing only recurring units of formula (5) or (6) can be synthesized by reacting the dipyridine-fused benzoquinone or a derivative thereof in a molar amount that is the same as or greater than the molar amount of the recurring units of formula (8"). Alternatively, unsubstituted alkyl halide-substituted ethylene oxide moieties can be left on the polymer by reacting the dipyridine-fused benzoquinone or a derivative thereof in a molar amount that is smaller than the molar amount of the recurring units of formula (8").

When synthesizing a polymer which includes only recurring units of formula (5) or (6), the dipyridine-fused benzoquinone of formula (4) or a derivative thereof is used in an amount of preferably from 1 to 10 moles, more preferably from 1 to 5 moles, and even more preferably from 1 to 2 moles, per mole of recurring units of formula (8"). When synthesizing a polymer which includes also recurring units of formula (8") in addition to recurring units of formula (5) or (6), the dipyridine-fused benzoquinone of formula (4) or a derivative thereof is used in an amount of preferably from 0.01 to 1 moles, more preferably from 0.1 to 0.9 moles, and even more preferably from 0.5 to 0.8 moles, per mole of recurring units of formula (8").

The solvent used in the reaction shown in Scheme E is not particularly limited, provided it does not impart an adverse effect on the reaction and it has sufficient solvency with respect to both the reagents used in synthesis and the product of synthesis. Examples of solvents that can be used include dichloromethane, 1,2-dichloroethane, toluene, xylene, chlorobenzene, o-dichlorobenzene, ethyl acetate, methanol, ethanol, tetrahydrofuran (THF), dioxane, dimethylformamide (DMF), dimethylacetamide (DMAc), N-methyl-2-pyrrolidone (NMP), water and acetonitrile.

In the reaction shown in Scheme E, the reaction temperature is generally from about 20° C. to about 100° C., and preferably from 75° C. to 100° C. The reaction time is generally from about 1 hour to about 1,000 hours, and preferably from 20 to 72 hours.

Polymers which include recurring units of formula (7) can be synthesized by, for example, reacting a compound of formula (4) with a compound of formula (10) in a solvent.

Here, X' is as defined above and Hal is a halogen atom.

Of these, polymers which include recurring units of formula (7-1) can be synthesized by, as shown in Scheme F below, reacting a compound of formula (4-1') with a compound of formula (10) in a solvent.

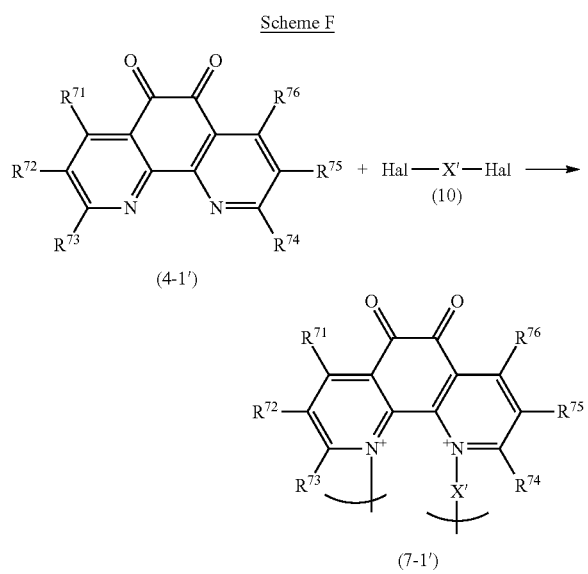

Here, $R^{71}$ and $R^{76}$, X' and Hal are as defined above.

In the reaction shown in Scheme F, the compound of formula (10) is used in an amount of preferably from 0.5 to 5 moles, more preferably from 0.5 to 2.5 moles, and even more preferably from 1 to 2 moles, per mole of recurring units of formula (4-1').

The solvent used in the reaction shown in Scheme F is not particularly limited, provided it does not impart an adverse effect on the reaction and it has sufficient solvency with respect to both the reagents used in synthesis and the product of synthesis. Examples of solvents that can be used include dichloromethane, 1,2-dichloroethane, toluene, xylene, chlorobenzene, o-dichlorobenzene, ethyl acetate, methanol, ethanol, tetrahydrofuran (THF), dioxane, dimethylformamide (DMF), dimethylacetamide (DMAc), N-methyl-2-pyrrolidone (NMP), water and acetonitrile.

In the reaction shown in Scheme F, the reaction temperature is generally from about 25° C. to about 100° C., and preferably from 80° C. to 100° C. The reaction time is generally from about 10 hours to about 50 hours, and preferably from 20 to 30 hours.

To minimize dissolution in the electrolyte solution, the dipyridine-fused benzoquinone skeleton-containing polymers of the invention have a weight-average molecular weight (Mw) of preferably at least 1,000, more preferably at least 100,000, and even more preferably at least 500,000. To ensure solubility in the subsequently described electrode slurry-forming solvent, the molecular weight is preferably not more than 5,000,000, more preferably not more than 3,000,000, and even more preferably not more than 2,000,000. In this invention, Mw refers to the polystyrene-equivalent weight-average molecular weight measured by gel permeation chromatography (GPC).

Secondary Battery

The secondary battery of the invention is characterized by using either of the foregoing charge storage materials as an electrode active material. Other constituent members of the battery cell may be suitably selected from among conventional known members and used.

An ordinary secondary battery is explained here by way of illustration.

A secondary battery is generally composed of a positive electrode layer, a negative electrode layer, a separator layer situated between the positive electrode layer and the negative electrode layer, and an electrolyte solution that fills the interior of the cell containing all of these elements. The positive electrode layer and negative electrode layer are each formed, on a substrate that is a current collector, as a thin-film which includes an electrode active material, an optional conductive additive of carbon or the like for enhancing the conductivity of the electrode layer, and an optional binder for enhancing the uniformity of film formation, increasing ionic conductivity and minimizing dissolution in the electrolyte solution. The electrolyte solution is composed of an electrolyte made of a salt that serves as the ion conductor, a solvent and the like.

The charge storage material of the invention is used as the electrode active material in this positive electrode layer or negative electrode layer. There is no particular limitation on which of the electrode layers—the positive electrode layer or the negative electrode layer—in which to use the electrode active material, this being determined according to whether the corresponding electrode has a noble potential or a base potential. Alternatively, this electrode active material may be used in both electrodes.

The form of the secondary battery and the types of electrode active material and electrolyte solution are not particularly limited. Use may be made of, for example, any of the following: lithium ion batteries, nickel-hydrogen batteries, manganese batteries, and air batteries. Nor are there any particular limitations on the lamination method and the production method.

The electrode layer can be produced by mixing together the charge storage material of the invention, a solvent and, optionally, a conductive additive, a binder and other electrode active materials known to the art so as to prepare an electrode slurry, and using this slurry to form a thin-film on a substrate. The method of forming the thin-film is not particularly limited; use can be made of various hitherto known methods. Illustrative examples include various printing methods, such as offset printing, screen printing and gravure printing, and also dip coating, spin coating, bar coating, slit (die) coating and inkjet printing methods that use a solution, suspension or slurry obtained by dissolving or suspending a material containing the charge storage material of the invention in a solvent.

Illustrative examples of the current collector used as the material underlying the electrode layer include metal foils or substrates of aluminum, copper, lithium, stainless steel, iron, chromium, platinum, gold or the like; alloy foils or substrates composed of any combination of these metals; oxide substrates such as indium-tin oxide (ITO), indium-zinc oxide (IZO) and antimony-tin oxide (ATO); carbon substrates such as glassy carbon, pyrolytic graphite and carbon felt; and carbon-coated foils such as metal foils coated with a carbon material.

Illustrative examples of the conductive additive include carbon materials such as graphite, carbon black, acetylene black, vapor-grown carbon fibers (VGCF), carbon nanotubes, carbon nanohorns and graphene; and electrically conductive polymers such as polyaniline, polypyrrole, polythiophene, polyacetylene and polyacene. A single type of conductive additive may be used alone or two or more types may be used in combination.

Illustrative examples of the binder include polytetrafluoroethylene, polyvinylidene fluoride, polyhexafluoropropylene, vinylidene fluoride-hexafluoropropylene copolymer, polyvinyl chloride, polycarbonate, polystyrene, polyacrylic acid, polyacrylic acid salts, polyacrylic acid esters, polymethacrylic acid, polymethacrylic acid salts, polymethacrylic acid esters, polyester, polysulfone, polyphenylene oxide, polybutadiene, poly(N-vinylcarbazole), hydrocarbon resins, ketone resins, phenoxy resins, polyamide, ethyl cellulose, vinyl acetate, ABS resins, SBR resins, polyurethane resins, melamine resins, unsaturated polyester resins, alkyd resins, epoxy resins, silicone resins, and copolymers or polymer blends composed of any combination of these.

Illustrative examples of the electrode slurry-forming solvent include NMP, dimethylsulfoxide, ethylene carbonate, propylene carbonate, dimethyl carbonate, diethyl carbonate, methyl ethyl carbonate, γ-butyrolactone, THF, dioxolane, sulfolane, DMF and DMAc.

When an electrode active material containing the charge storage material of the invention is used in the positive electrode layer, the negative electrode active material included in the negative electrode layer is exemplified by carbon materials such as graphite, carbon black, acetylene black, vapor-grown carbon fibers (VGCF), carbon nanotubes, carbon nanohorns and graphene; lithium and lithium alloys such as Li—Al, Li—Si and Li—Sn; and silicon, SiO, $SiO_2$, Si—$SiO_2$ composites, tin, SnO, $SnO_2$, PbO, $PbO_2$, GeO, $GeO_2$, $WO_2$, $MoO_2$, $Fe_2O_3$, $Nb_2O_5$, $TiO_2$, $Li_4Ti_5O_{12}$ and $Li_2Ti_3O_7$. When an electrode active material containing the charge storage material of the invention is used in the negative electrode layer, it may also be used together with these negative electrode active materials.

When the charge storage material-containing electrode active material of the invention is used in a negative electrode layer, the positive electrode active material included in the positive electrode layer is exemplified by organic electrode active materials such as nitroxy radical-containing compounds, organosulfur polymers, quinone polymers other than the charge storage material of the invention, quinoid materials, dione materials and rubeanic acid materials; and inorganic electrode active materials such as $LiCoO_2$, $LiMn_2O_4$, $LiNiO_2$, $LiNi_{0.5}Mn_{0.5}O_2$, $LiFePO_4$, $LiMnPO_4$, $LiCoPO_4$, $Fe_2(SO_4)_3$, $LiMnSiO_4$ and $V_2O_5$. When the charge storage material-containing electrode active material of the invention is used in the positive electrode layer, it may also be used together with these positive electrode active materials.

The charge storage material-containing electrode active material of the invention may be used as an air electrode (positive electrode) in an air battery. In such cases, in addition to the above-mentioned negative electrode active materials, sodium, magnesium, aluminum, calcium, zinc or the like may be used as a negative electrode active material included within the negative electrode layer.

In cases where a positive electrode is used as the air electrode in an air battery, in addition to the charge storage material of the invention, an inorganic material such as manganese oxide or a nitroxy radical-containing material such as a TEMPO polymer may be concomitantly used as a redox auxiliary within the positive electrode layer.

The thickness of the electrode layer, although not particularly limited, is preferably from about 0.0.01 μm to about 1,000 μm, and more preferably from about 0.1 μm to about 100 μm.

The material used in the separator layer is exemplified by porous polyolefins, polyamides and polyesters.

The electrolyte in the electrolyte solution is exemplified by lithium salts such as $LiPF_6$, $LiBF_4$, $LiN(C_2F_5SO_2)_2$, $LiAsF_6$, $LiSbF_6$, $LAlF_4$, $LiGaF_4$, $LiInF_4$, $LiClO_4$, $LiN(CF_3SO_2)_2$, $LiCF_3SO_3$, $LiSiF_6$ and $LiN(CF_3SO_2)(C_4F_9SO_2)$; metal iodides such as LiI, NaI, KI, CsI and $CaI_2$; iodide salts of quaternary imidazolinium compounds, iodide salts and perchlorate salts of tetraalkylammonium compounds; and metal bromides such as LiBr, NaBr, KBr, CsBr and $CaBr_2$.

Use can also be made of solid electrolytes such as polyethylene oxide materials, thio-LISICON materials such as $Li_2S$—$P_2SS$, and polymer compounds obtained by polymerizing or copolymerizing monomers such as hexafluoropropylene, tetrafluoroethylene, trifluoroethylene, ethylene, propylene, acrylonitrile, vinylidene chloride, acrylic acid, methacrylic acid, methyl acrylate, ethyl acrylate, methyl methacrylate, styrene and vinylidene fluoride.

The solvent in the electrolyte solution is not particularly limited, provided it is one that dissolves the electrolyte without degrading battery performance by causing corrosion or decomposition of the materials making up the battery. Illustrative examples include nonaqueous solvents, including ethylene carbonate, propylene carbonate, butylene carbonate, cyclic esters such as γ-butyrolactone, ethers such as THF and dimethoxyethane, and acyclic esters such as dimethyl carbonate, diethyl carbonate and ethyl methyl carbonate. These solvents may be used singly or two or more may be used in admixture.

EXAMPLES

Synthesis Examples, Working Examples of the invention and Comparative Examples are given below by way of illustration, although the invention is not limited by these Examples. The instruments and measurement conditions used were as follows.
(1) $^1$H-NMR
ECX-500 Nuclear Magnetic Resonance Spectrometer from JEOL Ltd. (solvent, $CDCl_3$; internal standard, TMS)
(2) $^{13}$C-NMR
ECX-500 Nuclear Magnetic Resonance Spectrometer from JEOL Ltd. (solvent, $CDCl_3$; internal standard, TMS)
(3) $^{13}$C-CP/MAS NMR
ECA-400 Nuclear Magnetic Resonance Spectrometer from JEOL Ltd.
(4) GC-MS
JMS-GCMATE II, a gas chromatograph mass spectrometer from JEOL Ltd.
(5) MALDI-TOFMS
Autoflex III, a MALDI-TOF mass spectrometer from Bruker Daltonics
(6) Elemental Analysis
PE2400 Series II Elemental Analyzer from Perkin Elmer (7) Cyclic Voltammetry ALS Dual Electrochemical Analyzer, from BAS Inc.

(8) Evaluation of Battery Characteristics

HJ1001SD8, a 16-channel battery charge/discharge measurement system, from Hokuto Denko Corporation

[1] Synthesis of Dipyridine-Fused Benzoquinone and Derivatives Thereof

Example 1: Synthesis of Dipyridine-Fused Benzoquinone

Dipyridine-fused benzoquinone was synthesized by the following scheme.

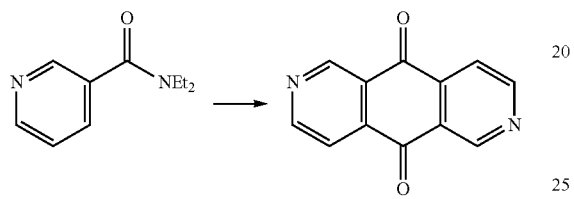

Hexamethylphosphoric triamide (6 mL) and 70 mL of tetrahydrofuran (THF) were added to a 500 mL round-bottomed flask under an argon atmosphere, and the flask was tightly stoppered. This was cooled to −78° C. in a dry ice-methanol bath, following which 27 mL (54 mmol, 3.0 eq.) of lithium diisopropylamide (as a 2.0 mol/L solution in THF/heptane/ethyl benzene) was added and the flask contents were stirred at −78° C. for 30 minutes. Next, a THF (5 mL) solution of 3.2 mL (18 mmol, 1.0 eq.) of N,N-diethyl-nicotinamide prepared in an argon atmosphere was added one drop at a time with a syringe. The temperature was returned to room temperature and the reaction was carried out for 20 hours, following which 100 mL of pure water was added to stop the reaction. The THF was distilled off under reduced pressure in an evaporator, and the product was extracted with dichloromethane and an aqueous solution of sodium chloride using a separatory funnel. After washing with hexane, purification was carried out with a silica gel column using diethyl ether/dichloromethane (3/7 by volume) as the eluting solvent. Recrystallization from chloroform/hexane (1/20 by volume) and vacuum drying gave 1.89 g (9.0 mmol) of a sand-colored solid (yield, 50%).

$^1$H-NMR (CDCl$_3$, 500 MHz, ppm):

σ=9.59 (d, 2H), 9.19 (d, 2H), 8.11 (dd, 2H)

$^{13}$C-NMR (CDCl$_3$, 500 MHz, ppm):

σ=182.1, 156.4, 149.9, 138.0, 125.8, 119.1

Mass: m/z=211.0 (found), 210.0 (calculated).

Elemental analysis:

(found) C, 68.4%; H, 2.7%; N, 13.3%, (calculated) C, 68.6%; H, 2.9%; N, 13.3%.

Example 2: Synthesis of Dipyridine-Fused Benzoquinone Derivatives

Dipyridine-Fused Benzoquinone Derivatives A and B were synthesized by the following scheme.

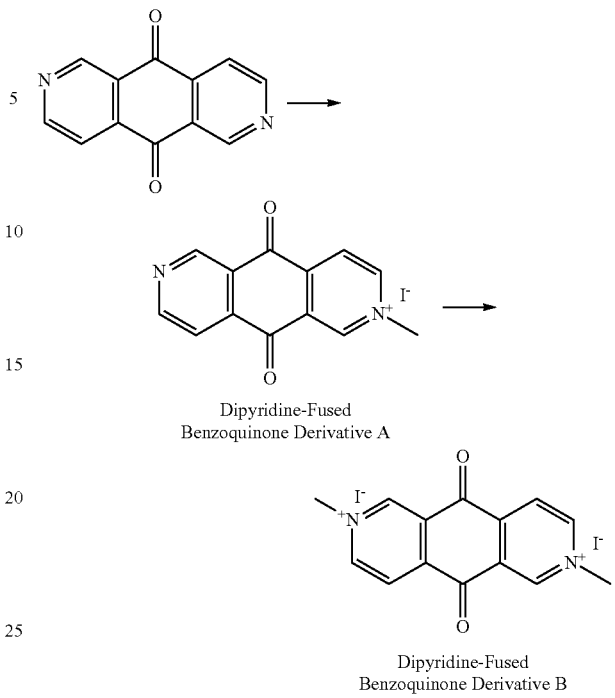

Dipyridine-fused benzoquinone (200 mg, 0.95 mmol, 1.2 eq.) and 15 mL of acetonitrile were added to a 100 mL round-bottomed flask and dissolved under heating at 75° C. To this was added 49.4 μL (0.79 mmol, 1.0 eq.) of methyl iodide one drop at a time by syringe, and reaction was carried out for 2 hours. After reaction completion, the acetonitrile was distilled off under reduced pressure in an evaporator, following which the product was washed with dichloromethane and vacuum dried, giving 251 mg (0.71 mmol) of Dipyridine-Fused Benzoquinone Derivative A as a blackish-green solid (yield, 90%).

$^1$H-NMR (CDCl$_3$, 500 MHz, ppm):

σ=9.81 (s, 1H), 9.55 (s, 1H), 9.34 (brs, 1H), 9.20 (brs, 1H), 8.79 (d, 1H), 8.26 (d, 1H), 4.63 (s, 3H)

Mass: m/z=225.1 (found), 225.1 (calculated)

Dipyridine-Fused Benzoquinone Derivative A (100 mg, 0.28 mmol, 1.0 eq.) and 10 mL of DMF were added to a 30 mL flask and dissolved under heating at 100° C. Next, 275 μL (2.8 mmol, 10 eq.) of methyl iodide was added and the reaction was carried out at 100° C. for 20 hours. Following reaction completion, the precipitated solid was recovered by filtration and then purified by recrystallization from 80*C water, giving 69 mg (0.14 mmol) of Dipyridine-Fused Benzoquinone Derivative B as a purple solid (yield, 50%).

Mass: m/z=493.8 (found), 247.0 (calculated)

Example 3: Synthesis of Dipyridine-Fused Benzoquinone Derivatives

Dipyridine-Fused Benzoquinone Derivatives C and D were synthesized by the following scheme.

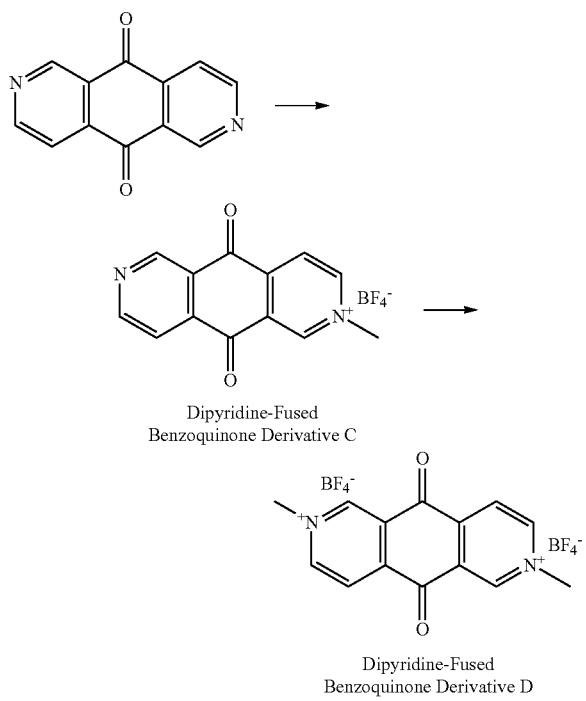

Dipyridine-Fused Benzoquinone Derivative C

Dipyridine-Fused Benzoquinone Derivative D

Dipyridine-fused benzoquinone (300 mg, 1.43 mmol, 1.2 eq.) and 20 mL of nitromethane were added to a 50 mL round-bottomed flask and dissolved under heating at 40° C. While stirring this solution in a nitrogen atmosphere or in open air, a nitromethane solution (3 mL) of 176 mg (1.19 mmol, 1.0 eq.) of trimethyloxonium tetrafluoroborate was added one drop at a time, and the reaction was carried out at 40° C. for 30 minutes. After reaction completion, the product was concentrated under reduced pressure in an evaporator, purified by precipitation in diethyl ether, purified by recrystallization from 80° C. water and vacuum dried, giving 130 mg (0.41 mmol) of Dipyridine-Fused Benzoquinone Derivative C as a yellowish-green solid (yield, 29%).

$^1$H-NMR (CD$_3$CN, 500 MHz, ppm):

σ=9.57 (s, 1H), 9.52 (s, 1H), 9.26 (d, 1H),
9.08 (d, 1H), 8.67 (d, 1H), 8.14 (d, 1H),
2.14 (s, 1H), 1.95-1.93 (m, 2H)
Mass: m/z=224.7 (found), 225.1 (calculated)

Dipyridine-fused benzoquinone (300 mg, 1.43 mmol, 1.0 eq.) and 20 mL of nitromethane were added to a 50 mL flask and dissolved under heating at 40° C. While stirring this solution in a nitrogen atmosphere or in open air, a nitromethane solution (10 mL) of 630 mg (4.29 mmol, 3.0 eq.) of trimethyloxonium tetrafluoroborate was added in a dropwise manner, and the reaction was carried out at 40° C. for 30 minutes. After reaction completion, the product was concentrated under reduced pressure in an evaporator, purified by precipitation in diethyl ether, purified by recrystallization from 80° C. water and vacuum dried, giving 227 mg (0.55 mmol) of Dipyridine-Fused Benzoquinone Derivative D as a light pink-colored solid (yield, 38%).

$^1$H-NMR (CD$_3$OH, 500 MHz, ppm):

σ=9.62 (s, 1H), 9.24 (d, 1H),
8.62 (d, 1H), 8.45 (s, 1H), 6.48 (d, 1H),
5.96 (d, 1H) (aromatic region)
Mass: m/z=271.1 (found),
271.0 (calculated: [compound D-HBF$_4$]$^+$)

Example 4: Synthesis of Dipyridine-Fused Benzoquinone Derivative

Dipyridine-Fused Benzoquinone Derivative E was synthesized by the following scheme.

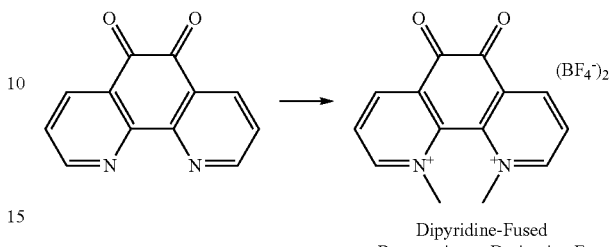

Dipyridine-Fused Benzoquinone Derivative E

The following were added to a 30 mL round-bottom flask and dissolved under heating at 40° C.: 100 mg (0.48 mmol, 1.0 eq.) of 1,10-phenanthrolin-5,6-dione (Sigma-Aldrich) and 10 mL of nitromethane. Next, a nitromethane solution (5 mL) of 210 mg (1.42 mmol, 3.0 eq.) of trimethyloxonium tetrafluoroborate was added dropwise under stirring in a nitrogen atmosphere or in open air, and reaction was carried out for 1 hour at 40° C. After reaction completion, purification by precipitation in diethyl ether, purification by recrystallization from 40° C. water, and vacuum drying gave 25 mg (0.03 mmol) of Dipyridine-Fused Benzoquinone Derivative E as a yellowish-brown solid (yield, 6%).

[2] Synthesis of Dipyridine-Fused Benzoquinone Skeleton-Containing Polymers

Example 5: Synthesis of Dipyridine-Fused Benzoquinone Skeleton-Containing Polymer A Dipyridine-Fused Benzoquinone Skeleton-Containing Polymer A was synthesized by the following scheme.

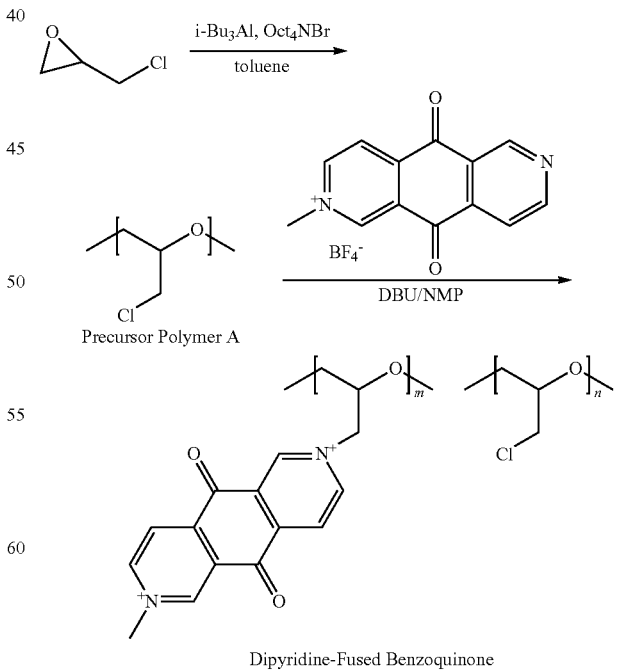

Dipyridine-Fused Benzoquinone Skeleton-Containing Polymer A

First, 38 mg (0.32 mmol, 1.0 eq.) of polyepichlorohydrin (from Sigma-Aldrich; weight-average molecular weight, 700,000), which was purified by precipitation in benzene-methanol solvent and vacuum dried, and 10 mL of acetonitrile were added to a 30 mL round-bottomed flask and dissolved under heating at 75° C. To this was added 100 mg (0.32 mmol, 1.0 eq.) of Dipyridine-Fused Benzoquinone Derivative C, and the reaction was carried out for 60 hours under heating and refluxing. After reaction completion, the product was concentrated under reduced pressure in an evaporator, purified by precipitation in diethyl ether and vacuum dried, giving a blackish-green solid (Polymer A). As a result of electrochemical measurement, the values of m and n in the above scheme were m=0.5 and n=0.5.

Example 6: Synthesis of Dipyridine-Fused Benzoquinone Skeleton-Containing Polymer B Dipyridine-Fused Benzoquinone Skeleton-Containing Polymer B was synthesized by the following scheme.

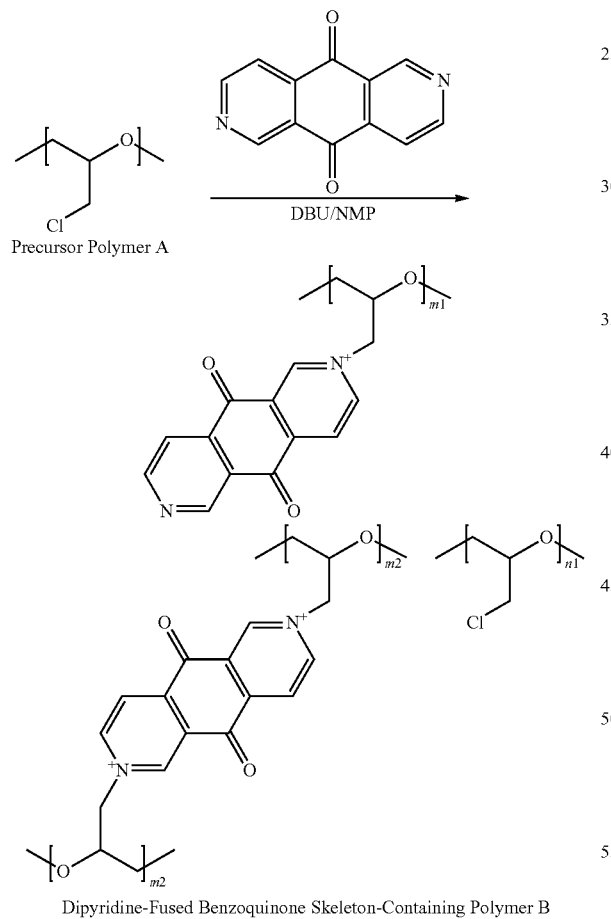

Dipyridine-Fused Benzoquinone Skeleton-Containing Polymer B

Dipyridine-fused benzoquinone (100 mg, 0.48 mmol, 2.0 eq.) and 3 mL of a 5 wt % solution of polyepichlorohydrin in DMF prepared using polyepichlorohydrin (from Sigma-Aldrich; weight-average molecular weight, 700,000) that had been purified by precipitation in benzene-methanol solvent and vacuum dried were added to a 30 mL round-bottomed flask and reacted at 100° C. for 72 hours. After reaction completion, the product was distilled under reduced pressure in an evaporator, then re-dissolved in acetone and purified by precipitation in diethyl ether, giving a blackish-brown solid (Polymer B).

Example 7: Synthesis of Dipyridine-Fused Benzoquinone Skeleton-Containing Polymer C Dipyridine-Fused Benzoquinone Skeleton-Containing Polymer C was synthesized by the following scheme.

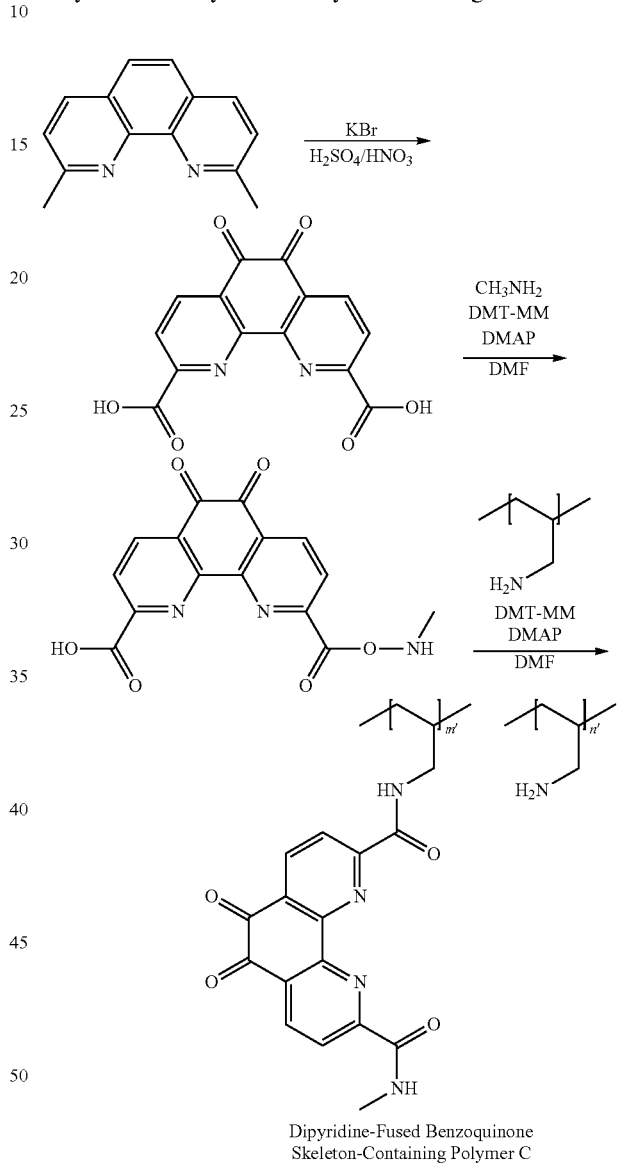

Dipyridine-Fused Benzoquinone Skeleton-Containing Polymer C

The following were added to a 30 mL round-bottomed flask: 200 mg (0.96 mmol, 1.0 eq.) of 2,9-dimethyl-9,10-phenanthroline and 230 mg (1.93 mmol, 2.0 eq.) of potassium bromide. Next, 4 mL of sulfuric acid and 2 mL of nitric acid were slowly added dropwise thereto to effect dissolution, and followed by 15 hours of hot refluxing at 190° C. After reaction completion, the solution was added dropwise to ice water and the solid that settled out was collected by filtration, washed with pure water and vacuum dried, giving 198 mg (0.67 mmol) of 5,6-dioxo-5,6-dihydro-[1,10] phenanthroline-2,9-dicarboxylic acid as a yellow solid (yield, 70%).

The following were added to and dissolved in a 30 mL round-bottomed flask: 300 mg (1 mmol, 1.0 eq.) of 5,6-dioxo-5,6-dihydro-[1,10]phenanthroline-2,9-dicarboxylic acid, 330 mg (1.2 mmol, 1.2 eq.) of 4-(4,6-dimethoxy-1,3,5-triazin-2-yl)-4-methylmorpholinium chloride, 50 mg (0.4 mmol, 0.4 eq.) of 4-dimethylaminopyridine and 10 mL of DMF. Next, 15.6 mg (0.5 mmol, 0.5 eq.) of methylamine was slowly added dropwise and the reaction was carried out for 24 hours at room temperature. After reaction completion, purification by precipitation in acetone and vacuum drying afforded 229 mg (0.74 mmol) of 9-methylcarbonyl-5,6-dioxo-5,6-dihydro-[1,10]phenanthrolin-2-carboxylic acid as a yellowish-green solid (yield, 74%).

The following were added to a 30 mL round-bottomed flask: 100 mg (0.32 mmol, 1.0 eq.) of 9-methylcarbonyl-5,6-dioxo-5,6-dihydro-[1,10]phenanthroline-2-carboxylic acid, polyallylamine (from Nitto Boseki Co., Ltd.; weight-average molecular weight, 25,000), 105 mg (0.38 mmol, 1.2 eq.) of 4-(4,6-dimethoxy-1,3,5-triazin-2-yl)-4-methylmorpholinium chloride, 15.6 mg (0.13 mmol, 0.4 eq.) of 4-dimethylaminopyridine and 10 mL of DMF, and reacted for 24 hours at room temperature. After reaction completion, purification by precipitation in methanol, Soxhlet purification with methanol and vacuum drying yielded 37 mg of Dipyridine-Fused Benzoquinone Skeleton-Containing Polymer C as a brown solid.

Example 8: Synthesis of Dipyridine-Fused Benzoquinone Skeleton-Containing Polymer D Dipyridine-Fused Benzoquinone Skeleton-Containing Polymer D was synthesized by the following scheme.

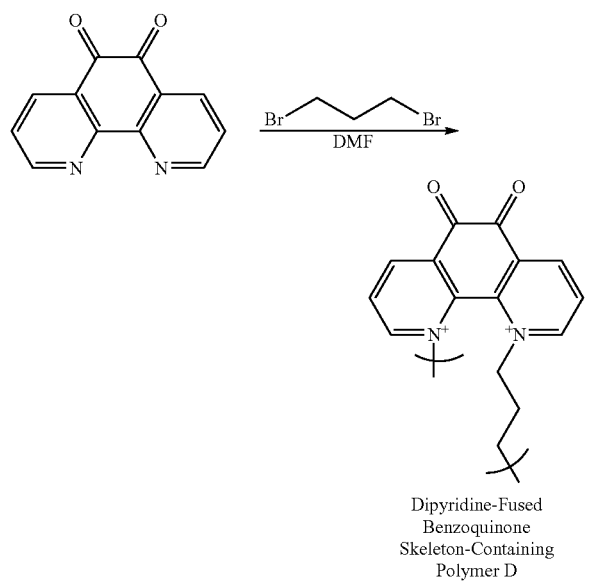

Dipyridine-Fused Benzoquinone Skeleton-Containing Polymer D

The following were added to a 30 mL round-bottomed flask and reacted for 24 hours at 90° C.: 100 mg (0.48 mmol, 1.0 eq.) of 1,10-phenanthrolinequinone, 500 μL (2.3 mmol, 4.8 eq.) of dibromopropane and 5 mL of DMF. After reaction completion, purification by precipitation in acetonitrile, Soxhlet purification with acetonitrile and vacuum drying afforded 54 mg (0.13 mmol) of Dipyridine-Fused Benzoquinone Skeleton-Containing Polymer D as a black solid (yield, 40%).

[3] Evaluation of Electrodes and Batteries Containing Dipyridine-Fused Benzoquinone-Skeleton-Containing Polymers Example 9: Cyclic Voltammetry of Carbon Composite Electrode Produced Using Dipyridine-Fused Benzoquinone Skeleton-Containing Polymer A Cyclic voltammetry was carried out using the beaker cell shown in FIG. 1.

First, 20 mg of carbon powder and 2.5 mg of polyvinylidene fluoride binder dissolved in 120 mg of NMP were added to 2.5 mg of the Dipyridine-Fused Benzoquinone Skeleton-Containing Polymer A synthesized in Example 5, and these ingredients were kneaded in a planetary centrifugal mixer. The mixture obtained by about 20 minutes of mixing was coated onto a glassy carbon substrate, then vacuum-dried under heating at 60° C. for 18 hours, giving a carbon composite electrode 11.

Next, the resulting electrode was immersed in an electrolyte solution, thereby impregnating the electrolyte solution into voids in the electrode. A 1 mol/L solution of lithium perchlorate in γ-butyrolactone was used as the electrolyte solution.

Figure 1:
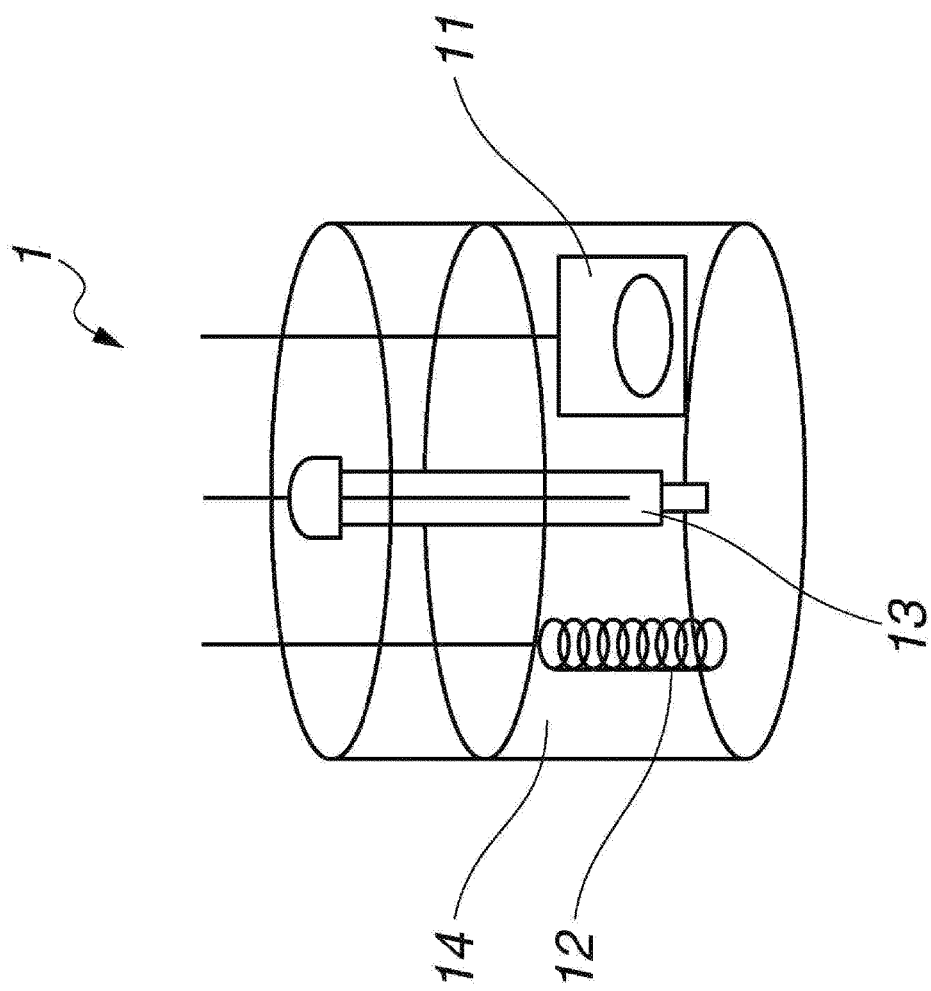
FIG. 1 is a schematic view of a beaker cell produced in the working examples of the invention.

A beaker cell 1 like that shown in FIG. 1 was created by setting this carbon composite electrode 11 as the working electrode, a platinum electrode 12 as the counterelectrode and an Ag/AgCl electrode 13 as the reference electrode within a beaker, and adding therein an electrolyte solution 14 like that described above.

Figure 2:
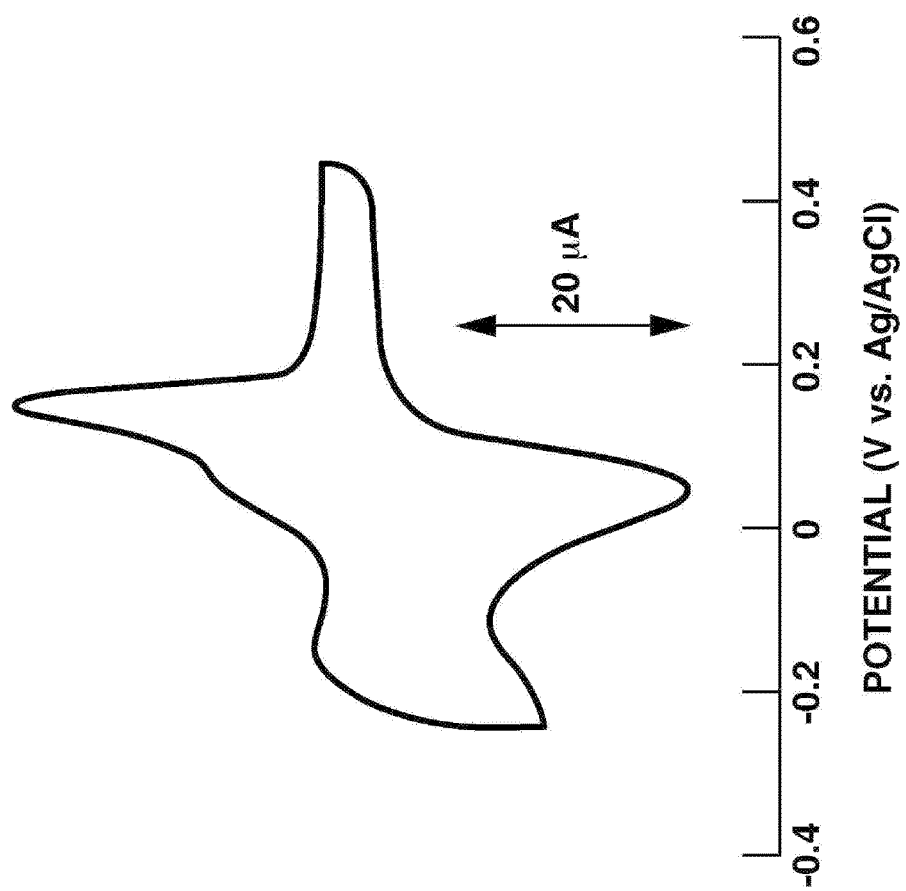
FIG. 2 is a cyclic voltammogram of the carbon composite electrode produced in Example 9.

Using this beaker cell 1, cyclic voltammetry was carried out at a sweep rate of 1 mV/sec. The results are shown in FIG. 2. As shown in FIG. 2, for the carbon composite electrode produced using Dipyridine-Fused Benzoquinone Skeleton-Containing Polymer A, a reversible redox wave appeared at $E_{1/2}$=+0.10 V.

Figure 3:
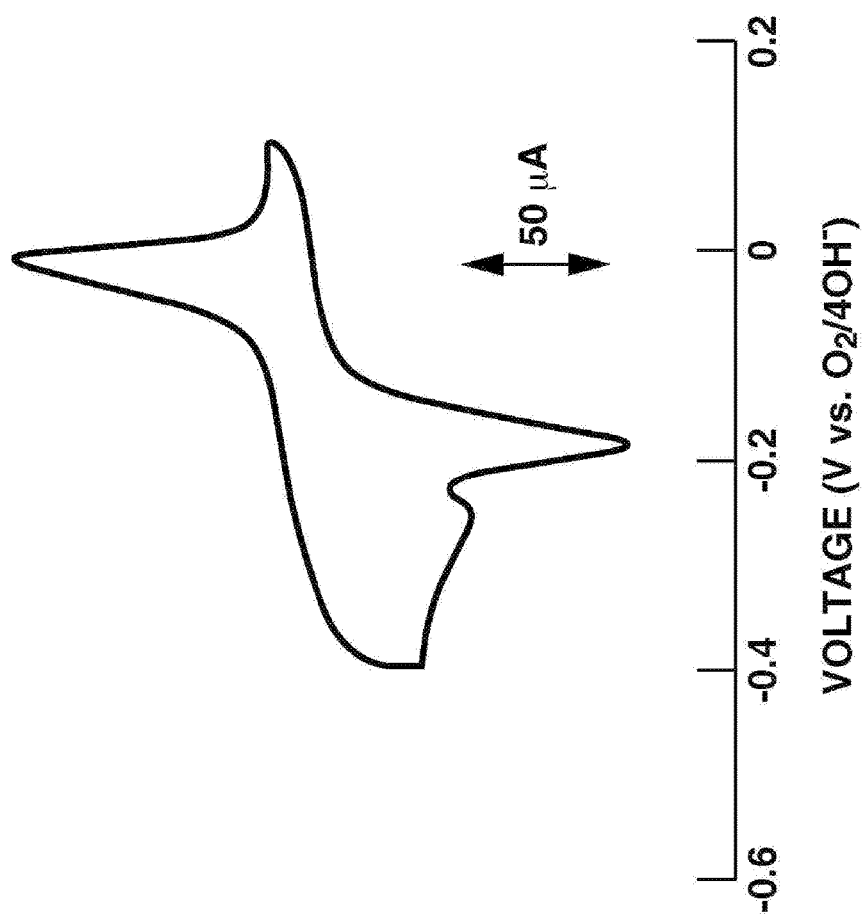
FIG. 3 is a cyclic voltammogram of the carbon composite electrode produced in Example 10.

Example 10: Evaluation of Characteristics of Air Secondary Battery Produced Using Dipyridine-Fused Benzoquinone Skeleton-Containing Polymer B in Electrode An air secondary battery was fabricated by using a carbon composite electrode of Polymer B produced in the same way as above as the negative electrode, an oxygen reduction catalyst (MnOx/Carbon, from Electric Fuel Ltd.) as the positive electrode, a 10 mol/L aqueous NaOH solution as the electrolyte solution, and a glass filter as the separator. Cyclic voltammetry was carried out at a sweep rate of 10 mV/sec. The results are shown in FIG. 3.

Example 11: Evaluation of Characteristics of Lithium Ion Battery Produced Using Dipyridine-Fused Benzoquinone Skeleton-Containing Polymer B in Electrode First, 20 mg of carbon powder and 2.5 mg of polyvinylidene fluoride binder dissolved in 120 mg of NMP were added to 2.5 mg of Polymer B, and these ingredients were kneaded in a planetary centrifugal mixer. The mixture obtained by about 20 minutes of mixing was coated onto aluminum, then vacuum-dried under heating at 60° C. for 20 hours, giving a thin-film electrode.

Next, using the resulting electrode, a battery was assembled as follows. The operations were all carried out in an argon atmosphere.

Figure 4:
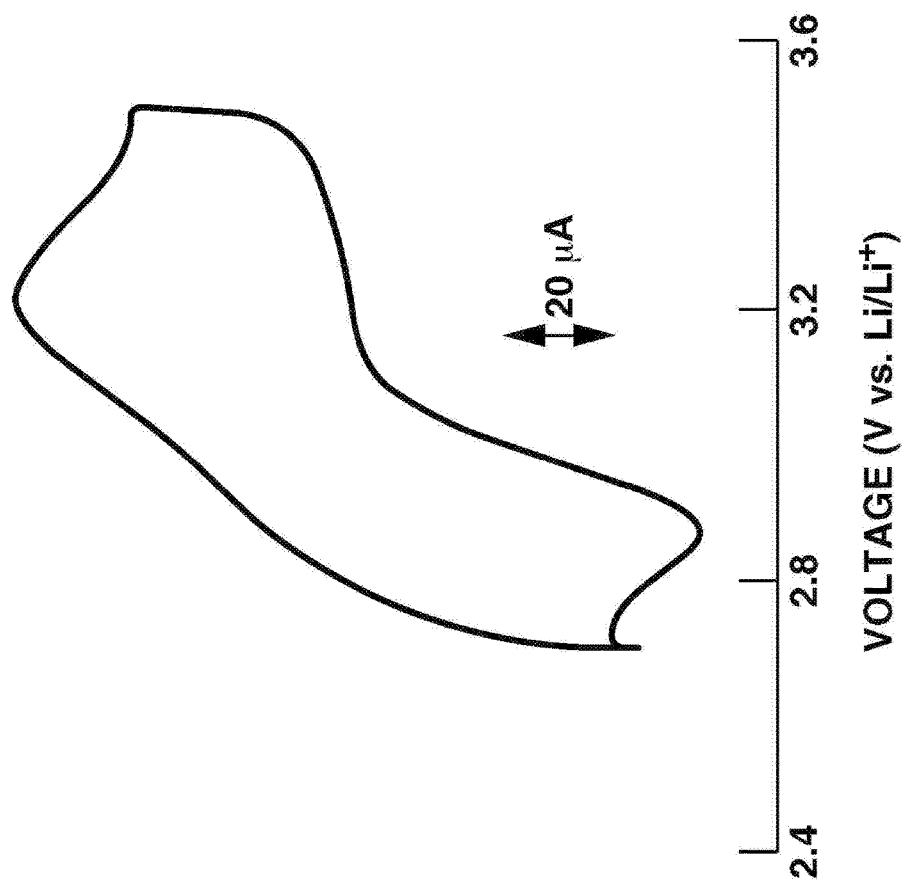
FIG. 4 is a cyclic voltammogram of the carbon composite electrode produced in Example 11.

First, the above electrode was placed on a current collector (battery case), and a 25 nm thick separator composed of Celgard 3501 impregnated with a 1.0 mol/L solution of lithium hexafluorophosphate in ethylene carbonate/diethyl carbonate (1/1 by volume) was placed on top of the electrode. Metallic lithium foil was then stacked thereon, followed in turn by a stainless steel weight, after which a 1.0 mol/L solution of lithium hexafluorophosphate in ethylene carbonate/diethyl carbonate (1/1 by volume) was injected into the interior space. A metal spring was then placed on top of the stack and joined thereto, with a gasket disposed at the peripheral edge, thus producing an assembled battery. Cyclic voltammetry was carried out at a sweep rate of 1 mV/sec. The results are shown in FIG. 4.

Examples 12 to 14, Comparative Example 1

FIGS. 5 and 6 show cyclic voltammograms for dipyridine-fused benzoquinone (Example 12), Dipyridine-Fused Benzoquinone Derivative C (Example 13) and Dipyridine-Fused Benzoquinone Derivative D (Example 14) according to the invention, and for commercial anthraquinone (Comparative Example 1). Cyclic voltammetry was carried out using 0.1 mol/L tetrabutylammonium/acetonitrile solutions as the electrolyte solutions and at a sweep rate of 50 mV/sec. As is apparent from FIG. 5, the dipyridine-fused benzoquinone of the invention has a redox potential which has shifted toward the noble side compared with anthraquinone, resulting in a higher voltage when used as the positive electrode in a 20 secondary battery. As is apparent from FIG. 6, Dipyridine-Fused Benzoquinone Derivative C and Dipyridine-Fused Benzoquinone Derivative D, when compared with dipyridine-fused benzoquinone, shift even further toward the noble side, resulting in an even higher voltage when used as the positive electrode in a secondary battery.

Example 15: Cyclic Voltammetry of Dipyridine-Fused Benzoquinone Skeleton-Containing Polymer E Solution A 0.1 mol/L solution of lithium perchlorate in γ-butyrolactone was prepared in which the concentration of Dipyridine-Fused Benzoquinone Derivative E was set to 1 mM. Cyclic voltammetry measurement was carried out in a beaker cell using a glassy carbon electrode as the working electrode, a platinum electrode as the counterelectrode and an Ag/AgCl as the reference electrode. Cyclic voltammetry was carried out at a sweep rate of 0.1 V/sec. The results are shown in FIG. 7.

Example 16: Cyclic Voltammetry of Carbon Composite Electrode Produced Using Dipyridine-Fused Benzoquinone Skeleton-Containing Polymer C First, 20 mg of carbon powder and 2.5 mg of polyvinylidene fluoride binder dissolved in 0.25 mL of NMP were added to 2.5 mg of the Dipyridine-Fused Benzoquinone Skeleton-Containing Polymer C, and these ingredients were kneaded in a ball mill. The mixture obtained by about 15 minutes of mixing at 50 Hz was coated onto a glassy carbon substrate, then vacuum-dried overnight at 60° C. hours, giving a carbon composite electrode.

Next, the resulting electrode was immersed in an electrolyte solution, thereby impregnating the electrolyte solution into voids in the electrode. A 1 mol/L solution of lithium perchlorate in γ-butyrolactone was used as the electrolyte solution.

A beaker cell was created by using this carbon composite electrode as the working electrode, a platinum electrode as the counterelectrode and an Ag/AgCl electrode as the reference electrode.

Cyclic voltammetry was carried out at a sweep rate of 10 mV/sec. The results are shown in FIG. 8. FIG. 9 shows the results of measurements of the potential difference with the reference electrode when the charge-discharge capacity was varied.

Example 17: Evaluation of Characteristics of Lithium Ion Battery Produced Using Dipyridine-Fused Benzoquinone Skeleton-Containing Polymer C First, 40 mg of carbon powder and 5.0 mg of polyvinylidene fluoride binder dissolved in 0.50 mL of NMP were added to 5.0 mg of the Polymer C, and these ingredients were kneaded in a ball mill. The mixture obtained by about 15 minutes of mixing at 50 Hz was coated onto aluminum, then vacuum-dried overnight at 60° C. hours, giving a carbon composite electrode.

Next, using the resulting electrode, a battery was assembled as follows. The operations were all carried out in an argon atmosphere.

First, the above electrode was placed on a current collector (battery case), and a 25 μm thick separator composed of Celgard 3501 impregnated with a 1.0 mol/L solution of lithium perchlorate in γ-butyrolactone was placed on top of the electrode. Metallic lithium foil was then stacked thereon, followed in turn by a stainless steel weight, after which a 1.0 mol/L solution of lithium perchlorate in γ-butyrolactone was injected into the interior space. A metal spring was then placed on top of the stack and joined thereto, with a gasket disposed at the peripheral edge, thus producing an assembled battery.

Cyclic voltammetry was carried out at a sweep rate of 1 mV/sec. The results are shown in FIG. 10. FIG. 11 shows the results of measurements of the potential difference with the reference electrode when the charge-discharge capacity was varied.

Example 18: Cyclic Voltammetry of Carbon Composite Electrode Produced Using Dipyridine-Fused Benzoquinone Skeleton-Containing Polymer D First, 20 mg of carbon powder and 2.5 mg of polyvinylidene fluoride binder dissolved in 0.25 mL of NMP were added to 2.5 mg of the Dipyridine-Fused Benzoquinone Skeleton-Containing Polymer D, and these ingredients were kneaded in a ball mill. The mixture obtained by about 15 minutes of mixing at 50 Hz was coated onto a glassy carbon substrate, then vacuum-dried overnight at 60° C. hours, giving a carbon composite electrode.

Next, the resulting electrode was immersed in an electrolyte solution, thereby impregnating the electrolyte solution into voids in the electrode. A 1 mol/L solution of lithium perchlorate in γ-butyrolactone was used as the electrolyte solution.

A beaker cell was created by using this carbon composite electrode as the working electrode, a platinum electrode as the counterelectrode and an Ag/AgCl electrode as the reference electrode.

Cyclic voltammetry was carried out at a sweep rate of 5 mV/sec. The results are shown in FIG. 12. FIG. 13 shows the results of measurements of the potential difference with the reference electrode when the charge-discharge capacity was varied.

Japanese Patent Application Nos. 2015-179565 and 2016-040936 are incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A charge storage material comprising a dipyridine-fused benzoquinone having formula (1-1), (1-2) or (1-3) below

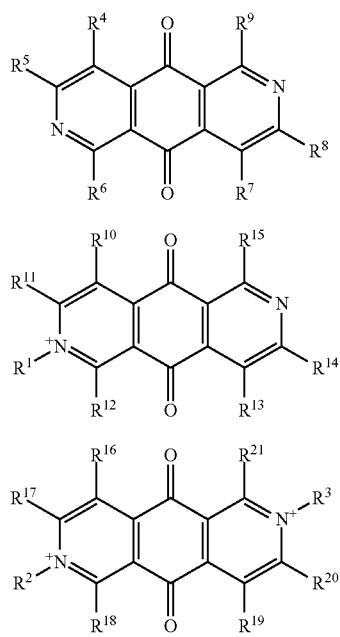

wherein $R^1$ to $R^3$ are each independently an alkyl group of 1 to 12 carbon atoms, a propargyl group, methylstyrene or norbornene;

$R^4$ to $R^9$ are each independently a halogen atom, a hydroxyl group, a mercapto group, an amino group, a substituted or unsubstituted alkyl group of 1 to 12 carbon atoms, a substituted or unsubstituted alkenyl group of 2 to 12 carbon atoms, a substituted or unsubstituted alkynyl group of 2 to 12 carbon atoms, a substituted or unsubstituted aryl group of 6 to 12 carbon atoms, a substituted or unsubstituted heteroaryl group of 3 to 12 carbon atoms, a substituted or unsubstituted alkoxy group of 1 to 12 carbon atoms, a substituted or unsubstituted alkylthio group of 1 to 12 carbon atoms, a substituted or unsubstituted monoalkylamino group of 1 to 12 carbon atoms, a dialkylamino group in which each alkyl group is independently a substituted or unsubstituted alkyl group of 1 to 12 carbon atoms, an alkylcarbonyl group of 2 to 12 carbon atoms, a nitro group, a cyano group, a sulfonic acid group, a phosphonic acid group, a carboxyl group, an aminocarbonyl group, or an alkylaminocarbonyl group of 2 to 12 carbon atoms; and $R^{10}$ to $R^{21}$ are each independently a hydrogen atom, a halogen atom, a hydroxyl group, a mercapto group, an amino group, a substituted or unsubstituted alkyl group of 1 to 12 carbon atoms, a substituted or unsubstituted alkenyl group of 2 to 12 carbon atoms, a substituted or unsubstituted alkynyl group of 2 to 12 carbon atoms, a substituted or unsubstituted aryl group of 6 to 12 carbon atoms, a substituted or unsubstituted heteroaryl group of 3 to 12 carbon atoms, a substituted or unsubstituted alkoxy group of 1 to 12 carbon atoms, a substituted or unsubstituted alkylthio group of 1 to 12 carbon atoms, a substituted or unsubstituted monoalkylamino group of 1 to 12 carbon atoms, a dialkylamino group in which each alkyl group is independently a substituted or unsubstituted alkyl group of 1 to 12 carbon atoms, an alkylcarbonyl group of 2 to 12 carbon atoms, a nitro group, a cyano group, a sulfonic acid group, a phosphonic acid group, a carboxyl group, an aminocarbonyl group, or an alkylaminocarbonyl group of 2 to 12 carbon atoms.

2. An electrode active material comprising the charge storage material of claim 1.

3. An electrode slurry comprising the electrode active material of claim 2 and a solvent.

4. A thin-film produced from the electrode slurry of claim 3.

5. A thin-film comprising the electrode active material of claim 2.

6. An electrode comprising the thin-film of claim 5.

7. An electrode comprising the electrode active material of claim 2.

8. A secondary battery comprising the electrode of claim 7.

9. A lithium ion battery comprising the electrode of claim 7.

10. An air battery comprising the electrode of claim 7.

11. A charge storage material comprising a dipyridine-fused benzoquinone skeleton-containing polymer which includes recurring units of formula (2) and/or (3) below

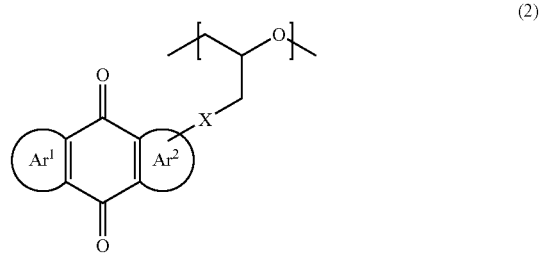

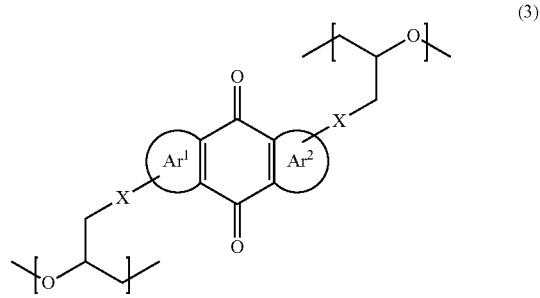

wherein Ar¹ and Ar² are each independently a pyridine ring that forms together with two carbon atoms on the benzoquinone skeleton; and each X is independently a single bond or a divalent group.

12. A charge storage material comprising a dipyridine-fused benzoquinone skeleton-containing polymer which includes recurring units of formula (2-1), (2-2) or (3-1) below

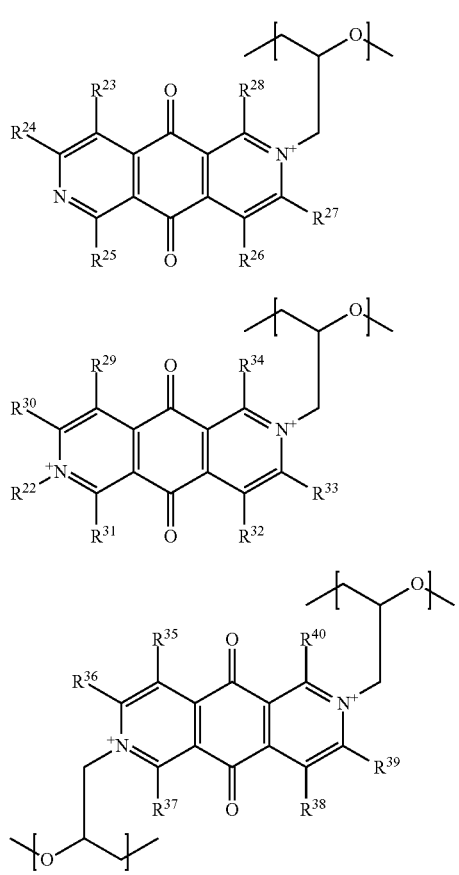

wherein $R^{22}$ is an alkyl group of 1 to 12 carbon atoms, a propargyl group, norbornene or methylstyrene; and $R^{23}$ to $R^{40}$ are each independently a hydrogen atom, a halogen atom, a hydroxyl group, a mercapto group, an amino group, a substituted or unsubstituted alkyl group of 1 to 12 carbon atoms, a substituted or unsubstituted alkenyl group of 2 to 12 carbon atoms, a substituted or unsubstituted alkynyl group of 2 to 12 carbon atoms, a substituted or unsubstituted aryl group of 6 to 12 carbon atoms, a substituted or unsubstituted heteroaryl group of 3 to 12 carbon atoms, a substituted or unsubstituted alkoxy group of 1 to 12 carbon atoms, a substituted or unsubstituted alkylthio group of 1 to 12 carbon atoms, a substituted or unsubstituted monoalkylamino group of 1 to 12 carbon atoms, a dialkylamino group in which each alkyl group is independently a substituted or unsubstituted alkyl group of 1 to 12 carbon atoms, an alkylcarbonyl group of 2 to 12 carbon atoms, a nitro group, a cyano group, a sulfonic acid group, a phosphonic acid group, a carboxyl group, an aminocarbonyl group, or an alkylaminocarbonyl group of 2 to 12 carbon atoms.

13. A dipyridine-fused benzoquinone having formula (1-1), (1-2) or (1-3) below

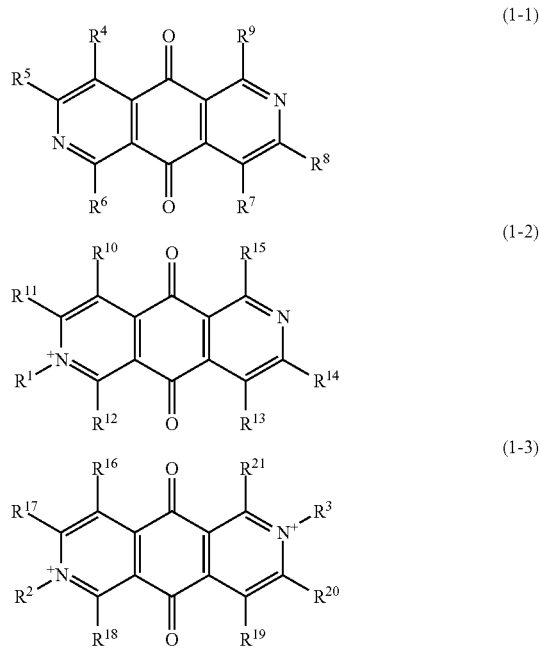

wherein $R^1$ to $R^3$ are each independently an alkyl group of 1 to 12 carbon atoms, a propargyl group, methylstyrene or norbornene;

$R^4$ to $R^9$ are each independently a halogen atom, a hydroxyl group, a mercapto group, an amino group, a substituted or unsubstituted alkyl group of 1 to 12 carbon atoms, a substituted or unsubstituted alkenyl group of 2 to 12 carbon atoms, a substituted or unsubstituted alkynyl group of 2 to 12 carbon atoms, a substituted or unsubstituted aryl group of 6 to 12 carbon atoms, a substituted or unsubstituted heteroaryl group of 3 to 12 carbon atoms, a substituted or unsubstituted alkoxy group of 1 to 12 carbon atoms, a substituted or unsubstituted alkylthio group of 1 to 12 carbon atoms, a substituted or unsubstituted monoalkylamino group of 1 to 12 carbon atoms, a dialkylamino group in which each alkyl group is independently a substituted or unsubstituted alkyl group of 1 to 12 carbon atoms, an alkylcarbonyl group of 2 to 12 carbon atoms, a nitro group, a cyano group, a sulfonic acid group, a phosphonic acid group, a carboxyl group, an aminocarbonyl group, or an alkylaminocarbonyl group of 2 to 12 carbon atoms; and $R^{10}$ to $R^{21}$ are each independently a hydrogen atom, a halogen atom, a hydroxyl group, a mercapto group, an amino group, a substituted or unsubstituted alkyl group of 1 to 12 carbon atoms, a substituted or unsubstituted alkenyl group of 2 to 12 carbon atoms, a substituted or unsubstituted alkynyl group of 2 to 12 carbon atoms, a substituted or unsubstituted aryl group of 6 to 12 carbon atoms, a substituted or unsubstituted heteroaryl group of 3 to 12 carbon atoms, a substituted or unsubstituted alkoxy group of 1 to 12 carbon atoms, a substituted or unsubstituted alkylthio group of 1 to 12 carbon atoms, a substituted or unsubstituted monoalkylamino group of 1 to 12 carbon atoms, a dialkylamino group in which each alkyl group is independently a substituted or unsubstituted alkyl group of 1 to 12 carbon atoms, an alkylcarbonyl group of 2 to 12 carbon atoms, a nitro group, a cyano group, a sulfonic acid group, a phosphonic acid group, a carboxyl group, an aminocarbonyl group, or an alkylaminocarbonyl group of 2 to 12 carbon atoms.

14. A dipyridine-fused benzoquinone skeleton-containing polymer comprising recurring units of formula (2) and/or (3) below

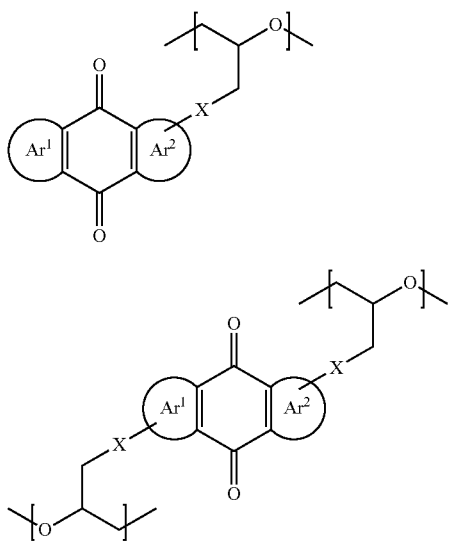

wherein $Ar^1$ and $Ar^2$ are each independently a pyridine ring that forms together with two carbon atoms on the benzoquinone skeleton; and each X is independently a single bond or a divalent group.

15. A dipyridine-fused benzoquinone skeleton-containing polymer comprising recurring units of formula (2-1), (2-2) or (3-1) below

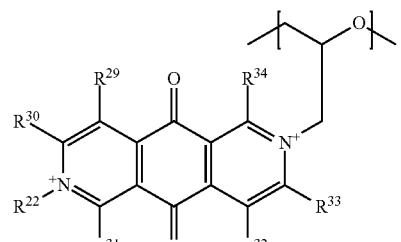

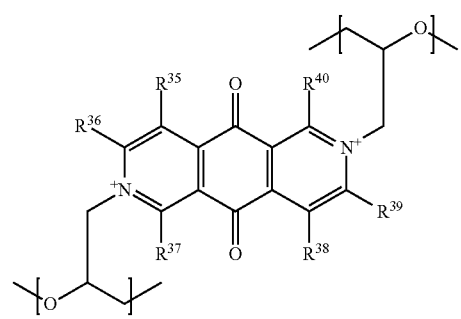

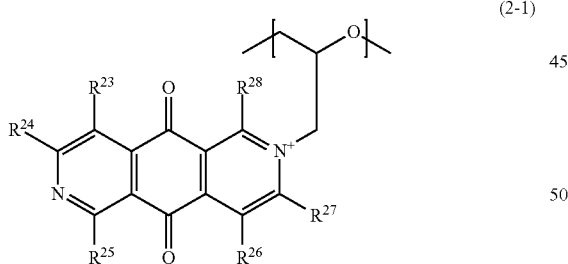

wherein $R^{22}$ is an alkyl group of 1 to 12 carbon atoms, a propargyl group, norbornene or methylstyrene; and $R^{23}$ to $R^{40}$ are each independently a hydrogen atom, a halogen atom, a hydroxyl group, a mercapto group, an amino group, a substituted or unsubstituted alkyl group of 1 to 12 carbon atoms, a substituted or unsubstituted alkenyl group of 2 to 12 carbon atoms, a substituted or unsubstituted alkynyl group of 2 to 12 carbon atoms, a substituted or unsubstituted aryl group of 6 to 12 carbon atoms, a substituted or unsubstituted heteroaryl group of 3 to 12 carbon atoms, a substituted or unsubstituted alkoxy group of 1 to 12 carbon atoms, a substituted or unsubstituted alkylthio group of 1 to 12 carbon atoms, a substituted or unsubstituted monoalkylamino group of 1 to 12 carbon atoms, a dialkylamino group in which each alkyl group is independently a substituted or unsubstituted alkyl group of 1 to 12 carbon atoms, an alkylcarbonyl group of 2 to 12 carbon atoms, a nitro group, a cyano group, a sulfonic acid group, a phosphonic acid group, a carboxyl group, an aminocarbonyl group, or an alkylaminocarbonyl group of 2 to 12 carbon atoms.

* * * * *